(12) United States Patent
Verkman et al.

(10) Patent No.: US 7,888,332 B2
(45) Date of Patent: Feb. 15, 2011

(54) HYDRAZIDE-CONTAINING CFTR INHIBITOR COMPOUNDS AND USES THEREOF

(75) Inventors: Alan S. Verkman, San Francisco, CA (US); Nitin D. Sonawane, San Francisco, CA (US); Chatchai Muanprasat, Nakhonpathom (TH)

(73) Assignee: The Regents of the University of California, Oakland, CA (US)

( * ) Notice: Subject to any disclaimer, the term of this patent is extended or adjusted under 35 U.S.C. 154(b) by 384 days.

(21) Appl. No.: 12/175,982

(22) Filed: Jul. 18, 2008

(65) Prior Publication Data
US 2009/0048207 A1 Feb. 19, 2009

Related U.S. Application Data

(62) Division of application No. 11/093,749, filed on Mar. 29, 2005, now Pat. No. 7,414,037.

(60) Provisional application No. 60/557,930, filed on Mar. 30, 2004.

(51) Int. Cl.
*A01N 43/04* (2006.01)
*A61K 31/715* (2006.01)

(52) U.S. Cl. ................... 514/53; 514/615; 514/313; 514/563; 514/375; 435/375

(58) Field of Classification Search .................. None
See application file for complete search history.

(56) References Cited

U.S. PATENT DOCUMENTS

| | | | |
|---|---|---|---|
| 5,023,333 A | 6/1991 | Hubele | 546/175 |
| 6,172,108 B1 | 1/2001 | Vega et al. | 514/485 |
| 6,331,555 B1 * | 12/2001 | Hirth et al. | 514/378 |
| 2008/0171793 A1 | 7/2008 | Verkman et al. | 514/639 |
| 2009/0253799 A1 | 10/2009 | Verkman et al. | 514/586 |

FOREIGN PATENT DOCUMENTS

| | | |
|---|---|---|
| EP | 0 952 159 A2 | 10/1999 |
| GB | 1 334 400 | 10/1973 |
| GB | 1446980 | 8/1976 |
| GB | 2 107 074 A | 4/1983 |
| JP | 59-162541 | 9/1984 |
| WO | WO 01/30333 A2 | 5/2001 |
| WO | WO 2005/094374 | 10/2005 |
| WO | WO 2008/079897 | 7/2008 |
| WO | WO 2009/120803 | 10/2009 |
| WO | WO 2009/146144 | 12/2009 |

OTHER PUBLICATIONS

Verma et al.; {Syntheses and anti-inflammatory activities of substituted arylamino-(N'-benzylidene)acetohydrazides and derivatives, Archiv der Pharmazie (Weinheim, Germany) (1984), 317(10), 890-4}.*

Caci et al., "Evidence for direct CFTR inhibition by CFTR$_{inh}$-172 based on Arg$^{347}$ mutagenesis," *Biochem. J.* 413(1):135-142, 2008.

Carmeliet, "Electrophysiology on the Molecular Way," *Verh. K. Acad. Geneeskd. Belg.* 55:5-26, 1993.

Galietta et al., "Cell-based assay for high-throughput quantitative screening of CFTR chloride transport agonists," *Am. J. Physiol. Cell Physiol.* 281(5):C1734-C1742, 2001.

Salinas et al., "Submucosal gland dysfunction as a primary defect in cystic fibrosis," *The FASEB Journal* 19:431-433, 2005.

Sonawane et al., "Thiazolidinone CFTR inhibitors with improved water solubility identified by structure-activity analysis," *Bioorganic & Medicinal Chemistry* 16:8187-8195, 2008.

Thiagarajah et al., "CFTR pharmacology and its role in intestinal fluid secretion," *Curr. Opin. Pharmacol.* 3:594-599, 2003.

Thiagarajah et al., "A small molecule CFTR inhibitor produces cystic fibrosis-like submucosal gland fluid secretions in normal airways," *FASEB J.* 18:875-877, 2004.

Thiagarajah et al., "New drug targets for cholera therapy," *Trends Pharmacol. Sci.* 26(4):172-175, 2005.

Aminabhavi, T.M. et al., "Synthesis and Characterization of Biologically Active Organosilicon and Organotin Complexes of Phenylglycyl Hydrazones," *Inorganic Chimica Acta*, 135(2):139-143, 1987.

Beresnevicius et al., "Interaction of aminoquinolines with unsaturated carboxylic acids. 1. Synthesis of N-quinolyl-β-alanines and their biological activity," *Chemistry of Heterocyclic Compounds*, Translation of Khimiya Geterotsiklicheskikh Soedinenii, New York, 36(4):432-438, 2000.

Brock, M. W. et al., "Selective Open-channel Block of *Shaker* (Kv1) Potassium Channels by S-nitrosodithiothreitol (SNDTT)," *J. Gen. Physiol.*, 118:113-133, Jul. 2001.

(Continued)

*Primary Examiner*—Daniel M Sullivan
*Assistant Examiner*—Chukwuma O Nwaonicha
(74) *Attorney, Agent, or Firm*—Seed IP Law Group PLLC

(57) ABSTRACT

The invention provides compositions, pharmaceutical preparations and methods for inhibition of cystic fibrosis transmembrane conductance regulator protein (CFTR) that are useful for the study and treatment of CFTR-mediated diseases and conditions. The compositions and pharmaceutical preparations of the invention may comprise one or more hydrazide-containing compounds, and may additionally comprise one or more pharmaceutically acceptable carriers, excipients and/or adjuvants. The methods of the invention comprise, in certain embodiments, administering to a patient suffering from a CFTR-mediated disease or condition, an efficacious amount of a hydrazide-containing compound. In other embodiments the invention provides methods of inhibiting CFTR that comprise contacting cells in a subject with an effective amount of a hydrazide-containing compound. In addition, the invention features a non-human animal model of CFTR-mediated disease which model is produced by administration of a hydrazide-containing compound to a non-human animal in an amount sufficient to inhibit CFTR.

39 Claims, 18 Drawing Sheets

OTHER PUBLICATIONS

Chao, A. C. et al., "Activation of intestinal CFTR Cl⁻ channel by heat-stable enterotoxin and guanylin via cAMP-dependent protein kinase," *The EMBO Journal*, 13(5):1065-1072, Mar. 1, 1994.

Chemical Abstracts, vol. 55, No. 14, Jul. 10, 1961, (Columbus, OH, USA), pp. 13350-13351, see abstract No. 13350h-I, Kondo et al., "N-Arylglycine Series Chemotherapeutics. I. Synthesis of Aryl Sulfone Derivatives," Yakugaku Zasshi, 1961, vol. 81, pp. 97-100.

Dawson, D. C. et al., "CFTR: Mechanism of Anion Conduction," *Physiological Reviews*, 79(Supp No. 1):S47-S75, Jan. 1999.

Giri et al., "Organo-fluorine compounds. I. Synthesis of some substituted glycines and related compounds of potential biological activity," *Journal of the Indian Chemical Society* 46(5):441-443, 1969.

Grubb, B. R. And Boucher, R. C., "Pathophysiology of Gene-Targeted Mouse Models for Cystic Fibrosis," *Physiological Reviews*, 79(Supp No. 1):S193-S214, Jan. 1999.

Hammam et al., "Synthesis and reactions of 1, 2, 4-oxadiazole derivatives of expected biological activity," *Egyptian Journal of Chemistry* 27(3):407-411, 1985.

Jayaraman, S. et al., "Submucosal gland secretions in airways from cystic fibrosis patients have normal [Na⁺] and pH but elevated viscosity," *PNAS*, 98(14):8119-8123, Jul. 3, 2001.

Kimberg, D. V. et al., "Stimulation of Intestinal Mucosal Adenyl Cyclase by Cholera Enterotoxin and Prostglandins," *The Journal of Clinical Investigation*, 50:1218-1230, 1971.

Lohi, H. et al., "Upregulation of CFTR expression but not SLC26A3 and SLC9A3 in ulcerative colitis," *Am. J. Physiol Gastrointest Liver Physiol.*, 283:G567-G575, 2002.

Ma, T. et al., "High-affinity Activators of Cystic Fibrosis Transmembrane Conductance Regulator (CFTR) Chloride Conductance Identified by High-throughput Screening," *The Journal of Biological Chemistry*, 277(40):37235-37241, Oct. 4, 2002.

Ma, T. et al., "Thiazolidinone CFTR inhibitor identified by high-throughput screening blocks cholera toxin-induced intestinal fluid secretion," *The Journal of Clinical Investigation*, 110(11):1651-1658, Dec. 2002.

Mazur et al., "Derivatives of N-(4-quinazolinyl)-α-amino and quinazolin-4-on-3-yl carboxylic acids and their antimicrobial activity," *Farmatsevtichnii Zhurnal*, Kiev, (4):34-37, 1980.

McCarty, N. A., "Permeation Through the CFTR Chloride Channel," *The Journal of Experimental Biology*, 203:1947-1962, 2000.

Misra et al., "Possible antituberculous compounds. XV. N-2-Thiazolylglycines, 1-acyl-4-arlsemicarbazides, 1-acyl-4-arylthiosemicarbazides, and N1-(N-arylglycy1)-N2-(arylidane or alkylidene) hydrazines," *Journal of the Indian Chemical Society* 40(9):799-802, 1963.

Misra et al., "1, 3, 5-S-Triazine. Synthesis of some possible antituberculous compounds," *Journal of the Indian Chemical Society* 48(5):448-450, 1971.

Muanprasat, C. et al., "Discovery of Glycine Hydrazide Pore-occluding CFTR Inhibitors: Mechanism, Structure-Activity Analysis, and In Vivo Efficacy," *J. Gen. Physiol.*, 124:125-137, Aug. 2004.

Noone, P. G. and Knowles, M. R., "'CFTR-opathies': disease phenotypes associated with cystic fibrosis transmembrane regulator gene mutations," *Respir. Res.*, 2:328-332, 2001.

Pilewski, J. M. and Frizzell, R. A., "Role of CFTR in Airway Disease," *Physiological Reviews*, 79(Supp No. 1):S215-S255, Jan. 1999.

Pottosin, I. I. et al., "Cooperative Block of the Plant Endomembrane Ion Channel by Ruthenium Red," *Biophysical Journal*, 77:1973-1979, Oct. 1999.

Rabe, A. et al., "Cl⁻ channel Inhibition by glibenclamide is not specific for the CFTR-type Cl⁻ channel," *Pflügers Arch—Eur. J. Physiol*, 429:659-662, 1995.

Ramamurthy, B. and Bhatt, M. V., "Synthesis and Antitubercular Activity of N-(2-Naphthyl)glycine Hydrazide Analogues," *Journal of Medicinal Chemistry*, 32:2421-2426, 1989.

Sheppard, D. N. and Robinson, K. A., "Mechanism of glibenclamide inhibition of cystic fibrosis transmembrane conductance regulator Cl⁻ channels expressed in a murine cell line," *Journal of Physiology*, 503.2:333-346, 1997.

Shultz, B. D. et al., "Pharmacology of CFTR Chloride Channel Activity," *Physiological Reviews*, 79(Supp No. 1):S109-S144, Jan. 1999.

Snyder, J. D. and Merson, M. H., "The magnitude of the global problem of acute diarrhoeal disease: a review of active surveillance data," *Bulletin of the World Health Organization*, 60(4):605-613, 1982.

Solomko et al., "N-Aryl-β-amino acids. V. Hydrazides of N-aryl-β-alanines," *Khimiko-Farmatsevticheskii Zhurnal* 5(11):18-21, 1971.

Spira, W. M. et al., "Simple Adult Rabbit Model for *Vibrio cholerae* and Enterotoxigenic *Escherichia coli* Diarrhea," *Infection and Immunity*, 32(2):739-747, May 1981.

Verma, M. et al., "Syntheses and Anti-inflammatory Activities of Substituted Arylamino-(N'-benzylidene)acetohydrazides and Derivatives," *Arch. Pharm. (Weinheim)*, 317:890-894, 1984.

Wong, P. Y. D., "CFTR gene and male fertility," *Molecular Human Reproduction*, 4(2):107-110, 1998.

Yang, H. et al., "Nanomolar Affinity Small Molecule Correctors of Defective ΔF508-CFTR Chloride Channel Gating," *The Journal of Biological Chemistry*, 278(37):35079-35085, Sep. 12, 2003.

Zhou, Z. et al., "Probing an Open CFTR Pore with Organic Anion Blockers," *J. Gen. Physiol.*, 120:647-662, Nov. 2002.

CAS Registry No. 664312-09-8, Mar. 18, 2004.
CAS Registry No. 643741-81-5, Jan. 30, 2004.
CAS Registry No. 610257-12-0, Oct. 29, 2003.
CAS Registry No. 601498-97-9, Oct. 9, 2003.
CAS Registry No. 595552-29-7, Sep. 30, 2003.
CAS Registry No. 594871-24-6, Sep. 29, 2003.
CAS Registry No. 594870-13-0, Sep. 29, 2003.
CAS Registry No. 640704-49-0, Jan. 23, 2004.
CAS Registry No. 640698-93-7, Jan. 23, 2004.
CAS Registry No. 606483-72-1, Oct. 19, 2003.
CAS Registry No. 601498-88-8, Oct. 9, 2003.
CAS Registry No. 595553-21-2, Sep. 30, 2003.
CAS Registry No. 595550-90-6, Sep. 30, 2003.
CAS Registry No. 594870-90-3, Sep. 29, 2003.
CAS Registry No. 594869-56-4, Sep. 29, 2003.

Mazur et al., "Derivatives of N-(4-quinazolinyl)-α-amino and quinazolin-4-on-3-yl carboxylic acids and their antimicrobial activity," *Farmatsevtichnii Zhurnal*, Kiev, (4):34-37, 1980 (Abstract Only).

Sonawane et al., "Luminally active, nonabsorbable CFTR inhibitors as potential therapy to reduce intestinal fluid loss in cholera," *The FASEB Journal*, express article 10.1096/fj.05-4818fje, Nov. 29, 2005.

Sonawane et al., "Lectin Conjugates as Potent, Nonabsorbable CFTR Inhibitors for Reducing Intestinal Fluid Secretion in Cholera," *Gastroenterology* 132(4):1234-1244, Apr. 2007.

Sonawane et al., "Nanomolar CFTR Inhibition by Pore-Occluding Divalent Polyethylene Glycol-Malonic Acid Hydrazides," *Chemistry & Biology* 15(7):718-728, Jul. 21, 2008.

Verkman et al., "CFTR chloride channel drug discovery—inhibitors as antidiarrheals and activators for therapy of cystic fibrosis." *Curr Pharm Des.* 12(18):2235-2247, 2006.

Yang et al., "Small-Molecule CFTR Inhibitors Slow Cyst Growth in Polycystic Kidney Disease," *J Am Soc Nephrol* 19:1300-1310, 2008.

\* cited by examiner

OxaH-110

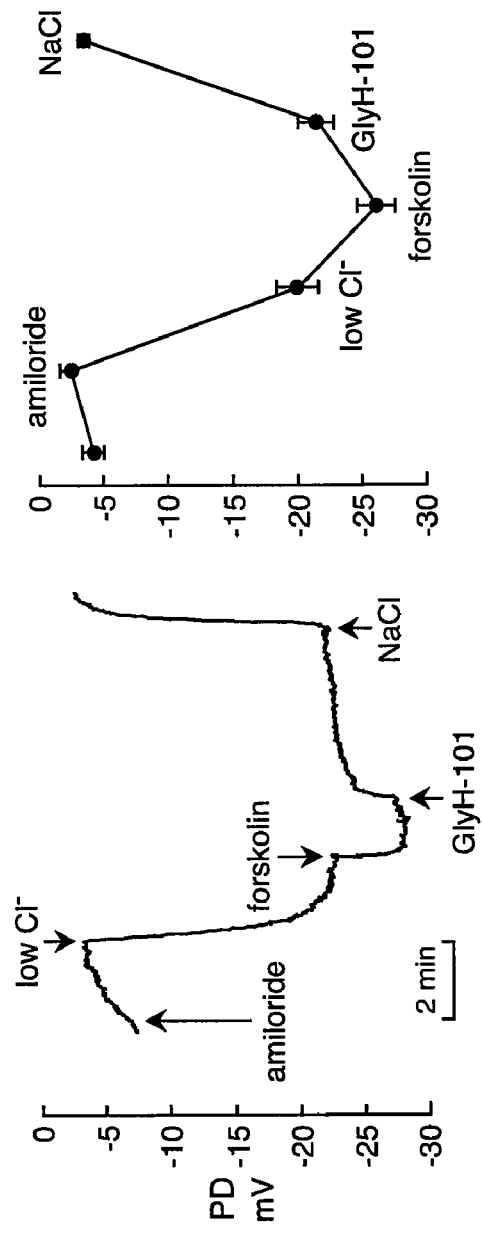
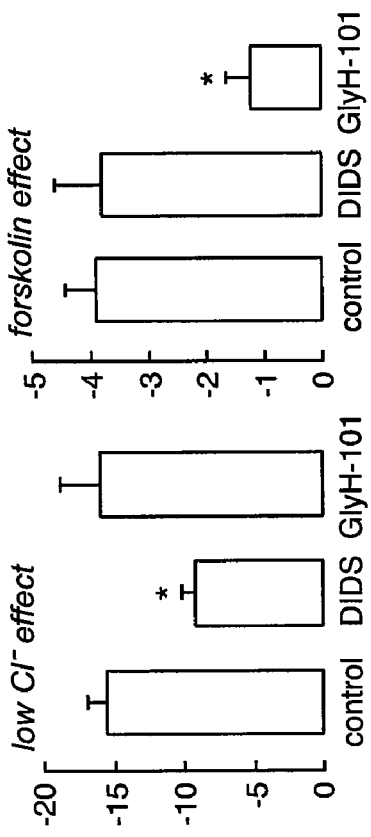
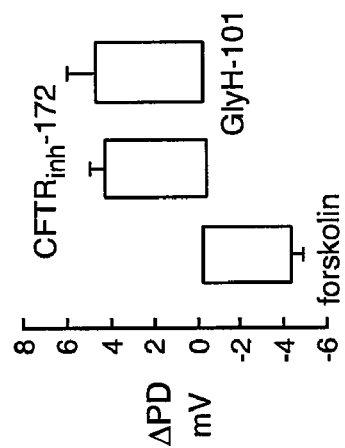
FIG. 6A
FIG. 6B
FIG. 6C

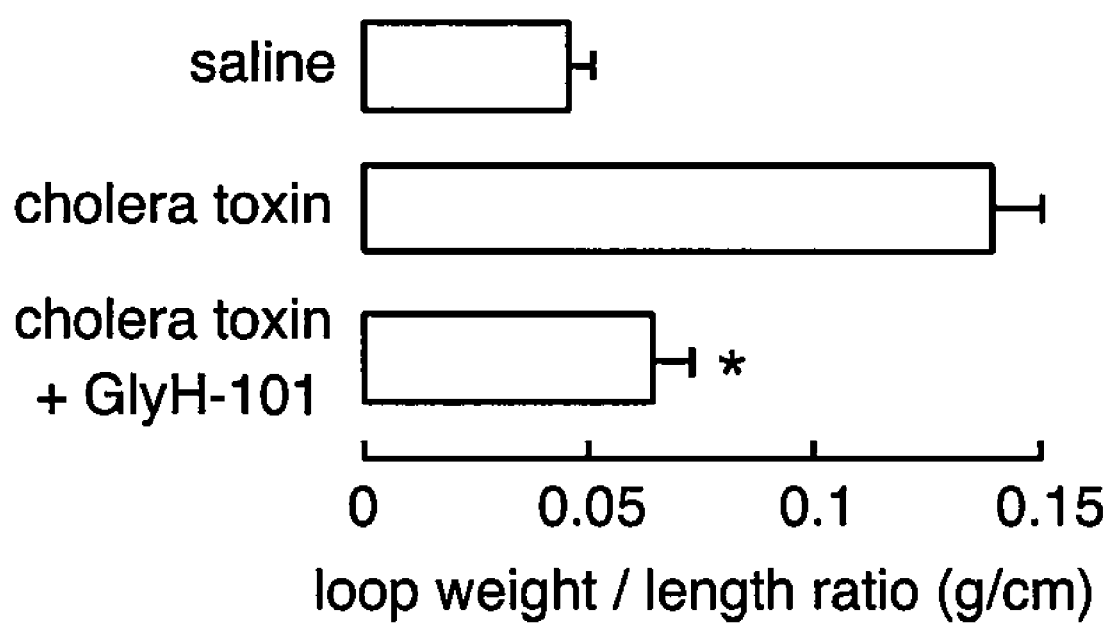

HYDRAZIDE-CONTAINING CFTR INHIBITOR COMPOUNDS AND USES THEREOF

CROSS-REFERENCE TO RELATED APPLICATIONS

This application is a divisional of U.S. patent application Ser. No. 11/093,749, now issued on Aug. 19, 2008 as U.S. Pat. No. 7,414,037, which has a filing date of Mar. 29, 2005, which claims the benefit U.S. Provisional Application No. 60/557,930, filed Mar. 30, 2004, all of which applications are incorporated herein by reference in their entireties.

STATEMENT REGARDING FEDERALLY SPONSORED RESEARCH

This invention was made with government support under grant nos. HL73854, EB00415, EY13574, DK35124, DK43840, and UC1 AI062530-01 awarded by the National Institutes of Health. The government has certain rights in this invention.

BACKGROUND OF THE INVENTION

The cystic fibrosis transmembrane conductance regulator protein (CFTR) is a cAMP-activated chloride ($Cl^-$) channel expressed in epithelial cells in mammalian airways, intestine, pancreas and testis. CFTR is the chloride-channel responsible for cAMP-mediated $Cl^-$ secretion. Hormones, such as a β-adrenergic agonist, or a toxin, such as cholera toxin, leads to an increase in cAMP, activation of cAMP-dependent protein kinase, and phosphorylation of the CFTR $Cl^-$ channel, which causes the channel to open. An increase in cell $Ca^{2+}$ can also activate different apical membrane channels. Phosphorylation by protein kinase C can either open or shut $Cl^-$ channels in the apical membrane. CFTR is predominantly located in epithelia where it provides a pathway for the movement of $Cl^-$ ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea.

The hereditary lethal disease cystic fibrosis (CF) is caused by mutations in CFTR. Observations in human cystic fibrosis (CF) patients and CF mouse models indicate the functional importance of CFTR in intestinal and pancreatic fluid transport, as well as in male fertility (Grubb et al., 1999, *Physiol. Rev.* 79:S193-S214; Wong, P. Y., 1997, *Mol. Hum. Reprod.* 4:107-110). However, the mechanisms remain unclear by which defective CFTR produces airway disease, which is the principal cause of morbidity and mortality in CF (Pilewski et al., 1999, *Physiol. Rev.* 79:S215-S255). Major difficulties in understanding airway disease in CF include the inadequacy of CF mouse models, which manifest little or no airway disease, the lack of large animal models of CF, and the limited availability of human CF airways that have not been damaged by chronic infection and inflammation. High-affinity, CFTR-selective inhibitors have not been available to study airway disease mechanisms in CF or to create the CF phenotype in large animal models.

High-affinity CFTR inhibitors also have clinical applications in the therapy of secretory diarrheas and cystic kidney disease, and in inhibiting male fertility. Several CFTR inhibitors have been discovered, although most of which have a weak potency and lack CFTR specificity. The oral hypoglycemic agent glibenclamide inhibits CFTR $Cl^-$ conductance from the intracellular side by an open channel blocking mechanism (Sheppard & Robinson, 1997 *J. Physiol.*, 503: 333-346; Zhou et al., 2002, *J. Gen. Physiol.*, 120:647-662) at high micromolar concentrations where it affects other $Cl^-$ and cation channels (Edwards & Weston, 1993; Rabe et al., 1995, *Br. J. Pharmacol.*, 110: 1280-1281; Schultz et al., 1999, *Physiol. Rev.*, 79:S109-S144). Other non-selective anion transport inhibitors including diphenylamine-2-carboxylate (DPC), 5-nitro-2(3-phenylpropyl-amino)benzoate (NPPB), and flufenamic acid also inhibit CFTR by occluding the pore at an intracellular site (Dawson et al., 1999, *Physiol. Rev.*, 79:S47-S75; McCarty, 2000, *J. Exp. Biol.*, 203:1947-1962).

There is accordingly a need for CFTR inhibitors, particularly those that are water-soluble. The present invention addresses these needs, as well as others, and overcomes deficiencies found in the background art.

Literature

Ma et al., 2002, *J. Clin. Invest.*, 110:1651-1658 describes a thiazolidinone class of CFTR inhibitor.

SUMMARY OF THE INVENTION

The invention provides compositions, pharmaceutical preparations and methods for inhibition of cystic fibrosis transmembrane conductance regulator protein (CFTR) that are useful for the study and treatment of CFTR-mediated diseases and conditions. The compositions and pharmaceutical preparations of the invention may comprise one or more hydrazide-containing compounds, and may additionally comprise one or more pharmaceutically acceptable carriers, excipients and/or adjuvants. The methods of the invention comprise, in certain embodiments, administering to a patient suffering from a CFTR-mediated disease or condition, an efficacious amount of a hydrazide-containing compound. In other embodiments the invention provides methods of inhibiting CFTR that comprise contacting cells in a subject with an effective amount of a hydrazide-containing compound. In addition, the invention features a non-human animal model of CFTR-mediated disease which model is produced by administration of a hydrazide-containing compound to a non-human animal in an amount sufficient to inhibit CFTR.

These and other objects, advantages, and features of the invention will become apparent to those persons skilled in the art upon reading the details of the hydrazide-containing compounds as more fully described below.

BRIEF DESCRIPTIONS OF THE DRAWINGS

The invention will be more fully understood by reference to the following drawings, which are for illustrative purposes only.

FIG. 1A is a schematic representation of a screening technique used for detection of CFTR inhibitors. CFTR was maximally stimulated by multiple agonists in stably transfected epithelial cells co-expressing human CFTR and a yellow fluorescent protein (YFP) having $Cl^-/I^-$ sensitive fluorescence. After addition of a test compound, $I^-$ influx was induced by adding an $I^-$ containing solution.

Figure 3A:
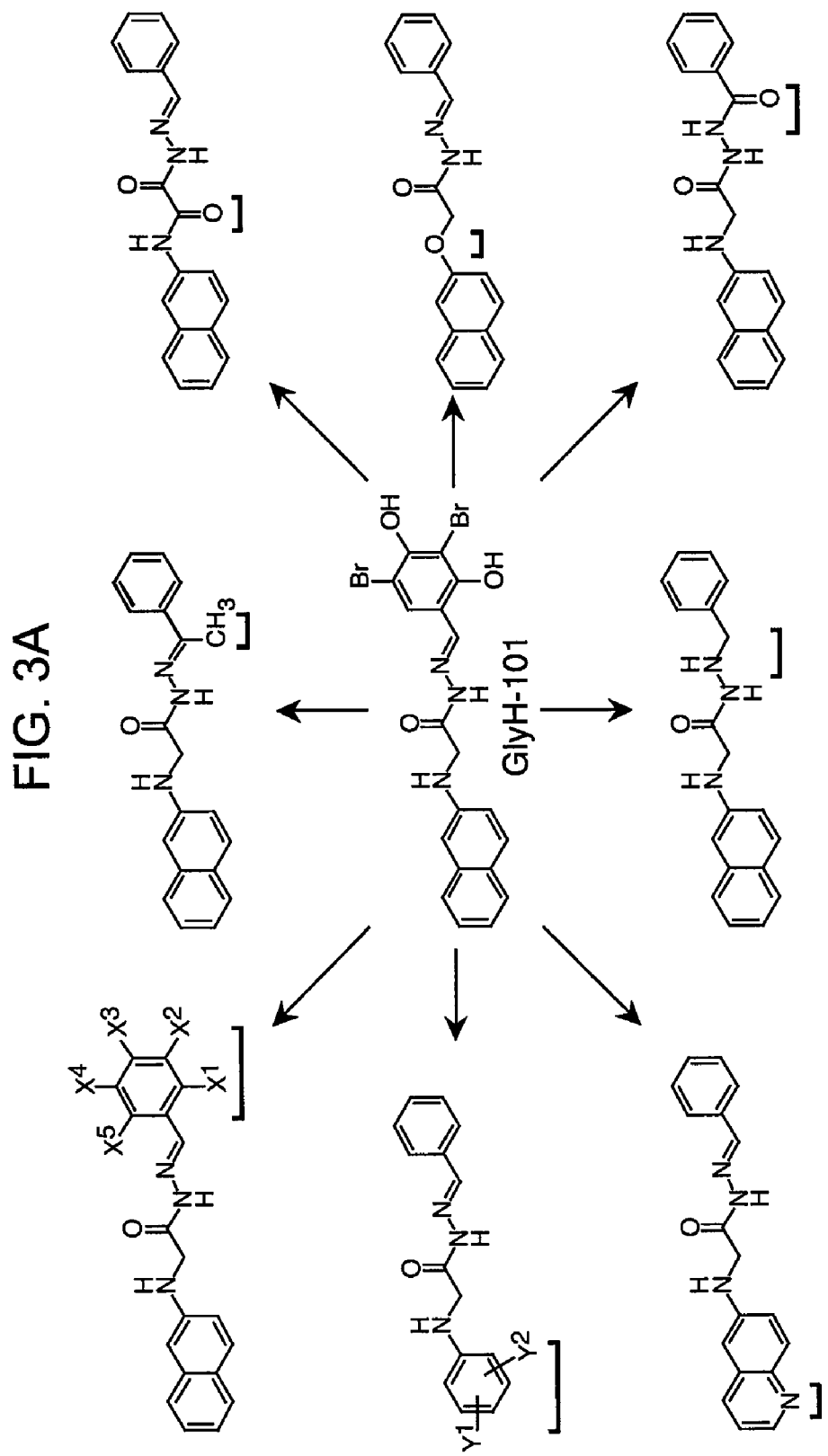

FIG. 3A provides chemical structures of a class of GlyH-101 analogs with sites of modification indicated with brackets.

Figure 3B:
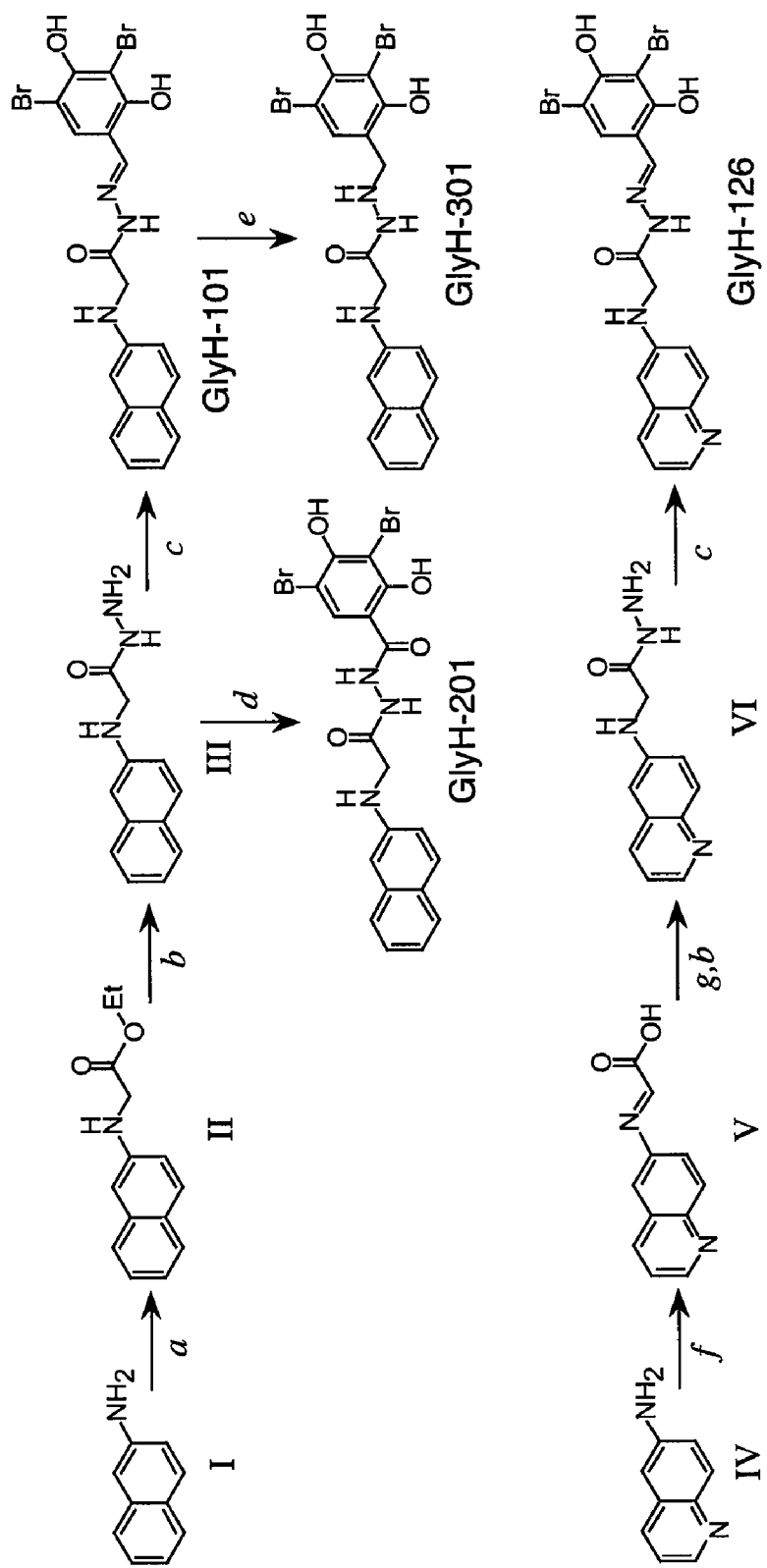

FIG. 3B depicts the reaction scheme for the synthesis of GlyH-101, N-(6-quinolinyl)-[(3,5-dibromo-2,4-dihydroxyphenyl)methylene]glycine hydrazide (referred to herein as GlyH-126), 3,5-dibromo-2,4-di-hydroxy-[2-(2-napthalenamine)aceto]benzoic acid hydrazide (referred to herein as GlyH-201), and N-2-napthalenyl-[(3,5-dibromo-2,4-dihydroxyphenyl)methyl]glycine hydrazide (referred to herein as GlyH-301). Reagents and conditions: (a) ICH$_2$COOEt, NaOAc, 95° C.; (b) N$_2$H$_4$.H$_2$O EtOH/reflux; (c) 3,5-di-Br-2,4-di-OH-Ph-CHO, EtOH/reflux; (d) 3,5-di-Br-2,4-di-OH-Ph-COCl, pyridine, 22° C.; (e) N$_2$H$_4$.H$_2$O, Pd/C (10%), DMF/reflux; (0 glyoxalic acid, 10° C.; (g) Na$_2$BH$_3$CN/CH$_3$CN, 48 h; dry HCl, EtOH.

Figure 3C:
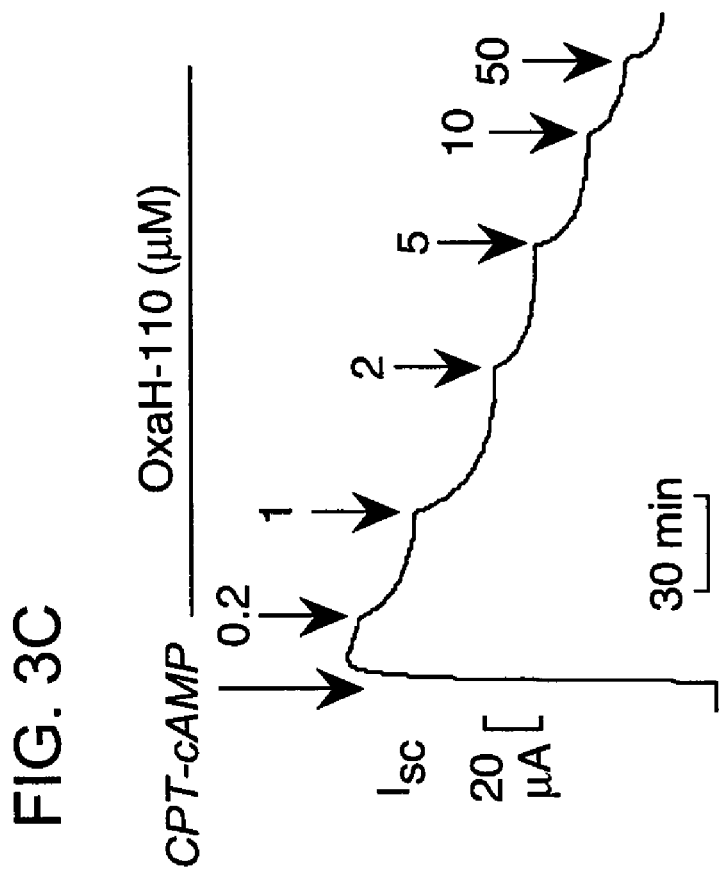
Figure 3C:
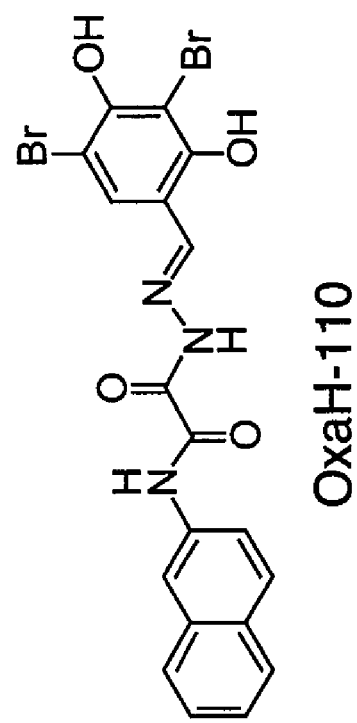

FIG. 3C is a graph representing N-2-napthalenyl-[(3,5-dibromo-2,4-dihydroxyphenyl)methylene]oxamic acid hydrazide (referred to herein as OxaH-110) inhibition of short-circuit current expressing human CFTR (right panel) and the structure of OxaH-110 (left panel). CFTR was stimulated by 100 μM CPT-cAMP.

Figure 4A:
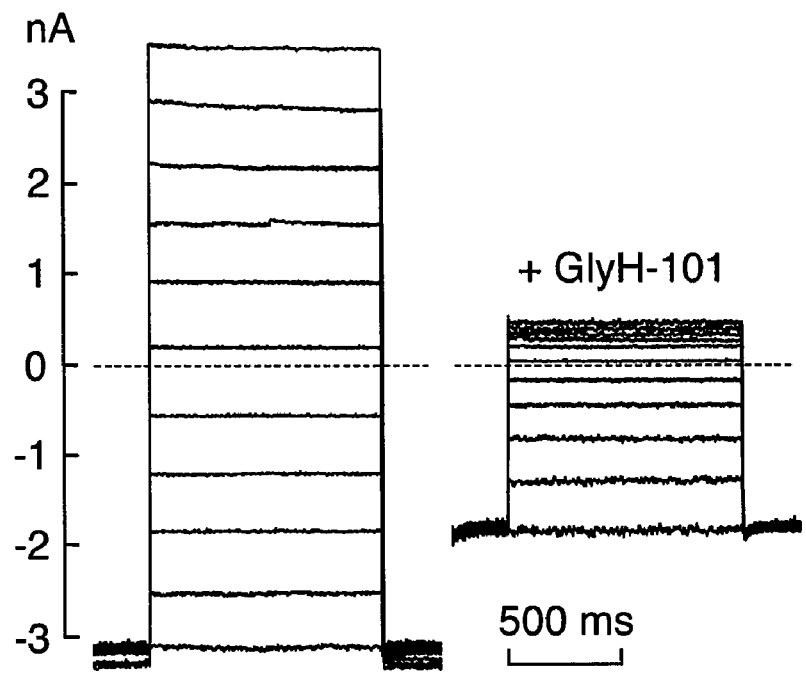

FIG. 4A is a graph illustrating of GlyH-101 inhibition measured in whole-cell patch clamp experiments on FRT cells expressing human CFTR. Whole-cell membrane currents were evoked by voltages from −100 to +100 mV in 20 mV steps after maximal CFTR stimulation by 5 μM forskolin. The graph on the left represents measurements before GlyH-101 was added and the graph on the right represents measurements after GlyH-101 was added.

Figure 4B:
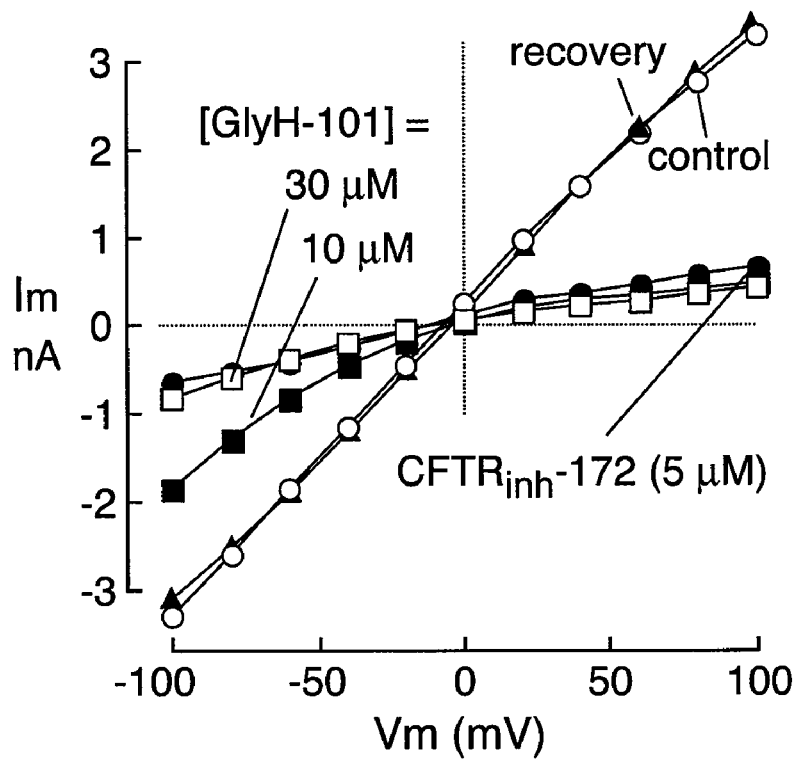

FIG. 4B is a graph representing current-voltage relationships in the absence of inhibitors (control, open circles), after addition of 10 μM (filled squares) and 30 μM GlyH-101 (filled circles), after washout of 10 μM GlyH-101 (recovery, triangles) and after addition of 5 μM CFTR$_{inh}$-172 (filled circles).

Figure 4C:
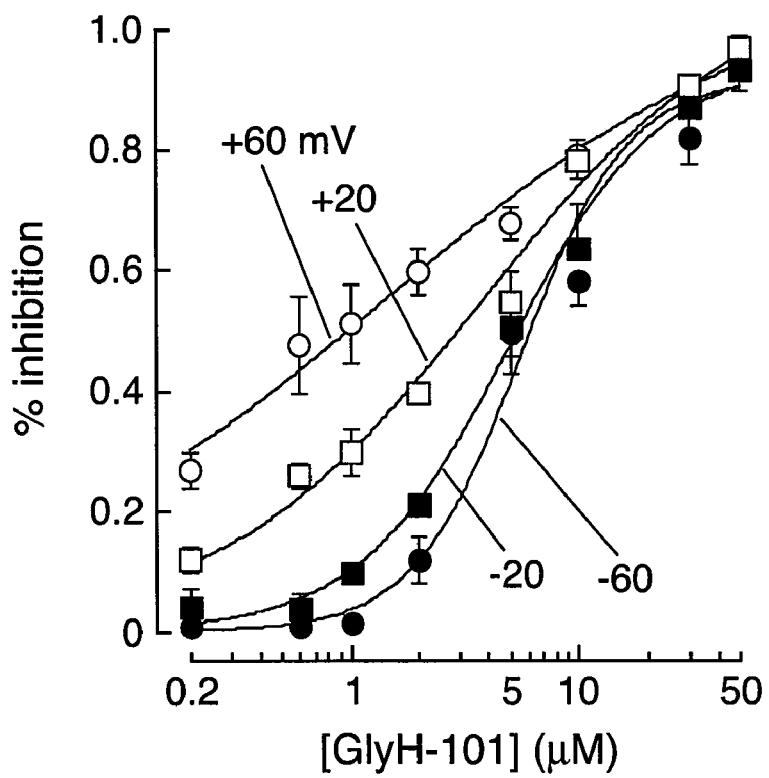

FIG. 4C is a graph illustrating of dose-response relationships determined for GlyH-101 at the indicated membrane potentials.

Figure 4D:
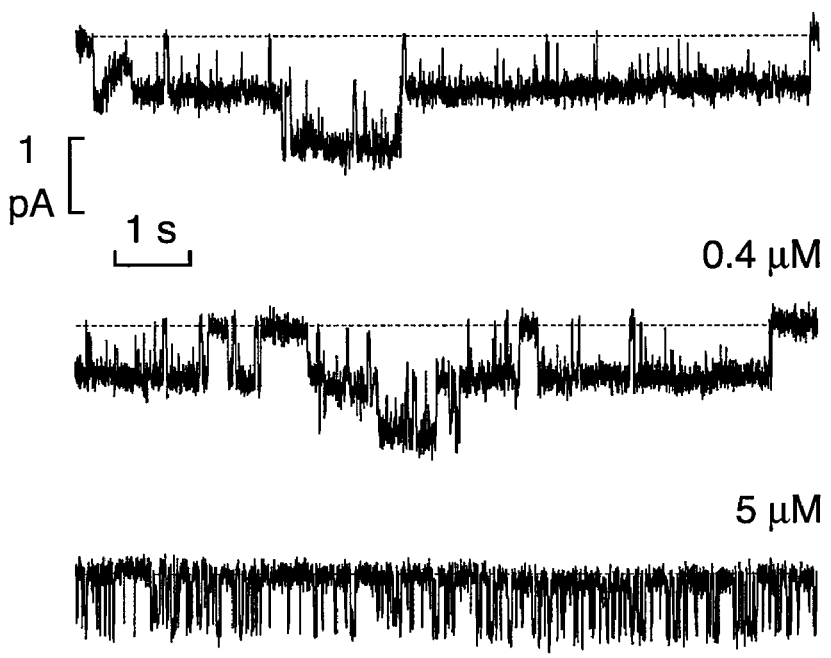

FIG. 4D is a graph illustrating of representative cell-attached patch-clamp recordings showing CFTR single channel activity at GlyH-101 concentrations of 0, 0.4 and 5 μM. Dashed lines show zero current level (channels closed) with downward deflections indicating channel openings (Cl⁻ ions moving from pipette into the cell). Pipette potential was −60 mV.

Figure 5A:
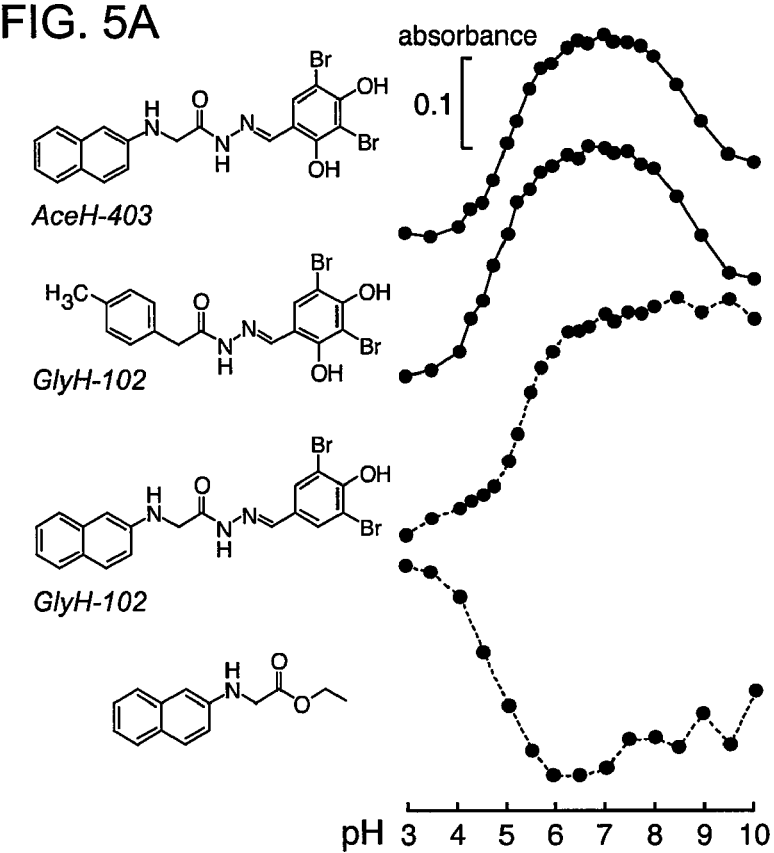

FIG. 5A is a graph illustrating the pH-dependent absorbance changes (right panel) of the chemical compounds (10 μM) (corresponding chemical structures, left panel) in NaCl (100 mM) containing MES, HEPES, boric acid, and citric acid (each 10 mM) titrated to different pH using HCl/NaOH. Absorbance changes measured at analytical wavelengths of 346, 348, 346, and 236 nm (top to bottom).

Figure 5B:
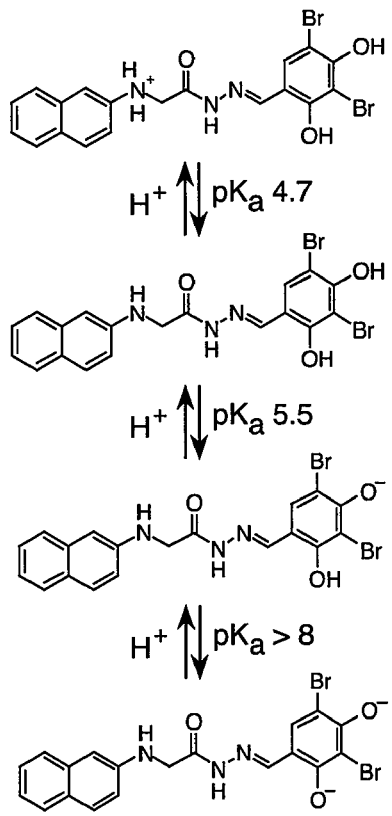

FIG. 5B is a representation of deduced ionic equilibria of GlyH-101 showing pKa values.

FIG. 6A is a graph illustrating GlyH-101 inhibition in a nasal potential difference (PD) recording showing responses to amiloride and low Cl⁻ solutions (left panel) or averaged PD values (right panel, mean±SE, n=5). Where indicated the low Cl⁻ solutions contained forskolin without or with GlyH-101.

FIG. 6B is a graph representing a paired analysis of experiments as in FIG. 6A showing PD changes (ΔPD) for the forskolin effect, forskolin and CFTR$_{inh}$-172, and forskolin and GlyH-101.

FIG. 6C is a graph illustrating of a change in PD (mean±SE) in a series of low Cl⁻ induced hyperpolarization experiments (left panel) or forskolin induced hyperpolarization (right panel) in which solutions contained either 4,4'-diisothiocyanostilbene-2,2'-disulfonic acid (DIDS) or GlyH-101 (*P<0.005 for reduced ΔPD compared to control).

Figure 7A:
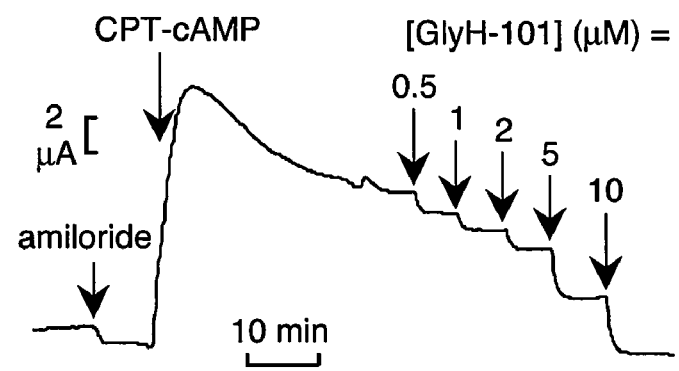
Figure 7A:
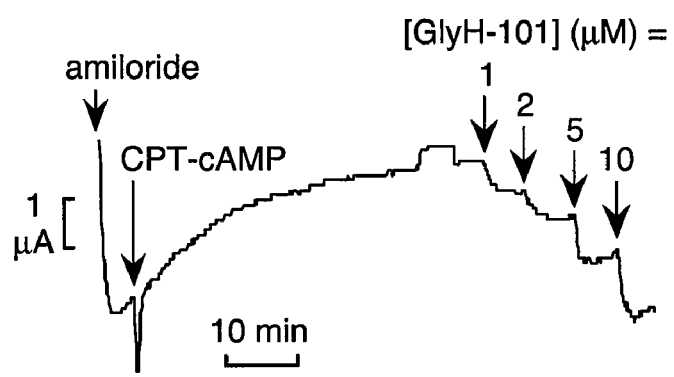
Figure 7A:
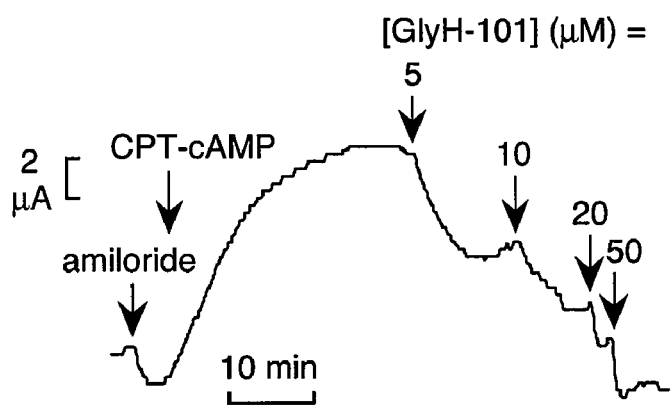

FIG. 7A is a graph illustrating GlyH-101 inhibition of short-circuit current after CFTR stimulation in T84 cells (top panel), human airway cells (middle panel), and isolated mouse ileum (bottom panel). Following constant baseline current, amiloride (10 μM, apical solution) and CPT-cAMP (0.1 mM, both solutions) were added, followed by indicated concentrations of GlyH-101 (both solutions).

FIG. 7B is a graph representing GlyH-101 inhibition of fluid secretion in a closed intestinal loop model of cholera toxin-induced fluid secretion. Intestinal lumenal fluid, shown as loop weight/length (gm/cm, SE, 6 mice), measured at 4 hours after injection of saline (control), cholera toxin (1 μg) or cholera toxin+GlyH-101 (0.25 μg).

Figure 8:
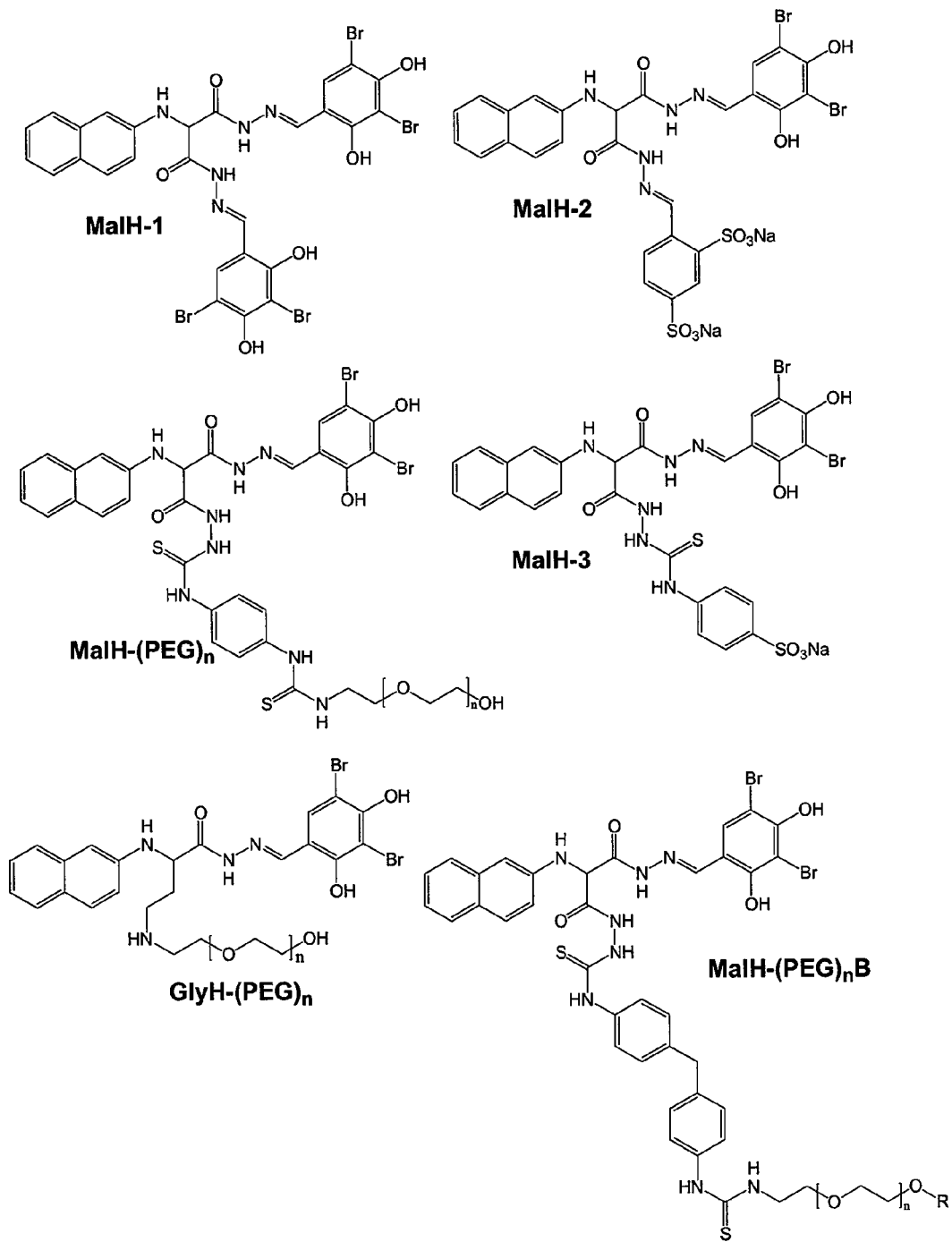

FIG. 8 provides chemical structures of a class of nonabsorbable molonic acid dihydrazide (denoted as MalH-x) analogs of glycine hydrazide compounds of the invention.

Figure 9:
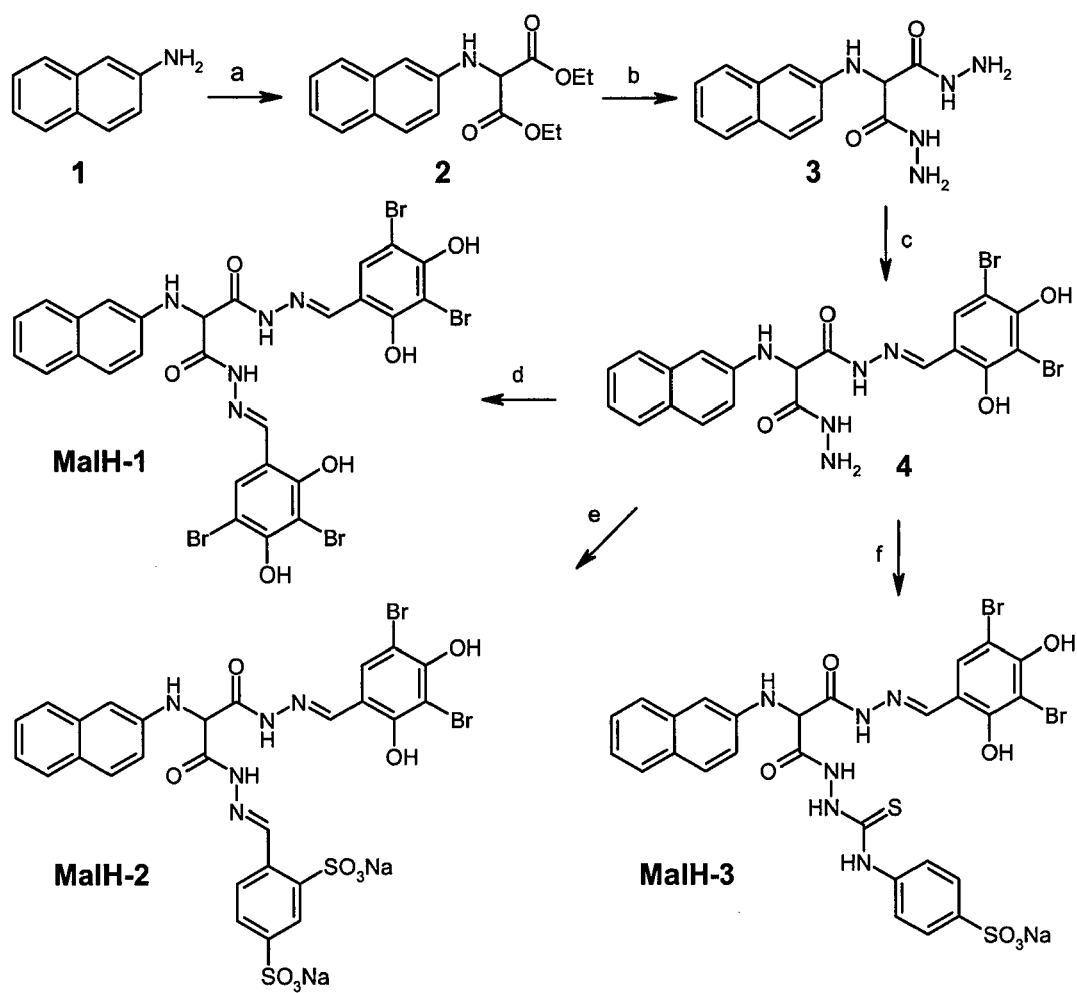

FIG. 9 depicts the reaction scheme for the synthesis of the polar non-absorbable CFTR inhibitors 2-naphthalenylamino-bis[(3,5-dibromo-2,4-dihydroxyphenyl)methylene]propanedioic acid dihydrazide (MalH-1), 2-naphthalenylamino-[(3,5-dibromo-2,4-dihydroxyphenyl)methylene][(2,4-disodium-disulfophenyl)methylene]propanedioic acid dihydrazide (MalH-2), and 2-naphthalenylamino-[(3,5-dibromo-2,4-dihydroxyphenyl)methylene][3-(4-sodium-sulfophenyl)-thioureido]propanedioic acid dihydrazide (MalH-3). Reagents and conditions: (a) diethyl bromomalonate, NaOAc, 90° C., 8 hours, 84%; (b) N$_2$H$_4$.H$_2$O, EtOH/reflux, 10 hours, 92%; (c), (d) 3,5-di-Br-2,4-di-OH-benzaldehyde (1 equivalent), EtOH/reflux, 3 hours, 58%; (e) 2,4-di-SO$_3$Na-benzaldehyde, DMF/reflux, 4 hours, 58%; and (f) 4-sodium-sulfophenyl-isothiocyante, DMF/reflux, 4 hours, 47%.

Figure 10:
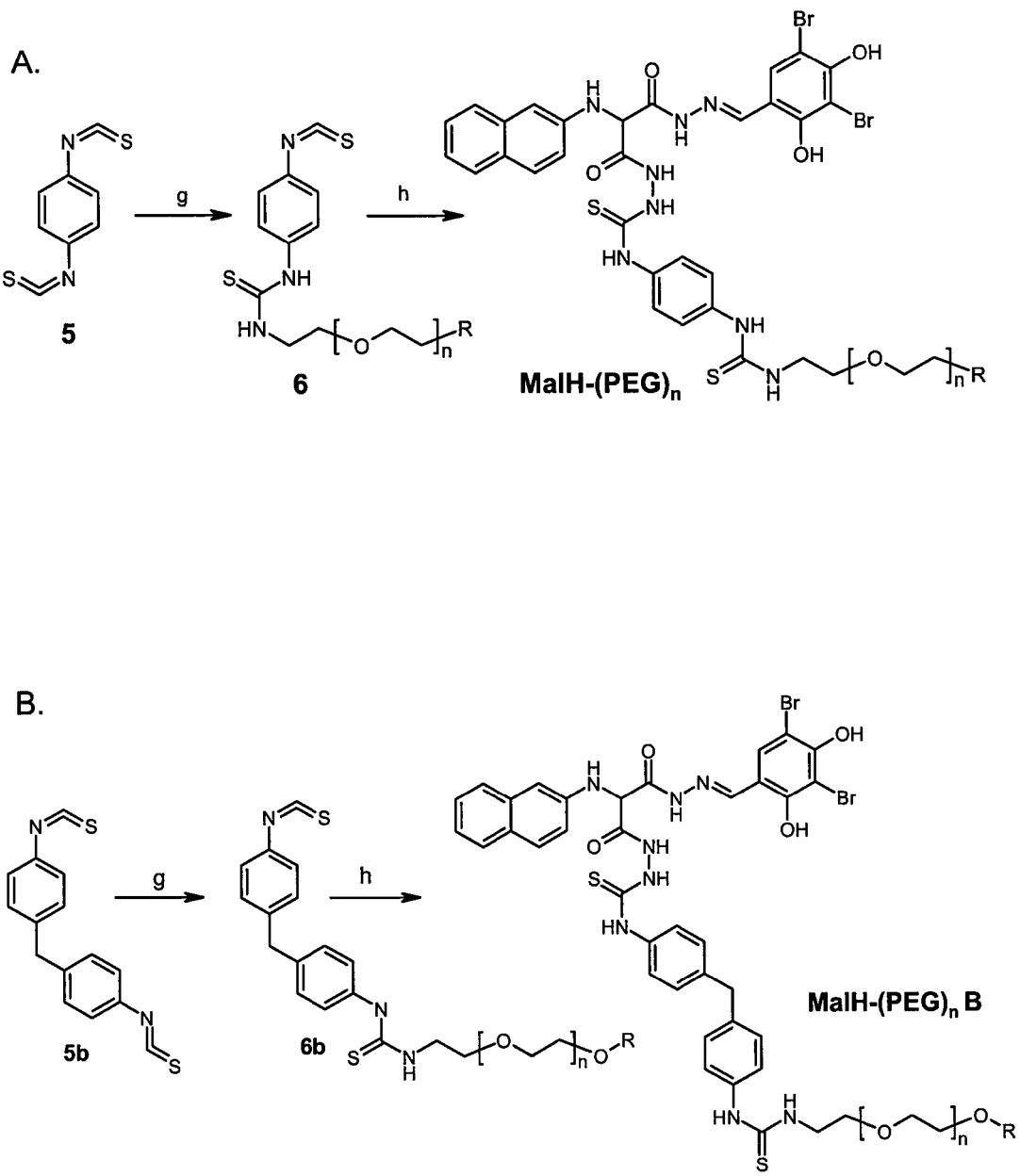

FIG. 10 depicts the reaction scheme for the synthesis of the PEG-ylated CFTR inhibitor MalH-(PEG)$_n$ (Panel A) and MalH-(PEG)$_n$B (Panel B).

Figure 11:
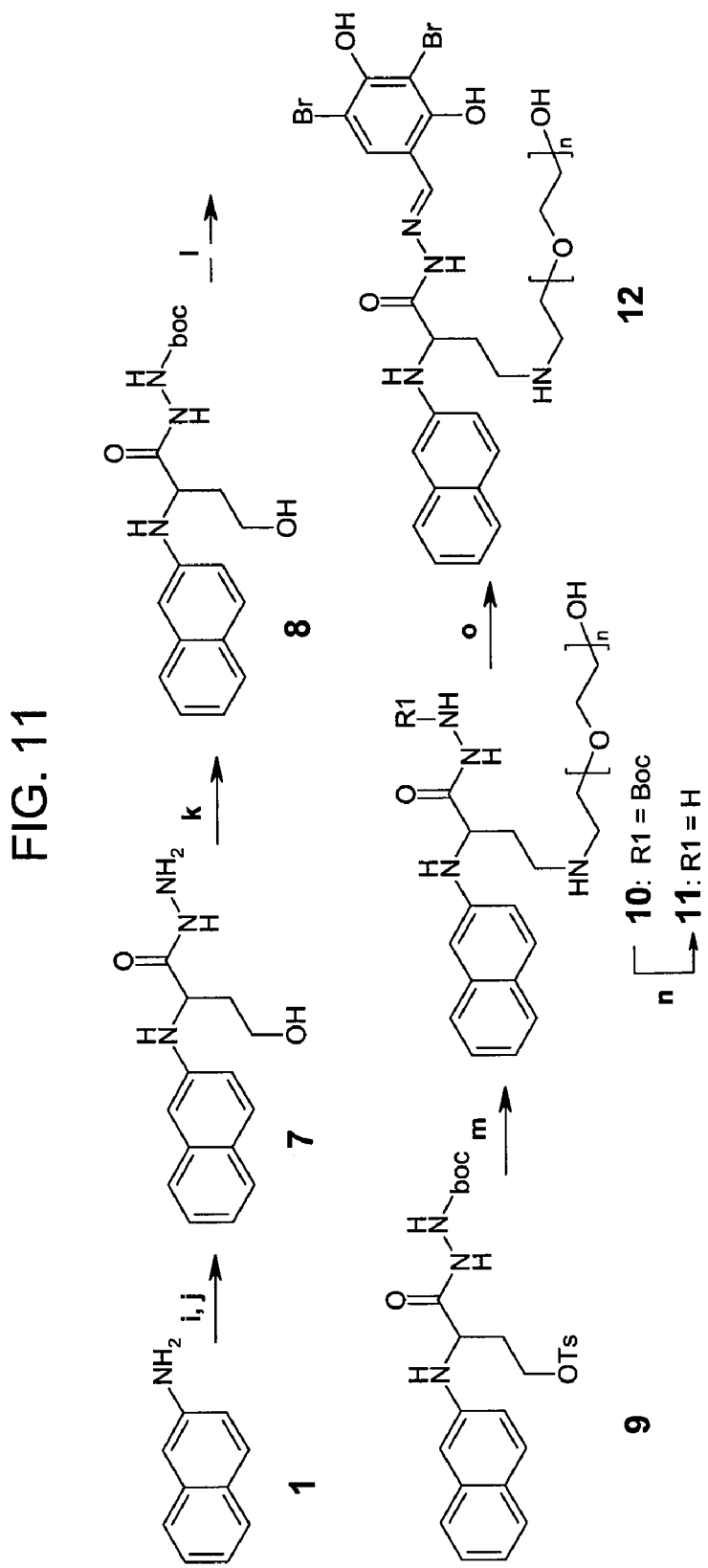

FIG. 11 depicts the reaction scheme for the synthesis of the PEG-ylated CFTR inhibitor GlyH-(PEG)$_n$. Reagents and conditions: (i) Br-buterolactone, NaOAc, 90° C., 8 hours, 89%; (j) N$_2$H$_4$.H$_2$O, EtOH/reflux, 10 hours, 89%; (k) (BOC)$_2$O, THF, rt, 86%; (l) TsCl, pyridine, −15° C., 8 hours, 73%; (m) NH$_2$-PEG, DMF, 80° C., 24 hours, 38%; (n) TFA, CH$_2$Cl$_2$, rt 30 min, 73%; and (o) 3,5-di-Br-2,4-di-OH-benzaldehyde, EtOH/reflux, 3 hours, 58%.

Figure 12:
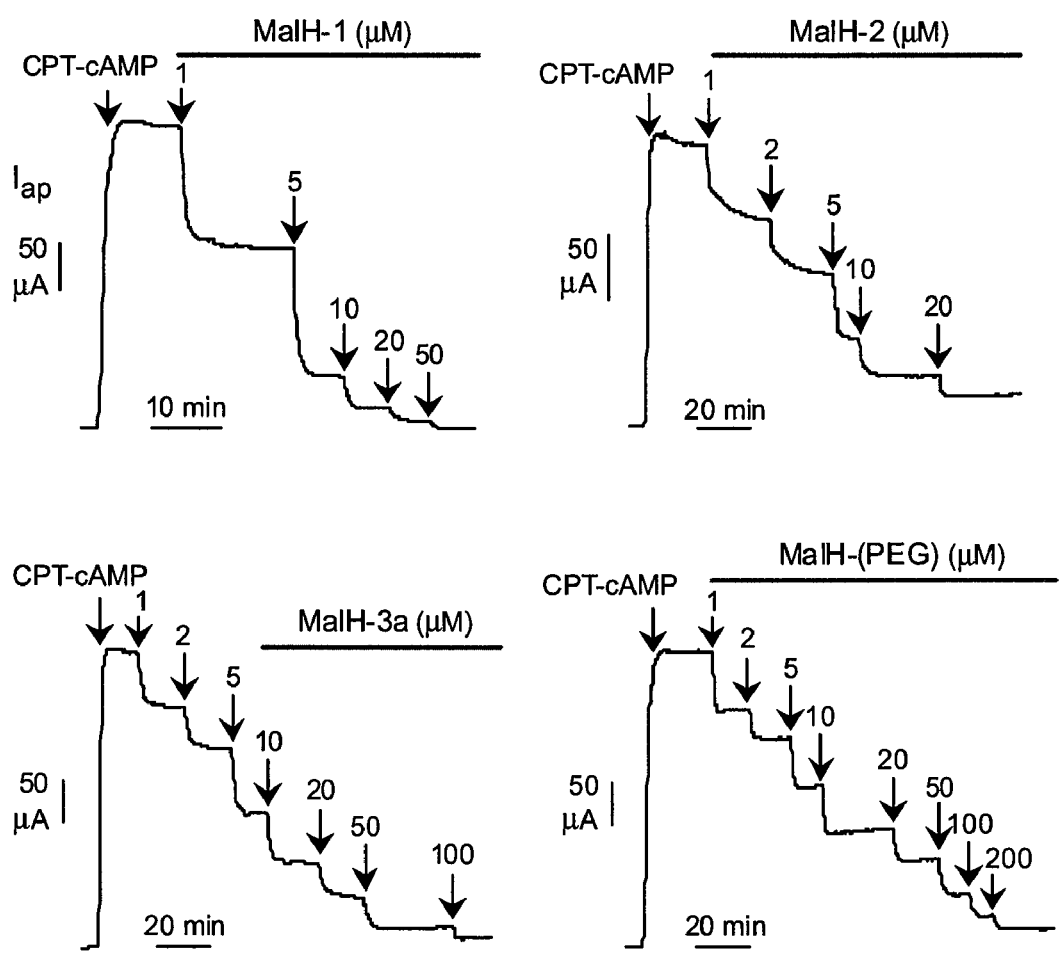

FIG. 12 is a series of graphs showing inhibition of apical membrane chloride current in FRT epithelial cells expressing human wildtype CFTR. Chloride current was measured by short-circuit current analysis in cells subjected to a chloride ion gradient and after permeabilization of the basolateral membrane. CFTR was stimulated by 100 μM CPT-cAMP. Increasing concentrations of MalH compounds were added as indicated.

Figure 13:
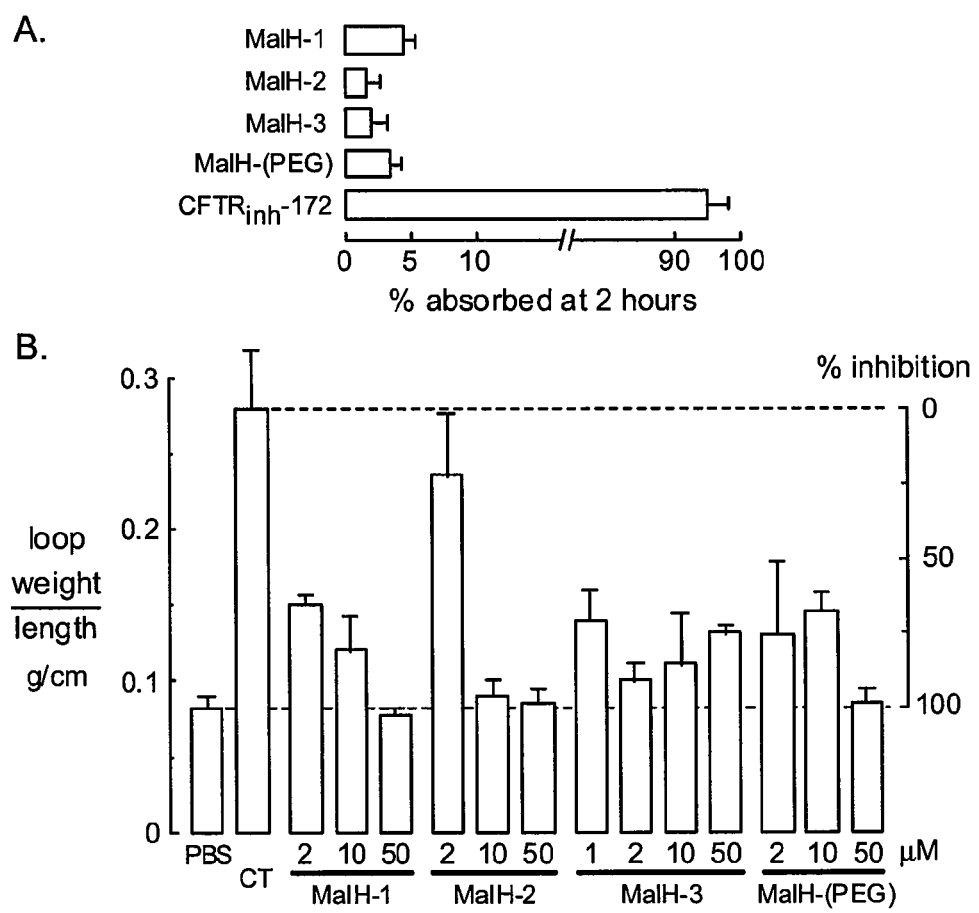

FIG. 13 is a series of graphs showing intestinal absorption and antidiarrheal efficacy of CFTR inhibitors. Panel A is a graph showing absorption over 2 hours of indicated MalH compounds in closed jejunal loops in living mice (SD, n=4-6 mice). For comparison absorption of $CFTR_{inh}$-172 show as measured by same method. Panel B is a graph showing inhibition of cholera toxin-induced fluid secretion in closed jejunal loops. Loops were injected with saline (PBS) or saline containing 1 µg cholera toxin (CT) with indicated amounts of MalH compounds. Loops weight-to-length ratio measured at 6 hours (SD, n=3-5 mice).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It should be noted that as used herein and in the appended claims, the singular forms "a", "and", and "the" include plural referents unless the context clearly dictates otherwise. Thus, for example, reference to "an inhibitor" includes a plurality of such inhibitors and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention is based on the discovery of hydrazide-containing compounds that are high-affinity CFTR inhibitors. The structure of these compounds having CFTR inhibitory activity disclosed herein, and derivatives thereof, as well as pharmaceutical formulations and methods of use are described in more detail below.

Definitions

A "cystic fibrosis transmembrane conductance regulator protein-mediated condition or symptom" or "CFTR-mediated condition or symptom" means any condition, disorder or disease, or symptom of such condition, disorder, or disease, that results from activity of cystic fibrosis transmembrane conductance regulator protein (CFTR), e.g., activity of CFTR in ion transport. Such conditions, disorders, diseases, or symptoms thereof are treatable by inhibition of CFTR activity, e.g., inhibition of CFTR ion transport. CFTR activity has been implicated in, for example, intestinal secretion in response to various agonists, including cholera toxin (see, e.g., Snyder et al. 1982 Bull. World Health Organ. 60:605-613; Chao et al. 1994 EMBO J. 13:1065-1072; Kimberg et al. 1971 J. Clin. Invest. 50:1218-1230).

A "CFTR inhibitor" as used herein is a compound that reduces the efficiency of ion transport by CFTR, particularly with respect to transport of chloride ions by CFTR. Preferably CFTR inhibitors of the invention are specific CFTR inhibitors, i.e., compounds that inhibit CFTR activity without significantly or adversely affecting activity of other ion transporters, e.g., other chloride transporters, potassium transporters, and the like. Preferably the CFTR inhibitors are high-affinity CFTR inhibitors, e.g., have an affinity for CFTR of at least about one micromolar, usually about one to five micromolar.

The term "isolated compound" means a compound which has been substantially separated from, or enriched relative to, other compounds with which it occurs in nature. Preferably, the compound is at least about 80%, more preferably at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof.

"Treating" or "treatment" as used herein covers the treatment of a disease, condition, disorder or symptom in a subject, wherein the disease, condition, disorder or symptom is mediated by the activity of CFTR, and includes: (1) preventing the disease, condition, or disorder, i.e. causing the clinical symptoms of the disease not to develop in a subject that may be exposed to or predisposed to the disease, condition, or disorder, but does not yet experience or display symptoms thereof, (2) inhibiting the disease, condition or disorder, i.e., arresting or reducing the development of the disease, condition or disorder, or its clinical symptoms, or (3) relieving the disease, condition or disorder, i.e., causing regression of the disease, condition or disorder, or its clinical symptoms.

A "therapeutically effective amount" or "efficacious amount" means the amount of a compound of the invention that, when administered to a mammal or other subject in need thereof, is sufficient to effect treatment, as defined above, for diseases, conditions, disorders or symptoms mediated by the activity of CFTR. The amount of a compound of the invention that constitutes a "therapeutically effective amount" will vary depending on the compound, the disease and its severity and the age, weight, etc., of the subject to be treated, but can be determined routinely by one of ordinary skill in the art having regard to his own knowledge and to this disclosure.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines;

felines; equines; bovines; ovines; rodentia, etc. and primates, particularly humans. Non-human animal models, particularly mammals, e.g., primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject. Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound of the invention means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

A "pro-drug" means any compound that releases an active parent compound of formula (I) in vivo when the prodrug is administered to a mammalian subject. Prodrugs of the compounds of formula (I) contain functional groups that, under standard physiological conditions, are hydrolyzed into the corresponding carboxy, hydroxy, or amino group. Examples of such functional groups include, but are not limited to, esters (e.g., acetate, formate and benzoate derivatives) and carbamates (e.g., N,N-dimethylaminocarbonyl) of hydroxy groups in compounds of formula (I), and the like. Additional examples include dipeptide or tripeptide esters of hydroxy or carboxy groups in compounds of formula (I), and the like. The preparation of such functional groups is well known in the art. For example, a compound of formula (I) having a hydroxy group attached thereto may be treated with a carboxylic acid or a dipeptide having a free carboxy terminus under esterification conditions well known in the art to yield the desired ester functional group. Likewise, a compound of formula (I) having a free carboxy group attached thereto may be treated with an alcohol or a tripeptide containing a hydroxy group such as a serine residue (e.g., —N(H)—C(H)(CH$_2$OH)—C(O)—) under esterification conditions well known in the art to produce the desired ester functional group. In addition, compounds of formula (I) having a carboxylic ester group attached thereto may be treated with a different carboxylic ester under standard transesterification conditions to produce compounds of formula (I) with the desired functional ester group attached thereto. All such functional groups are considered to be within the scope of this invention.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, n-octyl, dodecyl, octadecyl, amyl, 2-ethylhexyl, and the like. Suitable substituents include carboxy, protected carboxy, amino, protected amino, halo, hydroxy, protected hydroxy, mercapto, lower alkylthio, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, mercapto, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, mercapto, alkylthio, alkylsulfonyl, halo, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo group" or "halogen" are used interchangeably herein and refer to the fluoro, chloro, bromo or iodo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans-decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, mercapto, alkylthio, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2-, 3- or 4-chlorophenyl, 2,6-dichlorophenyl, 2,5-dichlorophenyl, 3,4-dichlorophenyl, 2-, 3- or 4-bromophenyl, 3,4-dibromophenyl, 3-chloro-4-fluorophenyl, 2-, 3- or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2-, 3- or 4-nitrophenyl; a cyanophenyl group, for example, 2-, 3- or 4-cyanophenyl; a mono- or di(alkyl)phenyl group such as 2-, 3- or 4-methylphenyl, 2,4-dimethylphenyl, 2-, 3- or 4-(iso-propyl)phenyl, 2-, 3- or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy)phenyl, 3-ethoxy-4-methoxyphenyl and the like; a mono- or di(halo)-, mono-, di- or tri-(hydroxyl)phenyl such as 3,5-dibromo-2,4,6-trihydroxyphenyl 3,5-dibromo-2,4-dihydroxyphenyl, 3,5-dibromo-4-hydroxyphenyl, and 3-bromo-4-hydroxyphenyl and the like; a mono- or di(halo)-mono- or di-(hydroxyl)-mono- or di-(alkoxy)phenyl such as 3,5-dibromo-2-hydroxyl-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl)phenyl or 2,4-(protected aminomethyl)phenyl; or a mono- or di(N-(methylsulfonylamino))phenyl such as 2-, 3- or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples include such groups as 2-phenyl-1-chloroethyl, 2-(4'-methoxyphenyl)ethyl, 4-(2',6'-dihydroxy phenyl)-n-hexyl, 2-(5'-cyano-3'-methoxyphenyl)-n-pentyl, 3-(2',6'-dimethylphenyl)propyl, 4-chloro-3-aminobenzyl, 6-(4'-methoxyphenyl)-3-carboxyhexyl, 5-(4'-aminomethylphenyl)-3-(aminomethyl)pentyl, 5-phenyl-3-oxopent-1-yl, (4-hydroxynapth-2-yl)methyl and the like.

As noted above, the term "aromatic" or "aryl" refers to five and six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. These five-membered or six-membered rings may be fully unsaturated.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, mercapto, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or disubstituted with an alkyl group" means that the alkyl may, but need not, be present, and the description includes situations where the heterocyclo group is mono- or disubstituted with an alkyl group and situations where the heterocyclo group is not substituted with the alkyl group.

The term "electron-withdrawing group" refers to the ability of a functional group on a molecule to draw electrons to itself more than a hydrogen atom would if the hydrogen atom occupied the same position in the molecule. Examples of electron-withdrawing groups include, but are not limited to, halogen groups, —C(O)R groups (where R is alkyl); carboxylic acid and ester groups; —NR3+ groups (where R is alkyl or hydrogen); azo; nitro; —OR and —SR groups (where R is hydrogen or alkyl); and organic groups (as defined herein) containing such electron-withdrawing groups, such as haloalkyl groups (including perhaloalkyl groups), and the like.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture of thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Overview

Figure 1A:
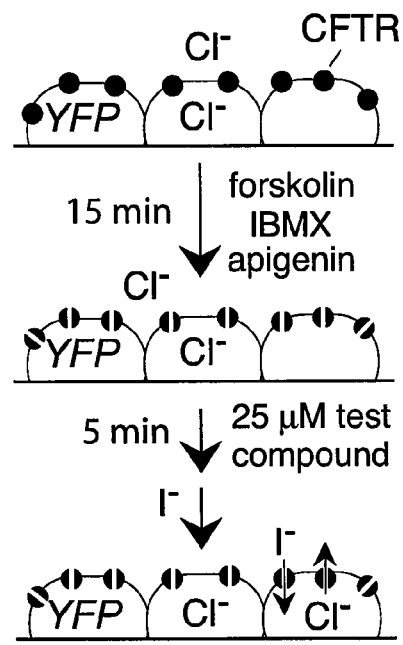
FIG. 1B shows chemical structures of CFTR inhibitors identified by the screening technique of FIG. 1A.
FIG. 1C is a graph representing relative fluorescence versus time using the screening technique of FIG. 1A for the CFTR inhibitor N-2-napthalenyl-[(3,5-dibromo-2,4-dihydroxyphenyl)methylene]glycine hydrazide (referred to herein as GlyH-101) at several concentrations.
FIG. 1D is a graph representing GlyH-101 inhibition of short-circuit current in permeabilized FRT cells expressing human CFTR. CFTR was stimulated by 100 μM CPT-cAMP.
Figure 1B:
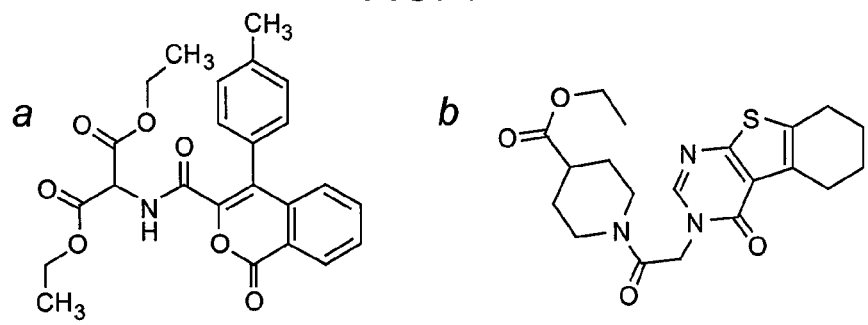
Figure 1B:
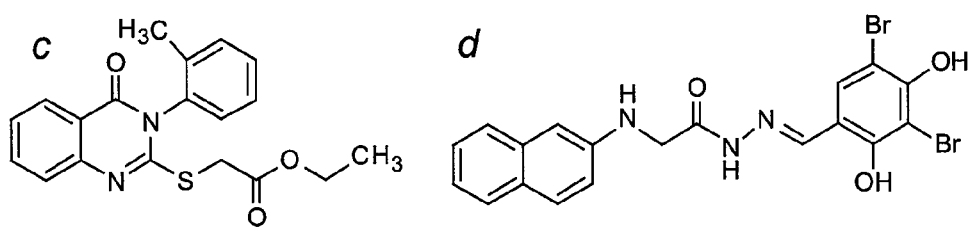

The invention provides hydrazide-containing compounds, derivative compositions and methods of their use in high affinity inhibition of cystic fibrosis transmembrane conductance regulator protein (CFTR) and for the study and treatment of CFTR-mediated diseases and conditions. The discovery of the subject hydrazide-containing compounds and derivatives was based on screening of numerous potential candidate compounds using an assay designed to identify CFTR inhibitors that interact directly with CFTR. Without being held to any particular theory or mode of operation, since multiple CFTR activators that work on different activating pathways were included in the studies leading to identification of the subject compounds, the inhibitory compounds of the invention likely effect inhibition by acting at or near the CFTR Cl⁻ transporting pathway. A screening of 100,000 diverse compounds identified several compounds and derivatives as effective CFTR inhibitors (FIG. 1B). These compounds and derivatives are unrelated chemically and structurally to previously known CFTR activators or to the previously known CFTR inhibitors DPC, NPPB glibenclamide, or thiazolidinone. The most potent CFTR inhibitor identified from screening had a $K_I$ of ~2 μM for inhibition of Cl⁻ current in human airway cells. Inhibition was rapid, reversible and CFTR-specific.

The compositions and methods of the invention will now be described in more detail.

Hydrazide-Containing Compounds

The hydrazide-containing compounds described herein comprise an aromatic- or heteroaromatic-substituted nitrogen, a hydrazide (which can be a glycine or oxamic hydrazide), and a substituted or substituted aryl group. In specific embodiments, the subject compounds are generally described by Formula (I) as follows:

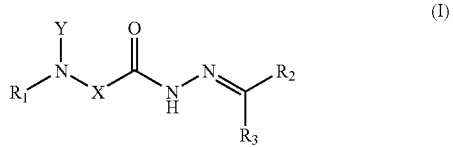

(I)

wherein X is independently chosen from an alkyl group, or a carbonyl group; Y is independently chosen from an alky group; an alkyl group having polar substitutions, such as a sulfo group, or a carboxyl group, or a linker, such as an amide bond or an ether linker to provide for attachment of one or more larger polar molecules, such as a polyoxyalkyl polyether (such as a polyethylene glycol (PEG), polypropylene glycol, polyhydroxyethyl glycerol), disaccharides, a substituted or unsubstituted phenyl group, polyalkylimines, a dendrimer from 0-10 generation and the like, where Y can further include such an attached polar molecule(s); $R_1$ is independently chosen from a substituted or unsubstituted phenyl group, a substituted or unsubstituted heteroaromatic group such as a substituted or unsubstituted quinolinyl group, an substituted or unsubstituted anthracenyl group, and a substituted or unsubstituted naphthalenyl group; $R_2$ is a substituted or unsubstituted phenyl group; and $R_3$ is independently chosen from hydrogen and an alkyl group; or a pharmaceutically acceptable derivative thereof, as an individual stereoisomer or a mixture thereof. In one embodiment, $R_1$ is chosen from a substituted phenyl group, an unsubstituted quinolinyl group, an unsubstituted anthracenyl group, and an unsubstituted naphthalenyl group; $R_2$ is a substituted phenyl group; and $R_3$ is independently chosen from hydrogen and an alkyl group. Exemplary substituents for $R_1$, $R_2$, and $R_3$, are described in more detail below.

In certain embodiments, the hydrazide-containing compounds are generally described by Formula (I), wherein X is an alkyl group. Such compounds are generally described by Formula (Ia) as follows:

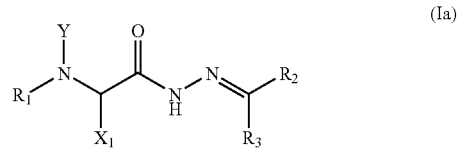

(Ia)

wherein Y is a hydrogen or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $X_1$ is independently chosen from a hydrogen or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an alkyl group comprising a polar molecule chosen from a sulfo group, a carboxy group, a carboxamide group, a polyoxyalkyl polyether, a disaccharide, a substitute or unsubstituted phenyl group, or a polyethylene imine (PEI), or a dendrimer from 0-10 generation; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group. In some embodiments, when $X_1$ is hydrogen, $R_1$ is a substituted or unsubstituted anthracenyl group, or a heteroaromatic group. In still other embodiments, when $X_1$ is hydrogen, Y is not hydrogen.

In specific embodiments, $R_1$ is independently chosen from a mono-(halo)phenyl group such as 2-, 3-, or 4-chlorophenyl; a mono-(alkyl)phenyl such as a 2-, 3-, or 4-methylphenyl; a naphthalenyl group such as 1- or 2-naphthalenyl; a mono- or di(halo)naphthalenyl, such as 1-, 3-, 4-, 5-, 6-, 7-, or 8-chloronaphthalenyl, 3,4- or 5,6- or 5,7- or 5,8-dichloronaphthalenyl; a mono- or di(hydroxy)naphthalenyl, such as 1-, 3-, 4-, 5-, 6-, 7-, or 8-hydroxynaphthalenyl, 1,8-, 3,4-, dihydroxynaphthalenyl; a mono- or di or tri(alkoxy)naphthalenyl, such as 1-, 3-, 5-, 6-, 7-, or 8-methoxynaphthalenyl, 5,8-dimethoxynaphthalenyl, 1,4,8-trimethoxynaphthalenyl; a mono- or di(alkyl)naphthalenyl, such as 1-, 3-, 4-, 5-, or 6-methylnaphthalenyl, 4,5-, 4,6-dimethynaphthalenyl; a mono-(hydroxy)-mono or di(sulfo)naphthalenyl such as 4-hydroxy-2-sulfonaphthalenyl, 8-hydroxy-3,6-disulfo-naphthalenyl; mono (alkyl)-mono- or di(alkoxy)naphthalenyl, such as 1methyl-5,6-dimethoxynaphthalenyl; or a quinolinyl group such as 6-quinolynyl; $R_2$ is independently chosen from the group consisting of substituted phenyl groups such as: a mono-(halo)phenyl group such as 2-, 3-, or 4-bromophenyl; a mono or di(hydroxyl)phenyl group such as 2,3,4-hydroxyphenyl and 2,4-dihydroxyphenyl; a mono- or di(halo)-mono-, di-, or tri-(hydroxyl)phenyl such as 3,5-dibromo-2,4,6-trihydroxyphenyl, 3,5-dibromo-2,4-dihydroxyphenyl, 3,5-dibromo-4-hydroxyphenyl, and 3-bromo-4-hydroxyphenyl; a mono- or di(halo)-mono- or di-(hydroxyl)-mono- or di-(alkoxy)phenyl such as 3,5-dibromo-2-hydroxy-4-methoxyphenyl; and $R_3$ is independently chosen from hydrogen or an alkyl group.

In further embodiments, the hydrazide-containing compounds and derivatives of Formula (Ia) may comprise of compounds, wherein Y is a hydrogen; X is a hydrogen, methyl or ethyl group; $R_1$ is independently chosen from a mono-(halo)phenyl group, such as a 2-, 3-, or 4-chlorophenyl group, a naphthalenyl group, such as a 2-naphthalenyl or a 1-naphthalenyl; $R_2$ is independently chosen from a di-(halo)-mono- or di(hydroxyl)phenyl group such as a 3,5-di-bromo-2,4-dihydroxyphenyl group, 3,5-di-bromo-4-hydroxyphenyl group; and $R_3$ is a hydrogen or a methyl group.

In other embodiments, the hydrazide-containing compounds are generally described by Formula (I) wherein X is $CH_2$. Such compounds are generally described by Formula (Ib) as follows:

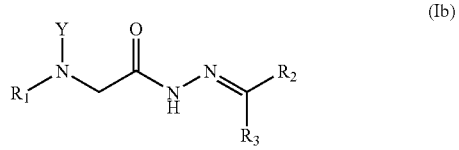

(Ib)

wherein Y is a hydrogen or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group.

In some embodiments, Y is an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; and $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group.

In specific embodiments, $R_1$ is independently chosen from a mono-(halo)phenyl group such as 2-, 3-, or 4-chlorophenyl; a mono-(alkyl)phenyl such as a 2-, 3-, or 4-methylphenyl; a naphthalenyl group such as 1- or 2-naphthalenyl; a mono- or di(halo)naphthalenyl, such as 1-, 3-, 4-, 5-, 6-, 7-, or 8-chloronaphthalenyl, 3,4- or 5,6- or 5,7- or 5,8-dichloronaphthalenyl; a mono- or di(hydroxy)naphthalenyl, such as 1-, 3-, 4-, 5-, 6-, 7-, or 8-hydroxynaphthalenyl, 1,8-, 3,4-, dihydroxynaphthalenyl; a mono- or di or tri(alkoxy)naphthalenyl, such as 1-, 3-, 5-, 6-, 7-, or 8-methoxynaphthalenyl, 5,8-dimethoxynaphthalenyl, 1,4,8-trimethoxynaphthalenyl; a mono- or di(alkyl)naphthalenyl, such as 1-, 3-, 4-, 5-, or 6-methylnaphthalenyl, 4,5-, 4,6-dimethynaphthalenyl; a mono-(hydroxy)-mono or di(sulfo)naphthalenyl such as 4-hydroxy-2-sulfonaphthalenyl, 8-hydroxy-3,6-disulfo-naphthalenyl; mono (alkyl)-mono- or di(alkoxy)naphthalenyl, such as 1methyl-5,6-dimethoxynaphthalenyl; or a quinolinyl group such as 6-quinolynyl; $R_2$ is independently chosen from the group consisting of substituted phenyl groups such as: a mono-(halo)phenyl group such as 2-, 3-, or 4-bromophenyl; a mono or di(hydroxyl)phenyl group such as 2,3,4-hydroxyphenyl and 2,4-dihydroxyphenyl; a mono- or di(halo)-, di-, or tri-(hydroxyl)phenyl such as 3,5-dibromo-2,4,6-trihydroxyphenyl, 3,5-dibromo-2,4-dihydroxyphenyl, 3,5-dibromo-4-hydroxyphenyl, and 3-bromo-4-hydroxyphenyl; a mono- or di(halo)-mono- or di-(hydroxyl)-mono- or di-(alkoxy)phenyl such as 3,5-dibromo-2-hydroxy-4-methoxyphenyl; and $R_3$ is independently chosen from hydrogen or an alkyl group. Compounds described by Formula (Ib) are generally described as glycine hydrazides.

In further embodiments, the hydrazide-containing compounds and derivatives of Formula (Ib) may comprise of compounds, wherein Y is a hydrogen; $R_1$ is independently chosen from a mono-(halo)phenyl group, such as a 2-, 3-, or 4-chlorophenyl group, a naphthalenyl group, such as a 2-naphthalenyl or a 1-naphthalenyl; $R_2$ is independently chosen from a di-(halo)-mono- or di(hydroxyl)phenyl group such as a 3,5-di-bromo-2,4-di-hydroxyphenyl group, 3,5-di-bromo-4-hydroxyphenyl group; and $R_3$ is a hydrogen or a methyl group.

In yet other embodiments, the hydrazide-containing compounds are generally described by Formula (I) wherein X is a carbonyl. Such compounds are generally described by Formula (Ic) as follows:

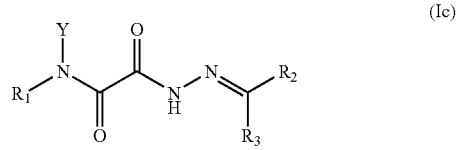

(Ic)

wherein Y is a hydrogen or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group.

In some embodiments, Y is an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group.

In specific embodiments, $R_1$ is independently chosen from a mono-(halo)phenyl group such as 2-, 3-, or 4-chlorophenyl; a mono-(alkyl)phenyl such as a 2-, 3-, or 4-methylphenyl; a naphthalenyl group such as 1- or 2-naphthalenyl; a mono- or di(halo)naphthalenyl, such as 1-, 3-, 4-, 5-, 6-, 7-, or 8-chloronaphthalenyl, 3,4- or 5,6- or 5,7- or 5,8-dichloronaphthalenyl; a mono- or di(hydroxy)naphthalenyl, such as 1-, 3-, 4-, 5-, 6-, 7-, or 8-hydroxynaphthalenyl, 1,8-, 3,4-, dihydroxynaphthalenyl; a mono- or di or tri(alkoxy)naphthalenyl, such as 1-, 3-, 5-, 6-, 7-, or 8-methoxynaphthalenyl, 5,8-dimethoxynaphthalenyl, 1,4,8-trimethoxynaphthalenyl; a mono- or di(alkyl)naphthalenyl, such as 1-, 3-, 4-, 5-, or 6-methylnaphthalenyl, 4,5-, 4,6-dimethynaphthalenyl; a mono-(hydroxy)-mono or di(sulfo)naphthalenyl such as 4-hydroxy-2-sulfonaphthalenyl, 8-hydroxy-3,6-disulfo-naphthalenyl; mono (alkyl)-mono- or di(alkoxy)naphthalenyl, such as 1methyl-5,6-dimethoxynaphthalenyl; or a quinolinyl group such as 6-quinolynyl; $R_2$ is independently chosen from the group consisting of substituted phenyl groups such as: a mono-(halo)phenyl group such as 2-, 3-, or 4-bromophenyl; a mono or di(hydroxyl)phenyl group such as 2,3,4-hydroxyphenyl and 2,4-dihydroxyphenyl; a mono- or di(halo)-mono-, di-, or tri-(hydroxyl)phenyl such as 3,5-dibromo-2,4,6-trihydroxyphenyl, 3,5-dibromo-2,4-dihydroxyphenyl, 3,5-dibromo-4-hydroxyphenyl, and 3-bromo-4-hydroxyphenyl; a mono- or di(halo)-mono- or di-(hydroxyl)-mono- or di-(alkoxy)phenyl such as 3,5-dibromo-2-hydroxy-4-methoxyphenyl; and $R_3$ is independently chosen from hydrogen or an alkyl group. Compounds described by Formula (Ic) are generally described as oxamic acid hydrazides.

In further embodiments, the hydrazide-containing compounds and derivatives of Formula (Ic) may comprise of compounds, wherein Y is hydrogen; $R_1$ is a naphthalenyl group, such as a 2-naphthalenyl or a 1-naphthalenyl; $R_2$ is a di-(halo)-mono- or di(hydroxyl)phenyl group such as a 3,5-di-bromo-2,4-di-hydroxyphenyl group, 3,5-di-bromo-4-hydroxyphenyl group; and $R_3$ is a hydrogen or a methyl group.

In some embodiments of the invention, the hydrazide-containing compound may comprise a formula of the following:

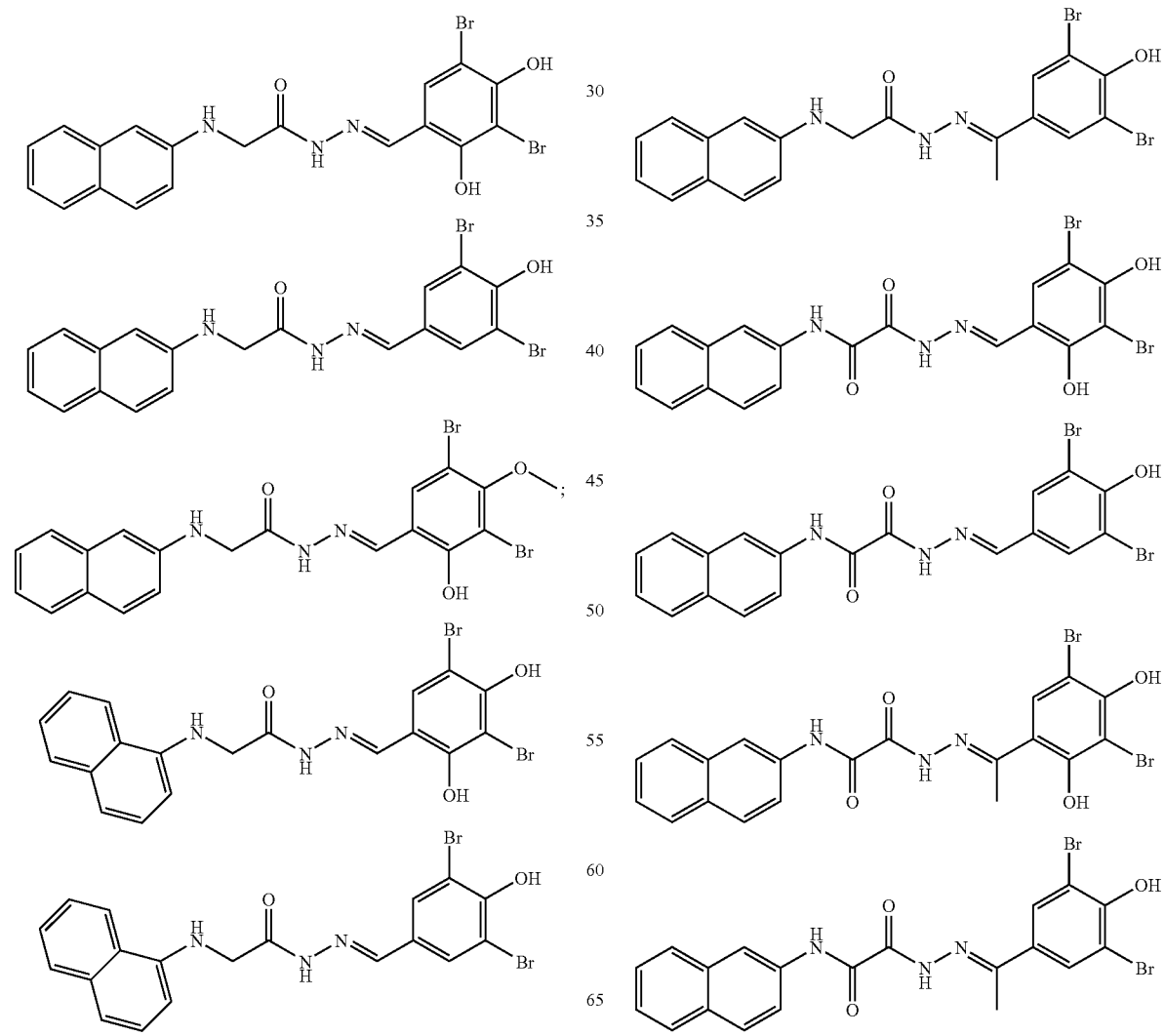

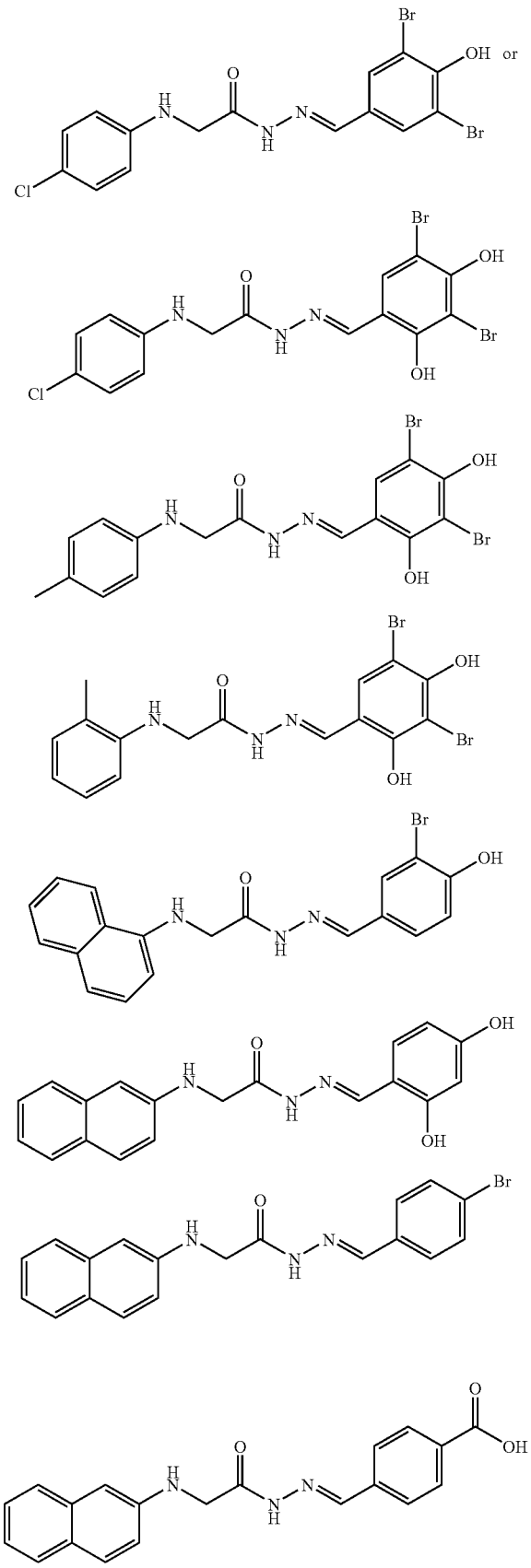

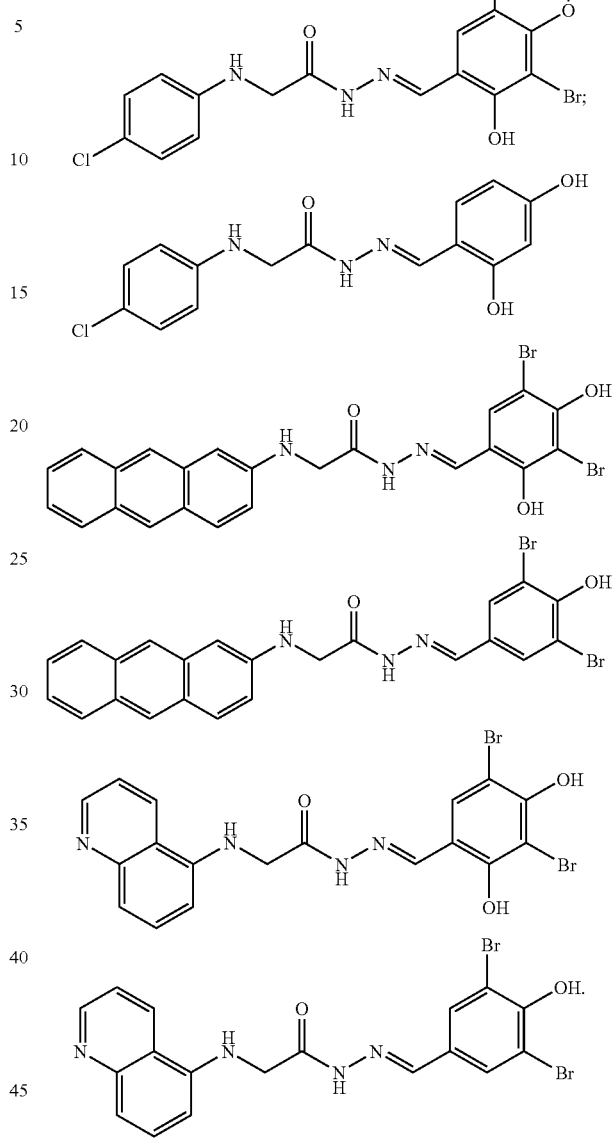

The hydrazide-containing compounds described herein may be modified, for example, to provide for a desired characteristic. Preferably, modification of the compounds does not significantly or undesirably adversely affect the desirable characteristics of the hydrazide-containing compounds, e.g., ability to inhibit CFTR function and water solubility of the compound. For example, the compounds described herein can be modified so as decrease the ability of the compound to cross a cell membrane, e.g., a cell membrane of a cell lining a mucosal surface, e.g., a gastrointestinal cell. Membrane impermeance of the compounds disclosed herein can be increased by, for example, increasing the size or other physical characteristics of the compound.

In such embodiments, the membrane permeability of the compounds generally described by Formula I, are decreased by the addition of polar groups, such as sulfo and alkyl-carboxyl groups. Such compounds are generally described by Formula (I) as follows:

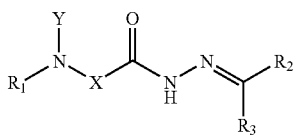

(I)

wherein Y is independently chosen from an alky group; an alkyl group having polar substitutions, such as a sulfo group, or a carboxyl group; or a linker, such as an amide bond or an ether linker to provide for attachment of one or more larger polar molecules, such as a polyoxyalkyl polyether (such as a polyethylene glycol (PEG), polypropylene glycol, polyhydroxyethyl glycerol), disaccharides, polyalkylimines, and the like, where Y can further include such an attached polar molecule(s); X is independently chosen from an alkyl group, or a carbonyl group; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; and $R_3$ is independently chosen from hydrogen and an alkyl group.

In specific embodiments Y is independently chosen from a substituted or unsubstituted alkyl group, such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an alkyl group carrying polar groups such as hydroxy, sulfo, carboxylate, or a substituted or unsubstituted carboxamide groups (where exemplary groups include 3-sulfopropyl, 4-sulfobutyl, carboxymethyl, 2-carboxypropyl, 2-methoxy-2-oxoethyl, 3-methoxy-3-oxopropyl); or a linker such as an amide bond or ether linker to provide for attachment of one or more larger polar molecules, such as a polyoxyalkyl polyether (such as polyethylene glycol (PEG), polypropylene glycol, polyhydroxyethyl glycerol), polyethyleneimines, disaccharides, trisaccharides, polyalkylimines, small amino dextrans and the like, where Y can further include such an attached polar molecule(s).

In some embodiments, the nitrogen of the unsaturated amide bond of the compound may be substituted as exemplified below:

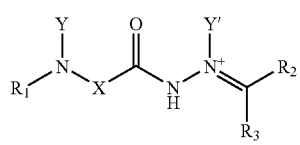

(Id)

wherein X is independently chosen from an alkyl group, or a carbonyl group; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; $R_3$ is independently chosen from hydrogen and an alkyl group; and Y' is independently chosen from an substituted or unsubstituted alkyl group, such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an alkyl group carrying polar groups such as hydroxy, sulfo, carboxylate, and a substituted or unsubstituted carboxamide groups (where exemplary groups include, such as 3-sulfopropyl, 4-sulfobutyl, carboxymethyl, 2-carboxypropyl, 2-methoxy-2-oxoethyl, 3-methoxy-3-oxoproplyl); or a linker such as an amide bond or ether linker to provide for attachment of one or more to larger polar molecules, such as a polyoxyalkyl polyether (such as polyethylene glycol (PEG), polypropylene glycol, polyhydroxyethyl glycerol), polyethyleneimines, disaccharides, trisaccharides, polyalkylimines, small amino dextrans and the like, where Y' can further include such an attached polar molecule(s).

In some embodiments, X is independently chosen from a carbonyl group; an alkyl group, such as a substituted or unsubstituted, saturated linear or branched hydrocarbon group or chain (e.g., $C_1$ to $C_8$) including, methylene, substituted alkyl groups, such as propene; substituted or unsubstituted phenyl groups, such as a phenyl group carrying polar groups; or a linker to carry polar groups; $R_1$ is independently chosen from a mono-(halo)phenyl group such as 2-, 3-, or 4-chlorophenyl; a mono-(alkyl)phenyl such as a 2-, 3-, or 4-methylphenyl; a naphthalenyl group such as 1- or 2-naphthalenyl; a mono- or di(halo)naphthalenyl, such as 1-, 3-, 4-, 5-, 6-, 7-, or 8-chloronaphthalenyl, 3,4- or 5,6- or 5,7- or 5,8-dichloronaphthalenyl; a mono- or di(hydroxy)naphthalenyl, such as 1-, 3-, 4-, 5-, 6-, 7-, or 8-hydroxynaphthalenyl, 1,8-, 3,4-, dihydroxynaphthalenyl; a mono- or di or tri(alkoxy)naphthalenyl, such as 1-, 3-, 5-, 6-, 7-, or 8-methoxynaphthalenyl, 5,8-dimethoxynaphthalenyl, 1,4,8-trimethoxynaphthalenyl; a mono- or di(alkyl)naphthalenyl, such as 1-, 3-, 4-, 5-, or 6-methylnaphthalenyl, 4,5-, 4,6-dimethynaphthalenyl; a mono-(hydroxy)-mono or di(sulfo)naphthalenyl such as 4-hydroxy-2-sulfo-naphthalenyl, 8-hydroxy-3,6-disulfo-naphthalenyl; mono(alkyl)-mono- or di(alkoxy)naphthalenyl, such as 1methyl-5,6-dimethoxynaphthalenyl; or a quinolinyl group such as 6-quinolynyl; $R_2$ is independently chosen from the group consisting of substituted phenyl groups such as a mono-(halo)phenyl group such as 2-, 3-, or 4-bromophenyl; a mono or di(hydroxyl)phenyl group such as 2,3,4-hydroxyphenyl and 2,4-dihydroxyphenyl; a mono- or di(halo)-mono- or di- or tri-(hydroxyl)phenyl such as 3,5-dibromo-2,4,6-trihydroxyphenyl, 3,5-dibromo-2,4-dihydroxyphenyl, 3,5-dibromo-4-hydroxyphenyl, and 3-bromo-4-hydroxyphenyl; a mono- or di(halo)-mono- or di-(hydroxyl)-mono- or di-(alkoxy)phenyl such as 3,5-dibromo-2-hydroxy-4-methoxyphenyl; and $R_3$ is independently chosen from hydrogen or an alkyl group.

In some embodiments, X of the compound may be substituted as exemplified below:

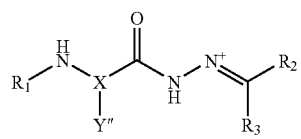

(Ie)

wherein X is an alkyl group; $R_1$ is independently chosen from a substituted or unsubstituted phenyl group, a substituted or unsubstituted heteroaromatic group such as a quinolinyl group, a substituted or unsubstituted anthracenyl group, and a substituted or unsubstituted naphthalenyl group; $R_2$ is a substituted or unsubstituted phenyl group; $R_3$ is independently chosen from hydrogen and an alkyl group; and Y" is independently chosen from an substituted or unsubstituted alkyl group, such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an alkyl group carrying polar groups such as hydroxy, sulfo, carboxylate, and a substituted or unsubstituted carboxamide groups (where exemplary groups include, such as 3-sulfopropyl, 4-sulfobutyl, carboxymethyl, 2-carboxypropyl, 2-methoxy-2-oxoethyl, 3-methoxy-3-oxoproplyl); or a linker such as an amide bond or ether linker to provide for attachment of one or more to larger polar molecules, such as substituted or unsubstituted phenyl group, a polyoxyalkyl polyether (such as polyethylene glycol (PEG), polypropylene glycol, polyhydroxyethyl glycerol), polyethyleneimines, disaccharides, trisaccharides, polyalkylimines, small amino dextrans, a dendrimer from 0-10 generation, and the like, where Y" can further include such an attached polar molecule(s).

In some embodiments, X is a substituted alkyl group, such as a methyl group carrying polar groups or a linker to carry polar groups; $R_1$ is independently chosen from a mono-(halo) phenyl group such as 2-, 3-, or 4-chlorophenyl; a mono-(alkyl)phenyl such as a 2-, 3-, or 4-methylphenyl; a naphthalenyl group such as 1- or 2-naphthalenyl; a mono- or di(halo) naphthalenyl, such as 1-, 3-, 4-, 5-, 6-, 7-, or 8-chloronaphthalenyl, 3,4- or 5,6- or 5,7- or 5,8-dichloronaphthalenyl; a mono- or di(hydroxy)naphthalenyl, such as 1-, 3-, 4-, 5-, 6-, 7-, or 8-hydroxynaphthalenyl, 1,8-, 3,4-, dihydroxynaphthalenyl; a mono- or di or tri(alkoxy)naphthalenyl, such as 1-, 3-, 5-, 6-, 7-, or 8-methoxynaphthalenyl, 5,8-dimethoxynaphthalenyl, 1,4,8-trimethoxynaphthalenyl; a mono- or di(alkyl)naphthalenyl, such as 1-, 3-, 4-, 5-, or 6-methylnaphthalenyl, 4,5-, 4,6-dimethynaphthalenyl; a mono-(hydroxy)-mono or di(sulfo)naphthalenyl such as 4-hydroxy-2-sulfo-naphthalenyl, 8-hydroxy-3,6-disulfonaphthalenyl; mono(alkyl)-mono- or di(alkoxy)naphthalenyl, such as 1methyl-5,6-dimethoxynaphthalenyl; or a quinolinyl group such as 6-quinolynyl; $R_2$ is independently chosen from the group consisting of substituted phenyl groups such as a mono-(halo)phenyl group such as 2-, 3-, or 4-bromophenyl; a mono or di(hydroxyl)phenyl group such as 2,3,4-hydroxyphenyl and 2,4-dihydroxyphenyl; a mono- or di(halo)-mono- or di- or tri-(hydroxyl)phenyl such as 3,5-dibromo-2, 4,6-trihydroxyphenyl, 3,5-dibromo-2,4-dihydroxyphenyl, 3,5-dibromo-4-hydroxyphenyl, and 3-bromo-4-hydroxyphenyl; a mono- or di(halo)-mono- or di-(hydroxyl)-mono- or di-(alkoxy)phenyl such as 3,5-dibromo-2-hydroxy-4-methoxyphenyl; $R_3$ is independently chosen from hydrogen or an alkyl group; and Y" is independently chosen from an alky group; an alkyl group having polar substitutions, such as a sulfo group, or a carboxyl group; or a linker, such as an amide bond or an ether linker, to provide for attachment of one or more larger polar molecules, a polyoxyalkyl polyether (such as polyethylene glycol (PEG), polypropylene glycol, polyhydroxyethyl glycerol), disaccharides, polyalkylimines, and a substituted or unsubstituted phenyl group, such as a 2,4-dihydroxy-3,5-di-bromophenyl group, a 2,4-disodium-disulfophenyl group, and a 3-monosodium-monosulfophenyl group, where Y can further include such an attached polar molecule(s).

In some embodiments of the invention, the hydrazide-containing compound may comprise a formula of the following:

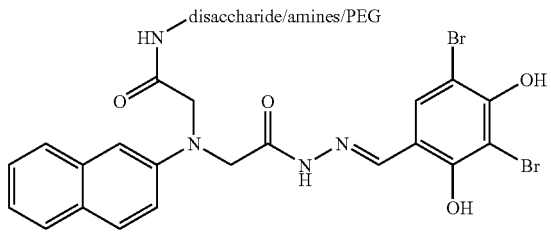

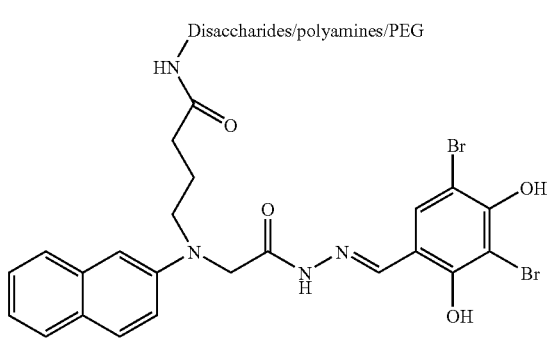

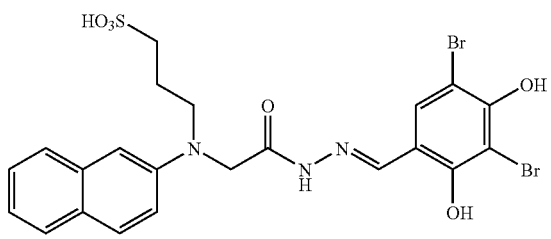

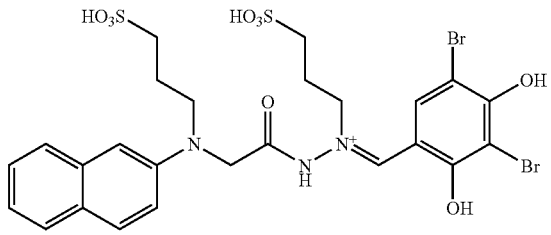

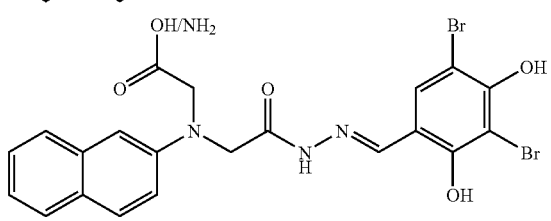

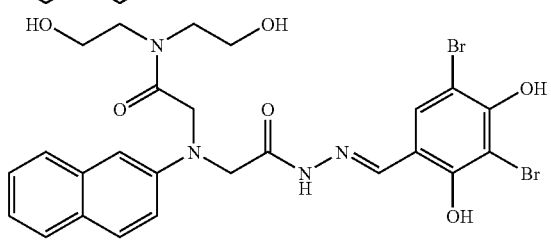

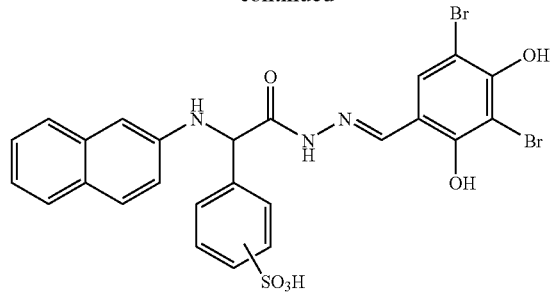
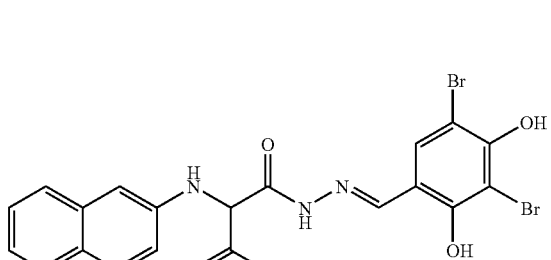
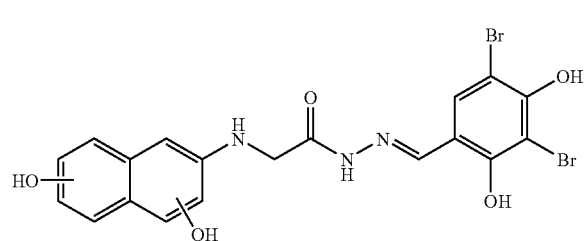
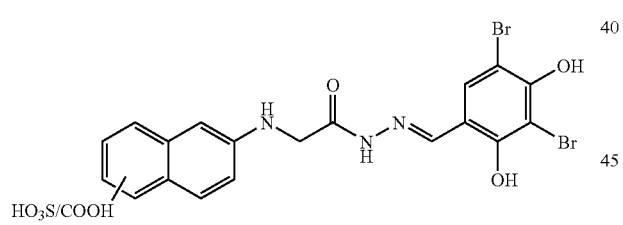
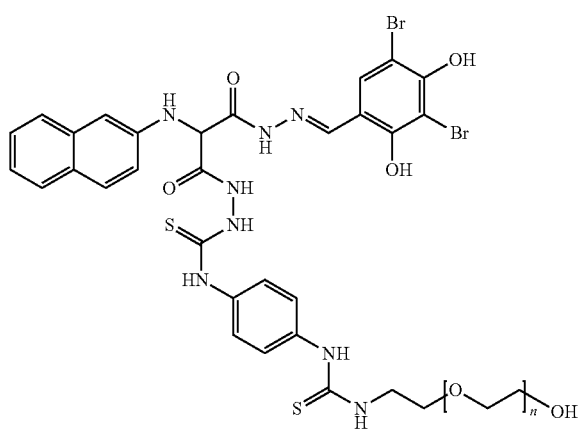
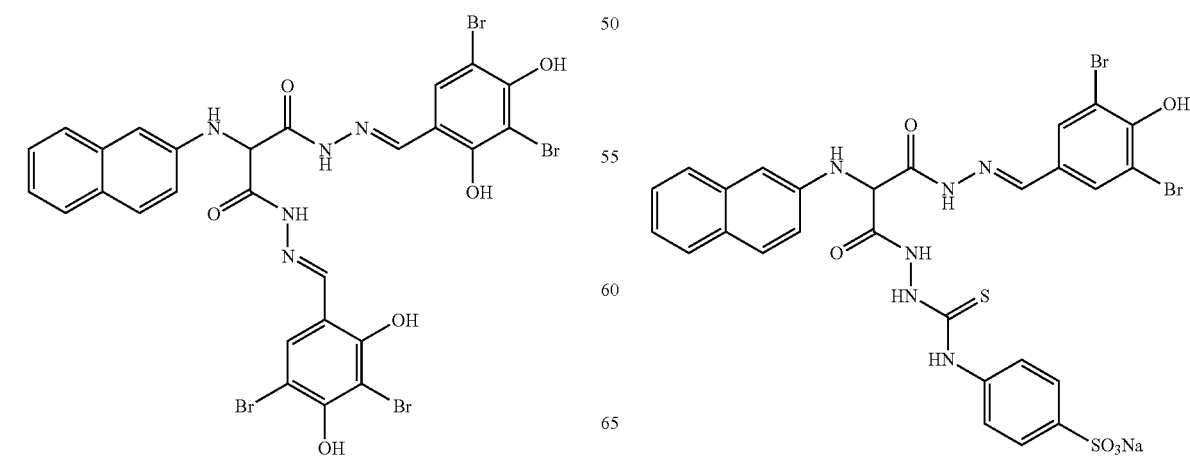

-continued

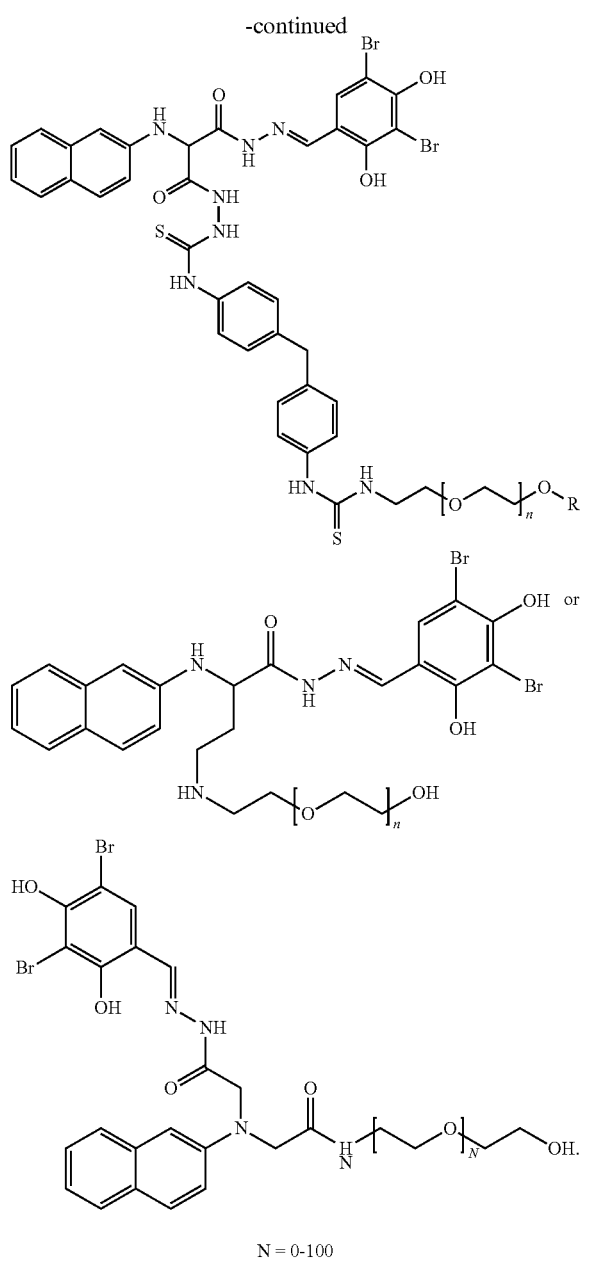

In further embodiments, the hydrazide containing compounds are dimerized by using a bifunctional linker with varied chain lengths. Such compounds are cell impermeant due to their large, bulky nature and steric hindrance. In specific embodiments, the subject compounds are generally described by Formula (Id) as follows:

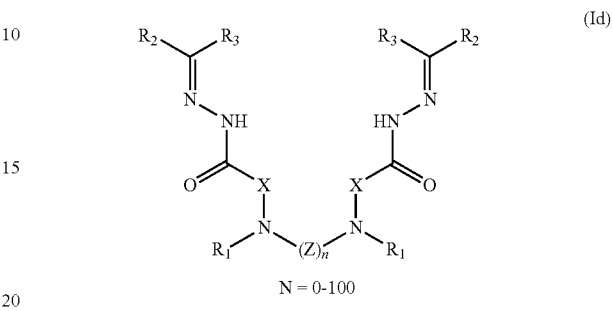

wherein Z is a monomeric or polymeric unit, such as a polyoxyalkyl polyether (such as a polyethylene glycol, polypropylene glycol, polyhydroxyethyl glycerol), a linear polyamine, or a bifunctional polysaccharide; and n is in the range of 0 to 500, 1 to 450, 2 to 400, 5 to 300, 10 to 250, 20 to 200, 30 to 150, 40 to 100, 50 to 90, and the like. In certain embodiments N has a range of 0 to 100, 1 to 95, 10 to 90, 20 to 80, 30 to 70, 40 to 60, and the like. In specific embodiments, X is independently chosen from an alkyl group, or a carbonyl group; Y is independently chosen from an alky group; an alkyl group having polar substitutions, such as a sulfo group, or a carboxyl group; or a linker, such as an amide bond or an ether linker, to provide for attachment of one or more larger polar molecules, a polyoxyalkyl polyether (such as polyethylene glycol (PEG), polypropylene glycol, polyhydroxyethyl glycerol), disaccharides, polyalkylimines, and the like, where Y can further include such an attached polar molecule(s); $R_1$, is independently chosen from a substituted phenyl group, a quinolinyl group, an anthracenyl group, and a naphthalenyl group; $R_2$ is a substituted phenyl group; and $R_3$ is independently chosen from hydrogen and an alkyl group; or a pharmaceutically acceptable derivative thereof, as an individual stereoisomer or a mixture thereof.

In some embodiments of the invention, the hydrazide-containing compound may comprise a formula of the following:

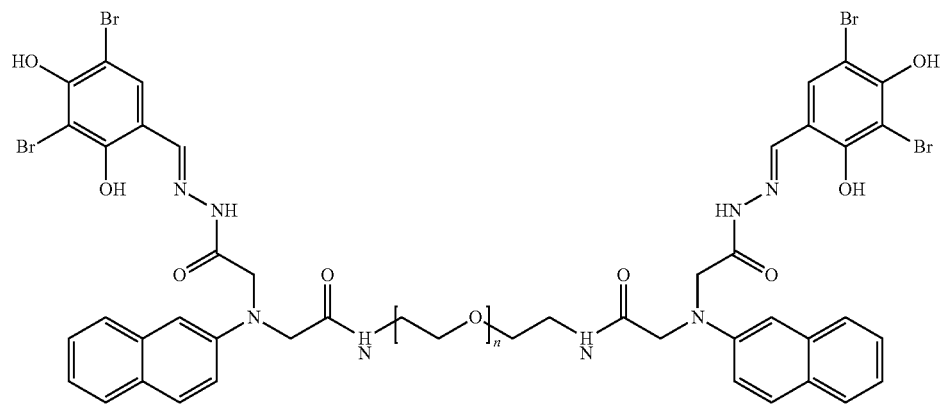

Pharmaceutical Preparations

Also provided by the invention are pharmaceutical preparations of the subject hydrazide-containing compounds described above. The subject compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols. Preferably, the formulations are free of detectable DMSO (dimethyl sulfoxide), or are formulated with a penetration enhancer other than DMSO. The formulations may be designed for administration to subjects or patients in need thereof via a number of different routes, which may be parenteral or enteral. Exemplary routes of administration include oral, buccal, rectal, parenteral, intraperitoneal, intradermal, transdermal, intracheal, etc., administration.

In pharmaceutical dosage forms, the subject compounds of the invention may be administered in the form of their pharmaceutically acceptable derivative, such as a salt, or they may also be used alone or in appropriate association, as well as in combination, with other pharmaceutically active compounds. The following methods and excipients are merely exemplary and are in no way limiting.

In one embodiment of particular interest, the compounds of the invention are administered to the gastrointestinal tract of the subject, so as to provide for decreased fluid secretion. Suitable formulations for this embodiment of the invention include any formulation that provides for delivery of the compound to the gastrointestinal surface, particularly an intestinal tract surface.

For oral formulations, the subject compounds can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. Of particular interest is formulation of the subject hydrazide-containing compounds with a buffering agent, to provide for protection of the compound from low pH of the gastric environment. It may also be preferable to provide an enteric coating. In one embodiment, the compounds are formulated for oral delivery with a flavoring agent, e.g., in a liquid, solid or semi-solid formulation.

Oral formulations can be provided as gelatin capsules, which may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase patient acceptance.

Other suitable oral formulations include those that provide for sustained release, which may be controlled release, of the compound. Such formulations include hydrogels, microparticles, and other dosage forms and formulations known in the art.

Water, a suitable oil, saline, aqueous dextrose, and related sugar solutions and glycols such as propylene glycol or polyethylene glycols, may be used as carriers for parenteral solutions. Such solutions can also contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Where desired, solubilizers for use can include vitamin E TPGS (d-α-tocopheryl polyethylene glycol 1000 succinate), cyclodextrins, and the like.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The compounds of the invention can be utilized in aerosol formulation to be administered via inhalation. The compounds of the present invention can be formulated into pressurized acceptable propellants such as dichlorodifluoromethane, propane, nitrogen and the like.

In one embodiment, topical administration (e.g., by transdermal administration) is of interest. Topical formulations can be in the form of a transdermal patch, ointment, paste, lotion, cream, gel, and the like. Topical formulations may include one or more of a penetrating agent, thickener, diluent, emulsifier, dispersing aid, or binder. Where the compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin.

Compounds that have been used to enhance skin permeability include: the sulfoxides dimethylsulfoxide (DMSO) and decylmethylsulfoxide ($C_{10}$ MSO); ethers such as diethylene glycol monoethyl ether, dekaoxyethylene-oleylether, and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan-2-one; alcohols such as ethanol, propanol, octanol, benzyl alcohol, and the like; petrolatums, such as petroleum jelly (petrolatum), mineral oil (liquid petrolatum), and the like; fatty acids such as $C_8$-$C_{22}$ and other fatty acids (e.g., isostearic acid, octanoic acid, oleic acid, lauric acid, valeric acid); $C_8$-$C_{22}$ fatty alcohols (e.g., oleyl alcohol, lauryl alcohol); lower alkyl esters of $C_8$-$C_{22}$ fatty acids and other fatty acids (e.g., ethyl oleate, isopropyl myristate, butyl stearate, methyl laurate, isopropyl myristate, isopropyl palmitate, methylpropionate, ethyl oleate); monoglycerides of $C_8$-$C_{22}$ fatty acids (e.g., glyceryl monolaurate); tetrahydrofurfuryl alcohol polyethylene glycol ether; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; di-lower alkyl esters of $C_6$-$C_8$ diacids (e.g., diisopropyl adipate); ethyl acetate; acetoacetic ester; polyols and esters thereof such as propylene glycol, ethylene glycol, glycerol, butanediol, polyethylene glycol, and polyethylene glycol monolaurate; amides and other nitrogenous compounds such as urea, dimethylacetamide (DMA), dimethylformamide (DMF), 2-pyrrolidone, N-alkylpyrrolidone, e.g., 1-methyl-2-pyrrolidone; ethanol amine, diethanol amine and triethanolamine; terpenes; alkanones, and organic acids, particularly salicylic acid and salicylates, citric acid and succinic acid. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J Pharm. Pharmacol.* 2002; 54(4):499-508; Karande et al., *Pharm. Res.* 2002; 19(5):655-60; Vaddi et al., *J. Pharm. Sci.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., Urology 2001; 57(2):301-5; Kiijavainen et al., *Eur. J. Pharm. Sci.* 2000; 10(2):97-102; and Tenjarla et al., *Int. J. Pharm.* 1999; 192(2):147-58.

Where the compound is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. In one embodiment, the compound is formulated with a penetration enhancer other than DMSO.

In one embodiment, the compound is provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, and can be a polymeric or hydrogel matrix.

Depending on the subject and condition being treated and on the administration route, the subject compounds may be administered in dosages of, for example, 0.1 g to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

For use in the subject methods, the subject compounds may be formulated with other pharmaceutically active agents, including other CFTR-inhibiting agents or agents that block intestinal chloride channels.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Conditions Amenable to Treatment Using the CFTR Inhibitors of the Invention

The CFTR inhibitors disclosed herein are useful in the treatment of a CFTR-mediated condition, i.e., any condition, disorder or disease, or symptom of such condition, disorder, or disease, that results from activity of CFTR, e.g., activity of CFTR in ion transport. Such conditions, disorders, diseases, or symptoms thereof are amenable to treatment by inhibition of CFTR activity, e.g., inhibition of CFTR ion transport.

In one embodiment, the CFTR inhibitors of the invention are used in the treatment of conditions associated with aberrantly increased intestinal secretion, particularly acute aberrantly increased intestinal secretion. CFTR activity has been implicated in intestinal secretion in response to various agonists, including cholera toxin (see, e.g., Snyder et al. 1982 *Bull. World Health Organ.* 60:605-613; Chao et al. 1994 *EMBO J.* 13:1065-1072; Kimberg et al. 1971 *J. Clin. Invest.* 50:1218-1230). Thus CFTR inhibitors of the invention can be administered in an amount effective to inhibit CFTR ion transport and thus decrease intestinal fluid secretion. In such embodiments, CFTR inhibitors according to the invention are generally administered by administration to a mucosal surface of the gastrointestinal tract (e.g., by an enteral route, e.g., oral, intraintestinal, rectal, and the like) or to a mucosal surface of the oral or nasal cavities, or (e.g., intranasal, buccal, sublingual, and the like). In certain embodiments administration of a CFTR inhibitor of the invention that is relatively membrane impermeant (e.g., having decreased membrane permeance characteristics (e.g., due to modification by PEGylation and the like as described above)) is of particular interest.

Thus, CFTR inhibitors can be used in the treatment of intestinal inflammatory disorders and diarrhea, particularly secretory diarrhea. Secretory diarrhea is the biggest cause of infant death in developing countries, with about 5 million deaths annually (Gabriel et al., 1994 *Science* 266: 107-109). Several studies, including those using CF mice, indicate that CFTR is the final common pathway for intestinal chloride ion (and thus fluid) secretion in response to various agonists (Snyder et al., 1982, *Bull. World Health Organ.* 60: 605-613; Chao et al., 1994 *EMBO. J.* 13: 1065-1072; and Kimberg et al., 1971, *J. Clin. Invest.* 50: 1218-1230).

Diarrhea amenable to treatment using the CFTR inhibitors of the invention can result from exposure to a variety of pathogens or agents including, without limitation, cholera toxin (*Vibrio cholera*), *E. coli* (particularly enterotoxigenic (ETEC)), *Shigella, Salmonella, Campylobacter, Clostridium difficile*, parasites (e.g., *Giardia, Entamoeba histolytica, Cryptosporidiosis, Cyclospora*), diarrheal viruses (e.g., rotavirus), food poisoning, or toxin exposure that results in increased intestinal secretion mediated by CFTR.

Other diarrheas include diarrhea associated with AIDS (e.g., AIDS-related diarrhea), diarrheas caused by anti-AIDS medications such as protease inhibitors, and inflammatory gastrointestinal disorders, such as ulcerative colitis, inflammatory bowel disease (IBD), Crohn's disease, and the like. It has been reported that intestinal inflammation modulates the expression of three major mediators of intestinal salt transport and may contribute to diarrhea in ulcerative colitis both by increasing transepithelial Cl⁻ secretion and by inhibiting the epithelial NaCl absorption (see, e.g., Lohi et al., 2002, *Am. J. Physiol. Gastrointest. Liver Physiol.* 283(3):G567-75).

CFTR inhibitors of the invention can also be used in treatment of conditions such as polycystic kidney disease, and find further use as male infertility drugs, by inhibition of CFTR activity in the testis.

CFTR inhibitors of the invention can be further screened in larger animal models (e.g., the rabbit model described in Spira et al., 1981, *Infect. Immun.* 32:739-747). In addition, analysis of stool output using live *Vibrio cholerae* can also be examined to further characterize the CFTR inhibitors of the invention.

Non-Human Animal Models and Human Tissue Models of CFTR-Deficiencies

The CFTR inhibitors of the invention can also be used to generate non-human animal models of disease, where the disease is associated with decreased CFTR function (e.g., decreased ion transport). There is increasing evidence that defective fluid and macromolecular secretion by airway submucosal glands leads to impaired mucociliary and bacterial clearance in CFTR-deficient subjects, particularly in those affected with cystic fibrosis (CF); however, functional studies in human airway glands have been restricted to severely diseased airways obtained at the time of lung transplantation (Jayaraman et al. 2001 *Proc. Natl. Acad. Sci. USA* 98:8119-8123). Acute CFTR inhibition permits determination of the role of CFTR in water, salt and macromolecule secretion by submucosal glands. High-affinity CFTR inhibitors permit the pharmacological creation of non-human animal models that mimic CFTR-deficiency in humans, e.g., mimics the human CF phenotype. In particular, large animal models of CFTR deficiency (e.g., CF) find particular use in elucidating the pathophysiology of initiation and progression of airway disease in CF, and in evaluating the efficacy of CF therapies, e.g., screening candidate agents for treatment of CFTR-deficiencies or symptoms thereof.

Inhibition of CFTR ion transport can be manifested in airway and pancreatic disorders, as well as infertility in males. For example, inhibition of CFTR channels in the lungs and airways influences airway surface fluids leading to accumulation of mucus, which in turn plugs airways and collects heavily on the lung walls, providing a prime environment for infection to occur, which in turn can lead to chronic lung disease. This same phenomenon occurs in the pancreas, where the accumulated mucus disrupts the exocrine function of the pancreas and prevents essential food-processing enzymes from reaching the intestines.

Such non-human animal models can be generated by administration of an amount of a CFTR inhibitor effective to decrease CFTR activity in ion transport. Of particular interest is the use of the CFTR inhibitors of the invention to induce the cystic fibrosis (CF) phenotype in a non-human animal. Administration of an amount of a CFTR inhibitor effective to inhibit CFTR in, for example, lung effectively mimics the CFTR defect found in CF. Routes of delivery for CFTR inhibitor are discussed in detail above. Depending on the non-human animal used, the subject compounds may be administered in dosages of, for example, 50 to 500 µg/kg body weight one to three times a day by an intraperitoneal, subcutaneous, or other route to generate the non-human animal models. Oral dosages may be up to about ten times the intraperitoneal or subcutaneous dose.

Non-human animal models of CFTR-associated disease can be used as models of any appropriate condition associated with decreased CFTR activity. Such conditions include those that are associated with CFTR mutations, which mutations result in abnormalities in epithelial ion and water transport. These abnormalities can in turn be associated with derangements in airway mucociliary clearance, as well as in other mucosal epithelia and ductal epithelia. Conditions that can be pharmacologically modeled by inducing a CFTR-deficient phenotype in a non-human animal include, without limitation, cystic fibrosis (including atypical CF), idiopathic chronic pancreatitis, vas deferens defects, mild pulmonary disease, asthma, and the like. For a review of disorders associated with impaired CFTR function, see, e.g., Noone et al. *Respir Res* 2 328-332 (2001). CFTR inhibitor-generated non-human animal models can also serve as models of microbial infection (e.g., bacterial, viral, or fungal infection, particularly respiratory infections) in a CFTR-deficient subject. In one embodiment of particular interest, the CFTR inhibitors of the invention are used to pharmacologically induce the cystic fibrosis (CF) phenotype.

Animals suitable for use in the production of the animal models of the invention include any animal, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest.

The CFTR inhibitors can also be contacted with isolated human tissue to create ex vivo models of disease. Such tissue is contacted with an amount of a CFTR inhibitor effective to decrease CFTR activity in the tissue, which may be for as little as 15 minutes, or as much as two hours or more. Human tissues of interest include, without limitation, lung (including trachea and airways), liver, pancreas, testis, and the like. Physiological, biochemical, genomic or other studies can be carried out on the inhibitor-treated tissue to identify novel therapeutic target molecules that are important in the pathophysiology of a disease. For example, isolated tissue from humans without CF can be exposed to inhibitor sufficient to induce the CF phenotype and such studies can be carried out to identify novel therapeutic target molecules that are important in the pathophysiology of CF.

Synthesis of the Compounds of the Invention

Compounds of the invention may be prepared according to methods known to one skilled in the art, or by methods similar to the method described below.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Theodora W. Greene, Peter G. M. Wuts, *Protective Groups in Organic Synthesis* (1999), 3rd Ed., Wiley-Interscience. The protecting group may also be a polymer resin such as a Wang resin or a 2-chlorotrityl chloride resin.

It will also be appreciated by those skilled in the art, although such protected derivatives of compounds of formula (I), as described above (e.g., in the Overview and in Hydrazide-Containing Compounds and Derivatives), may not possess pharmacological activity as such, they may be administered to a mammal and thereafter metabolized in the body to form compounds of the invention which are pharmacologically active. Such derivatives may therefore be described as "prodrugs". All prodrugs of compounds of formula (I) are included within the scope of the invention.

The following Reaction Schemes illustrate methods to make compounds of the invention. It is understood that one of ordinary skill in the art would be able to make the compounds of the invention by similar methods or by methods known to one skilled in the art. In general, starting components may be obtained from sources such as Aldrich, or synthesized according to sources known to those of ordinary skill in the art (see, e.g., Smith and March, *March's Advanced Organic Chemistry: Reactions, Mechanisms, and Structure,* 5th edition (Wiley Interscience, New York)). Moreover, the various substituted groups (e.g., $R_1$, $R_2$, $R_3$, and X, etc.) of the compounds of the invention may be attached to the starting components, intermediate components, and/or final products according to methods known to those of ordinary skill in the art.

The following Reaction Scheme 1 is directed to the preparation of compounds of formula (I), which are compounds of the invention as described above (e.g., in the Overview and in Hydrazide-Containing Compounds and Derivatives), where $R_1$, $R_2$, and $R_3$ are as described above (e.g., in the Overview and in Hydrazide-Containing Compounds and Derivatives).

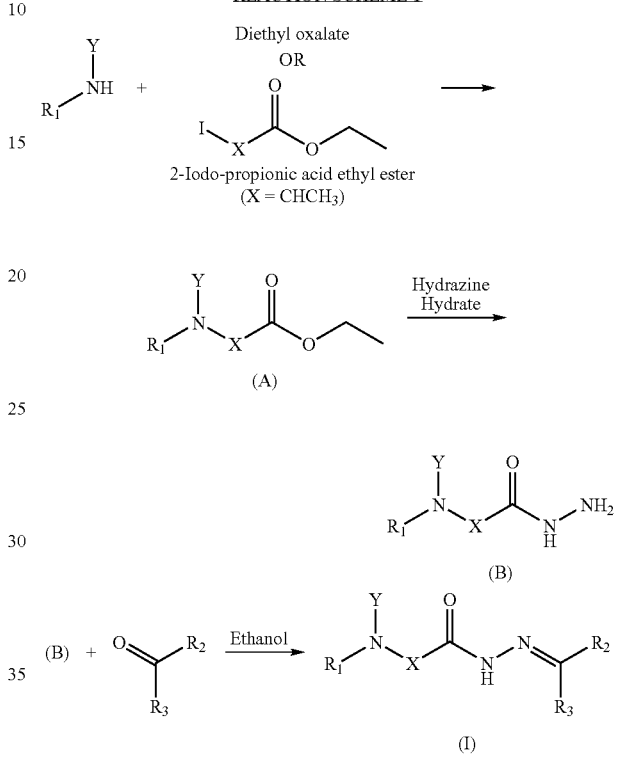

In general, compounds of Formula (I) are prepared by first combining an $R_1$-group containing a terminal amine containing a Y group with diethyl oxalate or an X containing compound such as X-substituted ethyl iodoacetate, where X is as described above, each at 10 mmol. The resulting reaction mixture is then stirred overnight at elevated temperature. Upon cooling, the solid material is filtered and recrystallized from hexane to yield compound of formula (A). A solution of the compound of formula (A) in ethanol is then refluxed with 12 mmol hydrazine hydrate for a period of time of about 10 hours. The solvent and excess reagent are then distilled under vacuum. The product is then recrystallized from ethanol to yield the compound of formula (B). The compound of formula (B) is then combined with a $R_2$, $R_3$-group containing carbonyl group (e.g., a ketone or an aldehyde) in ethanol and then refluxed for a period of time of about 3 hours to yield the desired product of Formula (I).

Alternatively, compounds of Formula (I), where and X is an alkyl group containing $X_1$, wherein $X_1$ is an alkyl group such as a substituted or unsubstituted, saturated linear or branched hydrocarbon group or chain (compounds of Formula Ia) can be prepared according to the following Reaction Scheme 2 wherein $R_1$, $R_2$, and $R_3$ are as described above (e.g., in the Overview and in Hydrazide-Containing Compounds and Derivatives).

REACTION SCHEME 2

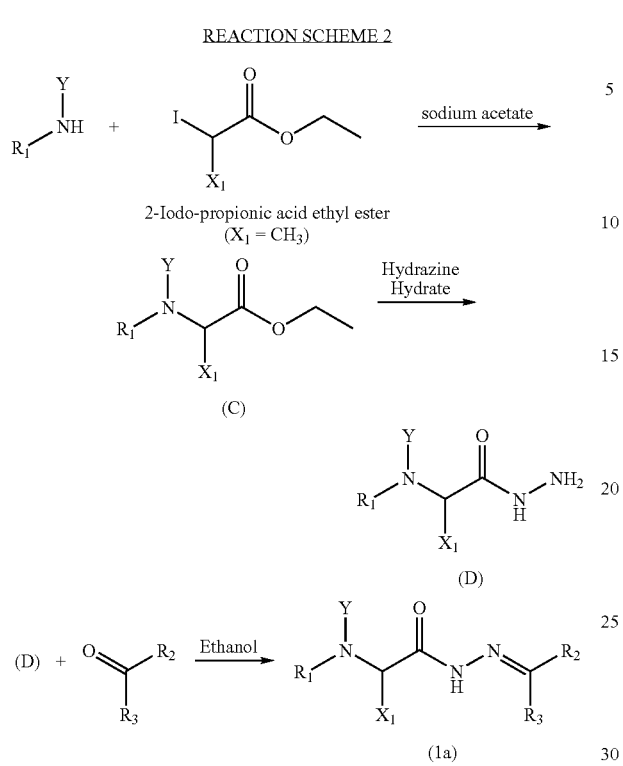

In general, compounds of Formula (Ia) are prepared by first combining an $R_1$-group containing a terminal amine containing an Y group with ethyl iodoacetate containing an $X_1$ group, where $X_1$ is as described above, each at 10 mmol with 20 mmol sodium acetate. The resulting reaction mixture is then stirred at elevated temperature for a period of time of about 3 hours. Upon cooling, the solid material is filtered and recrystallized from hexane to yield compound of formula (C). A solution of the compound of formula (C) in ethanol is then refluxed with 12 mmol hydrazine hydrate for a period of time of about 10 hours. The solvent and excess reagent are then distilled under vacuum. The product is then recrystallized from ethanol to yield the compound of formula (D). The compound of formula (D) is then combined with a $R_2$, $R_3$-group containing carbonyl group (e.g., a ketone or an aldehyde) in ethanol and then refluxed for a period of time of about 3 hours to yield the desired product of Formula (Ia).

The following Reaction Scheme 3 is directed to the preparation of compounds of Formula (Ib) wherein X is $CH_2$, which are compounds of the invention as described above (e.g., in the Overview and in Hydrazide-Containing Compounds and Derivatives), where $R_1$, $R_2$, and $R_3$ are as described above (e.g., in the Overview and in Hydrazide-Containing Compounds and Derivatives).

REACTION SCHEME 3

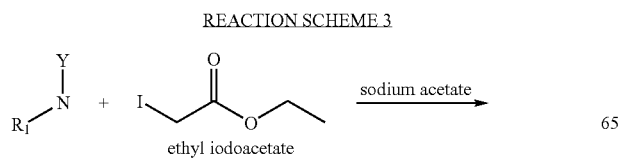

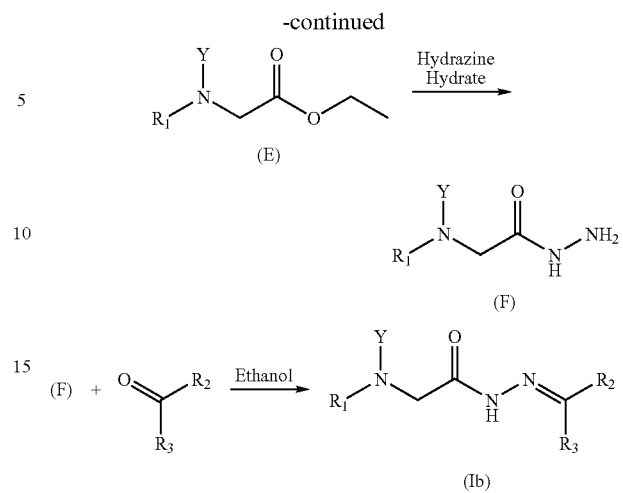

In general, compounds of Formula (Ib) are prepared by first combining an $R_1$-group containing a terminal amine with ethyl iodoacetate each at 10 mmol with 20 mmol sodium acetate. The resulting reaction mixture is then stirred at an elevated temperature for a period of time of about 3 hours. Upon cooling, the solid material is filtered and recrystallized from hexane to yield compound of formula (E). A solution of the compound of formula (E) in ethanol is then refluxed overnight with 12 mmol hydrazine hydrate for a period of time of about 10 hours. The solvent and excess reagent are then distilled under vacuum. The product is then recrystallized from alcohol to yield the compound of formula (F). The compound of formula (F) is then combined with a $R_2$, $R_3$-group containing carbonyl group (e.g., a ketone or an aldehyde) in ethanol and then refluxed for a period of time of about 3 hours to yield the desired product of Formula (Ib).

Alternatively, compounds of Formula (I), where X is a carbonyl group (compounds of Formula Ic) can be prepared according to the following Reaction Scheme 4 wherein $R_1$, $R_2$, and $R_3$ are as described above in the Overview.

REACTION SCHEME 4

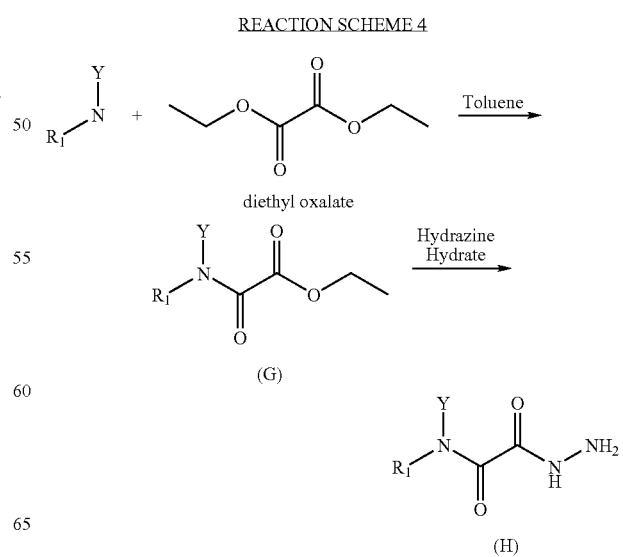

-continued

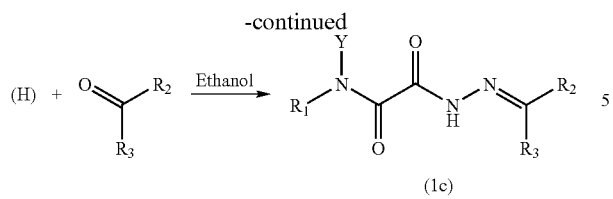

(Ic)

In general, compounds of Formula (Ic) are prepared by first combining an R$_1$-group containing a terminal amine containing a Y group with diethyl oxalate each at 10 mmol in toluene. The resulting reaction mixture is then stirred at an elevated temperature for a period of time of about 3 hours. Upon cooling, the solid material is filtered and recrystallized from hexane to yield compound of formula (G). A solution of the compound of formula (G) in ethanol is then refluxed with 12 mmol hydrazine hydrate for a period of time of about 10 hours. The solvent and excess reagent are then distilled under vacuum. The product is then recrystallized from ethanol to yield the compound of formula (H). The compound of formula (H) is then combined with a R$_2$, R$_3$-group containing a carbonyl group in ethanol and then refluxed for a period of time of about 3 hours to yield the desired product of Formula (Ic).

Alternatively, compounds of Formula (I), where X is an alkyl group containing Y" (compounds of Formula Ie) can be prepared according to the following Reaction Schemes 5-8 wherein R$_1$, R$_2$, and R$_3$ are as described above (e.g., in the Overview and in Hydrazide-Containing Compounds and Derivatives), and wherein Y" is independently chosen from an substituted or unsubstituted alkyl group, such as a substituted or unsubstituted, saturated linear or branched hydrocarbon group or chain (e.g., C$_1$ to C$_8$) including, e.g., methyl, ethyl, isopropyl, tert-butyl, heptyl, n-octyl, dodecyl, octadecyl, amyl, 2-ethylhexyl; an alkyl group carrying polar groups such as hydroxy, sulfo, carboxylate, and a substituted or unsubstituted carboxamide groups (where exemplary groups include, such as 3-sulfopropyl, 4-sulfobutyl, carboxymethyl, 2-carboxypropyl, 2-methoxy-2-oxoethyl, 3-methoxy-3-oxoproplyl); or a linker such as an amide bond or ether linker to provide for attachment of one or more to larger polar molecules, such as substituted or unsubstituted phenyl group, a polyoxyalkyl polyether (such as polyethylene glycol (PEG), polypropylene glycol, polyhydroxyethyl glycerol), polyethyleneimines, disaccharides, trisaccharides, polyalkylimines, small amino dextrans and the like, where Y" can further include such an attached polar molecule(s).

REACTION SCHEME 5

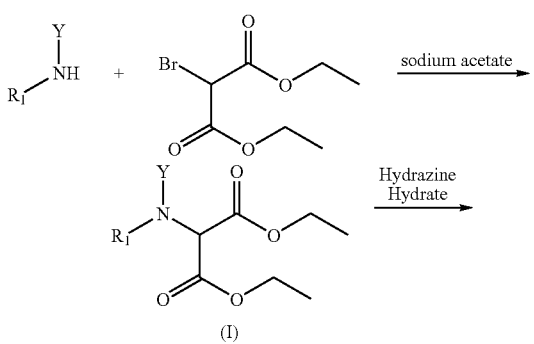

(I)

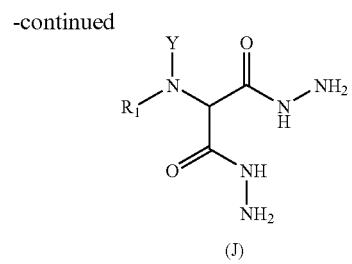

(J)

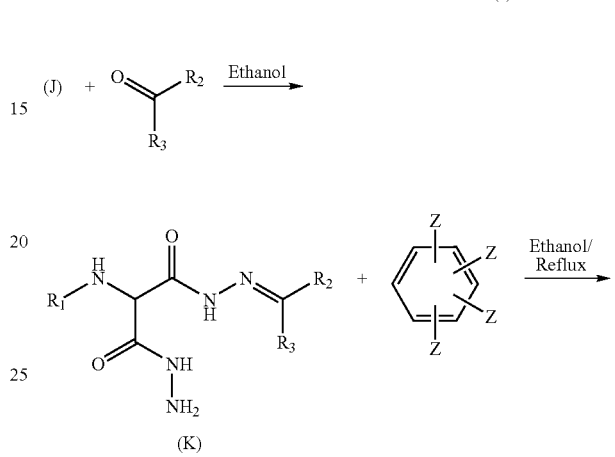

(K)

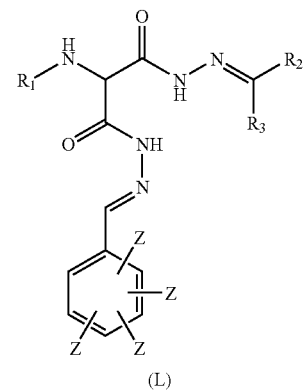

(L)

In general, in some embodiments, compounds of Formula (Ie) are prepared by first combining an R$_1$-group containing a terminal amine containing a Y group with diethyl bromomalonate each at 10 mmol. The resulting reaction mixture is then stirred at an elevated temperature for a period of time of about 8 hours. Upon cooling, the solid material is filtered and recrystallized from hexane to yield compound of formula (I). A solution of the compound of formula (I) in ethanol is then refluxed with 12 mmol hydrazine hydrate for a period of time of about 10 hours. The solvent and excess reagent are then distilled under vacuum. The product is then recrystallized from ethanol to yield the compound of formula (J). The compound of formula (J) is then combined with a R$_2$, R$_3$-group containing a carbonyl group in ethanol and then refluxed for a period of time of about 3 hours to yield the desired product of Formula (K). The compound of formula (K) is then combined with a substituted or unsubstituted phenyl group as described in greater detail above (e.g., in the Overview and in Hydrazide-Containing Compounds and Derivatives) and refluxed for a period of time. The product is then recrystallized from ethanol to yield the compound of formula (L).

REACTION SCHEME 6

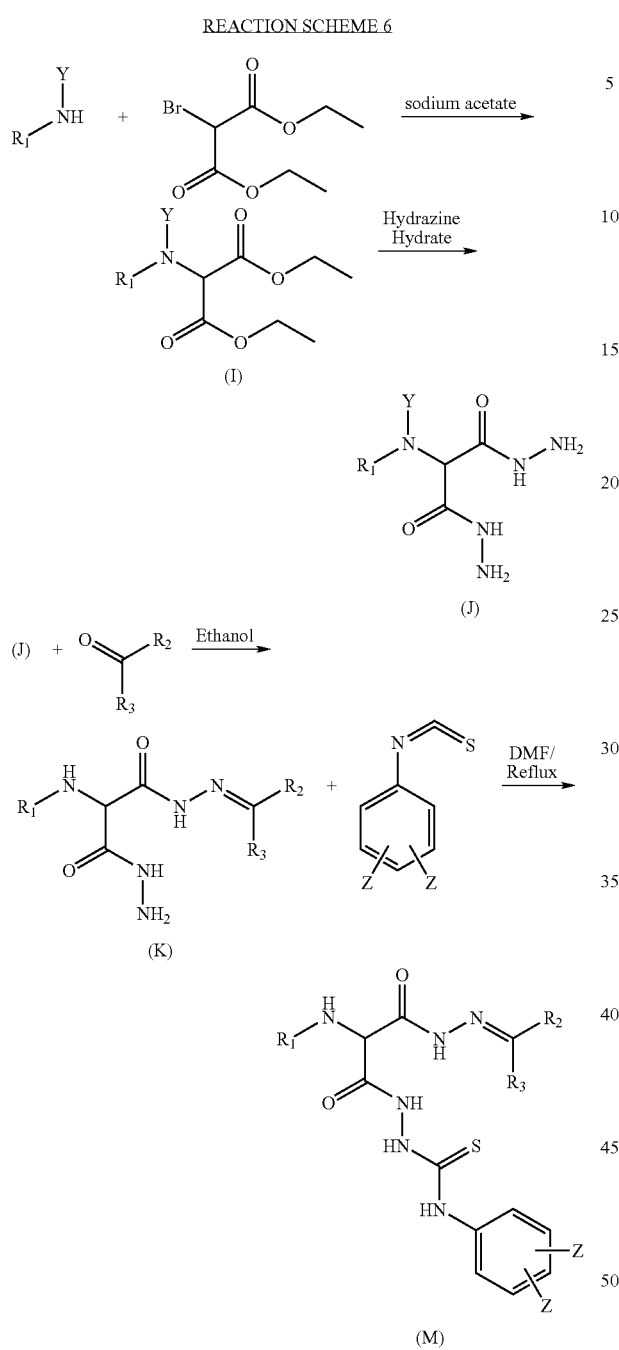

containing a carbonyl group in ethanol and then refluxed for a period of time of about 3 hours to yield the desired product of Formula (K). The compound of formula (K) is then combined with a thiocyanate substituted phenyl group as described in greater detail above (e.g., in the Overview and in Hydrazide-Containing Compounds and Derivatives) and refluxed for a period of time. The product is then recrystallized from ethanol to yield the compound of formula (M).

REACTION SCHEME 7

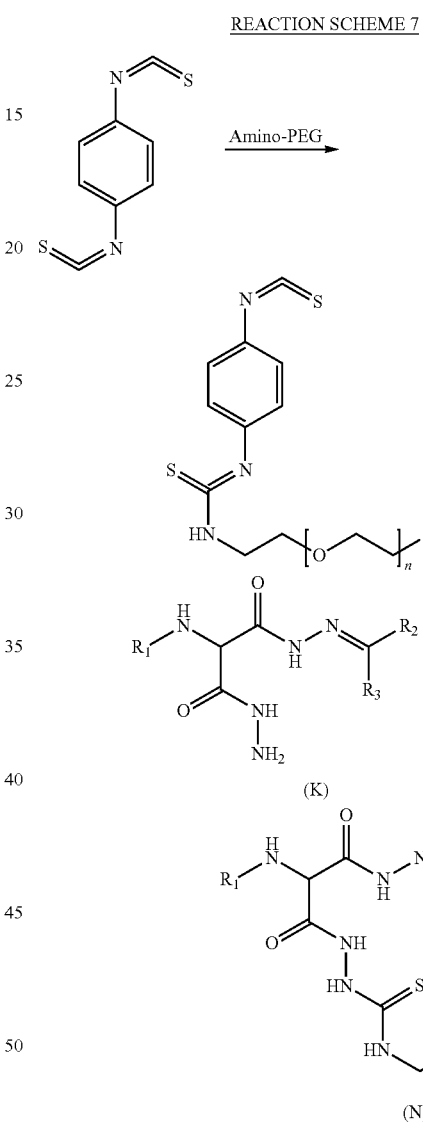

In general, in some embodiments, compounds of Formula (Ie) are prepared by first combining an $R_1$-group containing a terminal amine containing a Y group with diethyl bromomalonate each at 10 mmol. The resulting reaction mixture is then stirred at an elevated temperature for a period of time of about 8 hours. Upon cooling, the solid material is filtered and recrystallized from hexane to yield compound of formula (I). A solution of the compound of formula (I) in ethanol is then refluxed with 12 mmol hydrazine hydrate for a period of time of about 10 hours. The solvent and excess reagent are then distilled under vacuum. The product is then recrystallized from ethanol to yield the compound of formula (J). The compound of formula (J) is then combined with a $R_2$, $R_3$-group In general, in some embodiments, compounds of Formula (Ie) are prepared by first combining a thiocyanate containing a phenyl group with Amino-PEG in DMF and stirred at an elevated temperature for a period of time of about 24 hours. The DMF is then evaporated in vacuo, and the residue is dissolved in minimal quantity EtOAc and added to a stirred solution of $Et_2O$. The resulting precipitate is then filtered and washed in $Et_2O$ to give the PEG-containing compound. The PEG-containing compound is then combined with the compound of formula (K) and refluxed for a period of time. The product is then recrystallized from ethanol to yield the compound of formula (N).

REACTION SCHEME 8

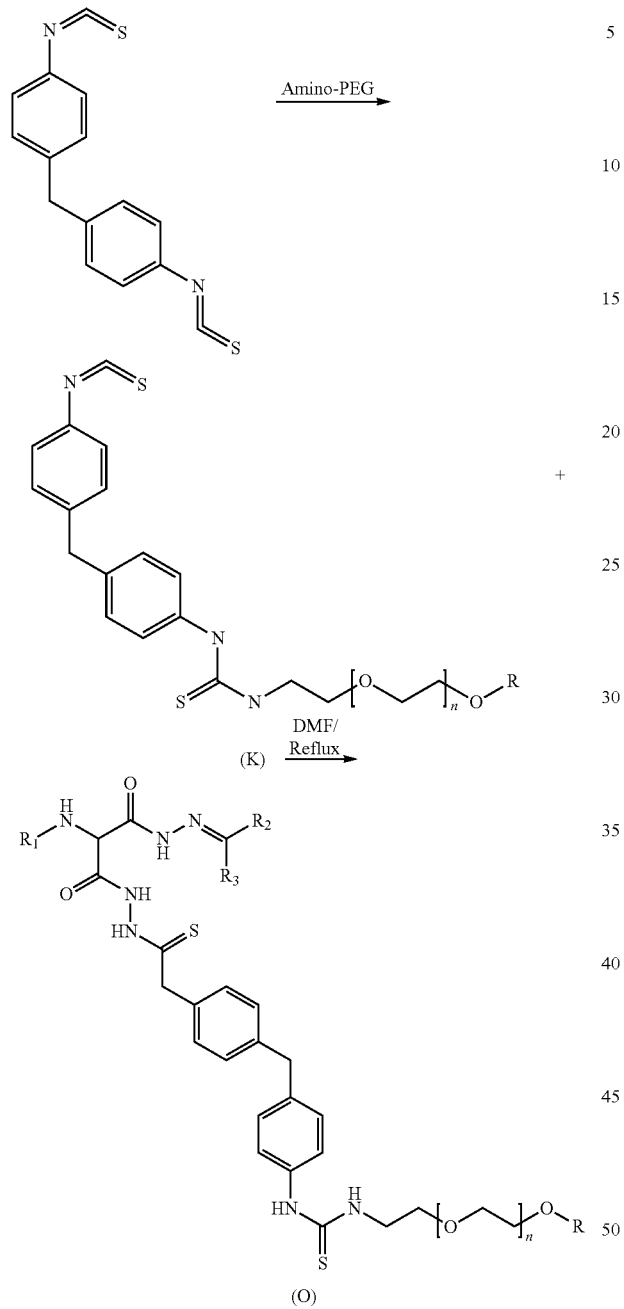

REACTION SCHEME 9

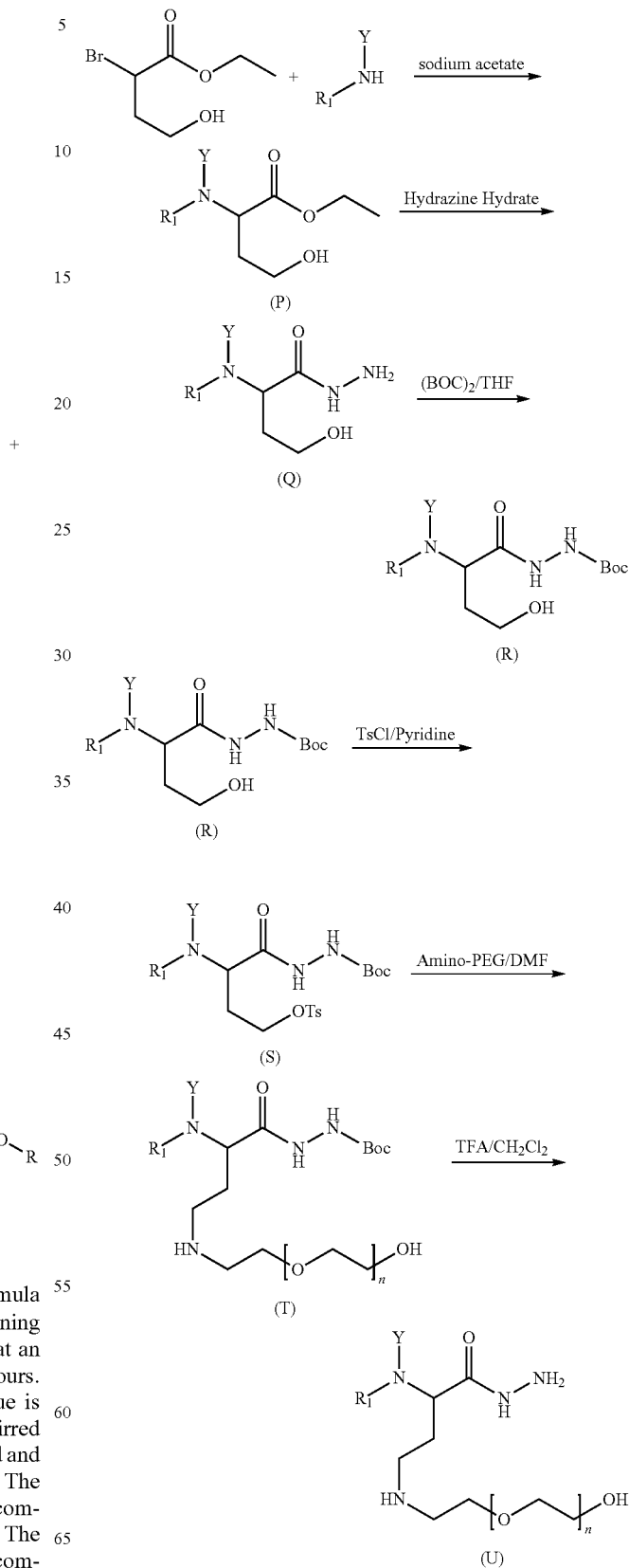

In general, in some embodiments, compounds of Formula (Ie) are prepared by first combining a thiocyanate containing a phenyl group with Amino-PEG in DMF and stirred at an elevated temperature for a period of time of about 24 hours. The DMF is then evaporated in vacuo, and the residue is dissolved in minimal quantity EtOAc and added to a stirred solution of $Et_2O$. The resulting precipitate is then filtered and washed in $Et_2O$ to give the PEG-containing compound. The PEG-containing compound is then combined with the compound of formula (K) and refluxed for a period of time. The product is then recrystallized from ethanol to yield the compound of formula (O).

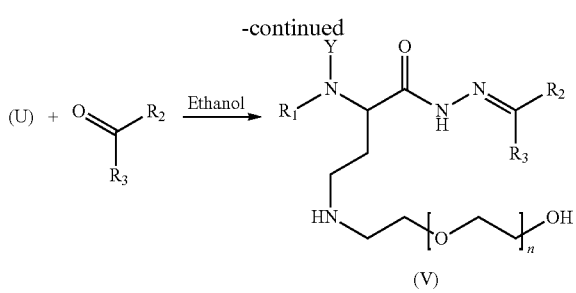

In general, in some embodiments, compounds of Formula (Ie) are prepared by first combining an $R_1$-group containing a terminal amine containing a Y group with diethyl bromobuterolacetone or bromobuterolactone each at 10 mmol. The resulting reaction mixture is then stirred at an elevated temperature for a period of time of about 8 hours. Upon cooling, the solid material is filtered and recrystallized from hexane to yield compound of formula (P). A solution of the compound of formula (P) in ethanol is then refluxed with 12 mmol hydrazine hydrate for a period of time of about 10 hours. The solvent and excess reagent are then distilled under vacuum. The product is then recrystallized from ethanol to yield the compound of formula (Q). The compound of formula (Q) (10 mM) is then combined with 20 mM (BOC)$_2$O in 10 mL of THF and heated under reflux conditions for a period of time of about 5 hours. The solvent is then removed, and the residue is purified by column chromatography on silica gel and eluted with dichloromethane to give the compound of formula (R). The compound of formula (R) (1 mmol) is then combined with TsCl (1 mmol) in pyridine (5 ml) in three portion a period of time of about 30 min apart form one another. The reaction mixture is then stirred at a low temperature of about −15° C. for a period of time of about 8 hours. The reaction mixture is then allowed to warm to room temperature, diluted with 1N HCl, and then extracted three times with EtOAc. The combined organic extract is then washed with brine, dried with NaSO4 and evaporated to dryness to give the compound of formula (S). The compound of formula (S) is then combined with amino-PEG, such as 2-aminoethoxyethanol, in DMF and stirred at an elevated temperature for a period of time of about 24 hours. The DMF is then evaporated in vacuo, and the residue is dissolved in minimal quantity EtOAc and added to a stirred solution of Et$_2$O. The resulting precipitate is then filtered and washed in Et$_2$O to give the compound of formula (T). The compound of formula (T) is then dissolved in minimal amount of trifluoroacetic acid:Ch$_2$Cl$_2$ (1:1) and stirred at room temperature for a period of time of about 30 minutes. The reaction mixture is the diluted with saturated aqueous NaHCO$_3$ and extracted with CH$_2$Cl$_2$. The combined organic layer is then washed successively with water and brine, dried and concentrated in vacuo to yield the compound of formula (U). The compound of formula (U) is then combined with a $R_2$, $R_3$-group containing a carbonyl group in ethanol and then refluxed for a period of time of about 3 hours to yield the desired product of Formula (V).

Structures were confirmed by $^1$H-NMR and Mass spectrometry. Purity was >98% as judged by thin layer chromatography and HPLC.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Method and Materials

The following materials and methods were used in the examples that follow.

High-Throughput Screening for Identification of CFTR Inhibitors

Screening was performed using an integrated system (Beckman) consisting of a 3-meter robotic arm, CO$_2$ incubator, plate washer, liquid handling work station, barcode reader, delidding station, plate sealer and two fluorescence plate readers (Optima, BMG Lab Technologies), each equipped with two syringe pumps and HQ500/20X (500±10 nm) excitation and HQ535/30M (535±15 nm) emission filters (Chroma).

One hundred thousand small molecules (most 350-550 daltons) were selected for screening from commercial sources (ChemBridge and ChemDiv, both of San Diego, Calif.) using algorithms designed to maximize chemical diversity and drug-like properties. The compounds were obtained as a dried powder and solutions were made in DMSO just before testing, stored frozen as 2.5 mM stock solutions for further use.

Fisher Rat Thyroid (FRT) cells stably expressing wildtype human CFTR and YFP-H148Q were cultured on 96-well black wall plates as described previously (Ma et al., J. Biol. Chem., 277:37235-37241, 2002). For screening, cells in 96-well plates were washed three times and then CFTR halide conductance was activated by incubation for 15 minutes with an activating cocktail containing 10 µM forskolin, 20 µM apigenin and 100 µM isobutylmethyl-xanthine (IBMX). Test compounds (final 25 µM) were added 5 minutes prior to assay of iodide influx in which cells were exposed to a 100 mM inwardly-directed iodide gradient. YFP fluorescence was recorded for 2 seconds prior to and 12 seconds after creation of the iodide gradient. Initial rates of iodide influx were computed from the time course of decreasing fluorescence after the iodide gradient (Yang et al., J. Biol. Chem., 35079-35085, 2003).

Short-Circuit Current Measurements

FRT, T84 colon epithelial cells and human airway epithelial cells were cultured on Snapwell filters with 1 cm$^2$ surface area (Corning-Costar) to resistances>1,000 Ω·cm$^2$ as described previously (Ma et al., J. Biol. Chem., 277:37235-37241, 2002). Filters were mounted in an Easymount Chamber System (Physiologic Instruments, San Diego). For apical Cl$^-$ current measurements on FRT cells, the basolateral hemichamber was filled with buffer containing (in mM): 130 NaCl, 2.7 KCl, 1.5 KH$_2$PO$_4$, 1 CaCl$_2$, 0.5 MgCl$_2$, 10 Na-HEPES, 10 glucose (pH 7.3). The basolateral membrane was permeabilized with amphotericin B (250 µg/ml) just prior to measurements. In the apical solution 65 mM NaCl was replaced by sodium gluconate, and CaCl$_2$ was increased to 2 mM. For short-circuit current measurements in (non-permeabilized) T84 and human airway cells, both hemichambers contained Kreb's solution (in mM): 120 NaCl, 25 NaHCO$_3$, 3.3 KH$_2$PO$_4$, 0.8 K$_2$HPO$_4$, 1.2 MgCl$_2$, 1.2 CaCl$_2$ and 10 glucose (pH 7.3). Solutions were bubbled with 95% O$_2$ and 5% $CO_2$ and maintained at 37° C. For studies in mouse intestine, ileal segments were isolated, washed with ice-cold Kreb's buffer, opened longitudinally through the mesenteric border, and mounted in a micro-Ussing chamber (0.7 $cm^2$ aperture area, World Precision Instruments). Hemichambers were filled with Kreb's solutions containing 10 μM indomethacin. Apical $Cl^-$/short-circuit current were recorded using a DVC-1000 voltage-clamp (World Precision Instruments) with Ag/AgCl electrodes and 1 M KCl agar bridges.

Patch-Clamp Analysis

Patch-clamp experiments were carried out at room temperature on FRT cells stably expressing wildtype CFTR. Cell-attached and whole-cell configurations were used (Hamill et al., *Pflugers Arch.* 391:85-100, 1981). The cell membrane was clamped at specified voltages using an EPC-7 patch-clamp amplifier (List Medical). Data were filtered at 500 Hz and digitized at 2000 Hz. For whole-cell experiments the pipette solution contained (in mM): 120 CsCl, 10 TEA-Cl, 0.5 EGTA, 1 $MgCl_2$, 40 mannitol, 10 Cs-HEPES and 3 mM MgATP (pH 7.3). For cell attached experiments EGTA was replaced with 1 mM $CaCl_2$. The bath solution for whole-cell experiments contained (in mM): 150 NaCl, 1 $CaCl_2$, 1 $MgCl_2$, 10 glucose, 10 mannitol, 10 Na-TES (pH 7.4). In cell-attached experiments the bath solution contained (in mM): 130 KCl, 2 NaCl, 2 $CaCl_2$, 2 $MgCl_2$, 10 glucose, 20 mannitol, and 10 K-Hepes (pH 7.3). Inhibitors were applied by extracellular perfusion. CFTR channel activity in cell-attached patches was analyzed as described previously (Taddei et al., *FEBS Lett.* 558:52-56, 2004).

Nasal Potential Difference Measurements in Mice

Following anesthesia with intraperitoneal ketamine (90-120 mg/kg) and xylazine (5-10 mg/kg) the airway was protected by orotracheal intubation with a 21-gauge angiocatheter as described. A PE-10 cannula pulled to a tip diameter of 0.3 mm was inserted into one nostril 5 mm distal to the anterior nares and connected though a 1M KCl agar bridge to a Ag/AgCl electrode and high-impedance digital voltmeter (IsoMillivolt Meter, World Precision Instruments). The nasal cannula was perfused at 50 μL/min using dual microperfusion pumps serially with PBS, low chloride PBS (chloride replaced by gluconate), low chloride PBS containing forskolin (10 μM) without and then with GlyH-101 (10 μM), and then PBS. In some studies GlyH-101 (10 μM) or 4,4'-di-isothiocyanostilbene-2,2'-disulfonic acid (DIDS) (100 μM) was present in all solutions. The reference electrode was a PBS-filled 21-gauge needle inserted in the subcutaneous tissue in the abdomen and connected to a second Ag/AgCl electrode by a 1M KCl agar bridge.

Intestinal Fluid Secretion Measurements

Mice (CD1 strain, 25-35 g) were deprived of food for 24 hr and anaesthetized with intraperinoneal ketamine (40 mg/kg) and xylazine (8 mg/kg). Body temperature was maintained at 36-38° C. using a heating pad. Following a small abdominal incision 3 closed ileal loops (length 20-30 mm) proximal to the cecum were isolated by sutures. Loops were injected with 100 μl of PBS or PBS containing cholera toxin (1 μg) without or with GlyH-101 (2.5 μg). The abdominal incision was closed with suture and mice were allowed to recover from anesthesia. At 4 hours, the mice were anesthestized, intestinal loops were removed, and loop length and weight were measured to quantify net fluid secretion.

Cholera Models

For closed loop studies, mice (CD1 strain, 28-34 g) were deprived of food for 24 hours and then anaesthetized with intraperinoneal ketamine (40 mg/kg) and xylazine (8 mg/kg). Body temperature was maintained at 36-38° C. using a heating pad. Following a small abdominal incision three closed mid-jejunal loops (length 15-20 mm) were isolated by sutures. Loops were injected with 100 μl of PBS or PBS containing cholera toxin (1 μg) without or with test compounds. The abdominal incision was closed with suture and mice were allowed to recover from anesthesia. At 4 hours the mice were anesthestized, intestinal loops were removed, and loop length and weight were measured to quantify net fluid secretion. Mice were sacrificed by an overdose of ketamine and xylazine. All protocols were approved by the UCSF Committee on Animal Research.

Intestinal Absorption Studies

Absorption studies were performed using mid-jejunal loops created as described above. Loops were injected separately with MalH-1, MalH-2, MalH-3, MalH-(PEG)$_n$, and GlyH-(PEG)$_n$ containing 10-20 μg of test compounds together with 5 μg FITC-dextran (40 kDa). After 2 hours loop fluid was withdrawn and optical absorbance of test compound and FITC were measured ($OD_{342}/OD_{494nm}$). Percentage intestinal absorption was computed assuming zero absorption of FITC-dextran.

Synthesis of Compounds

The synthesis of compounds of the invention are exemplified with but not limited to the following examples. All synthesized compounds were >98% pure (TLC/HPLC) and were confirmed by mass and $^1$H nmr spectrometry.

Synthesis of N-2-napthalenyl-[(3,5-dibromo-2,4-dihydroxyphenyl)methylene]glycine hydrazide (GlyH-101) and related glycine hydrazides (GlyH-102-109, 114-127)

A mixture of 2-napthylamine (compound I, FIG. 3B) (1.43 g, 10 mmol), ethyl iodoacetate (2.14 g, 10 mmol), and sodium acetate (1.64 g, 20 mmol, dissolved in 2 ml of water) was stirred at 90° C. for 3 hours. The solid material obtained upon cooling was filtered and recrystallized from hexane to yield 1.5 g ethyl N-(2-naphthalenyl)glycinate (compound II, FIG. 3B) (yield, 65%, mp 83-84° C.) (Ramamurthy and Bhatt, *J. Med. Chem.* 32:2421-2426, 1989). A solution of above product (2.29 g, 10 mmol) in ethanol (10 ml) was refluxed with hydrazine hydrate (0.6 g, 12 mmol) for 10 hours. Solvent and excess reagent were distilled under vacuum. The product was recrystallized from ethanol to yield 1.8 g of N-(2-naphthalenyl) glycine hydrazide (compound III, FIG. 3B) (yield 82%, mp 147-148° C.). A mixture of compound III (2.15 g, 10 mmol) and 3,5-dibromo-2,4-dihydroxybenzaldehyde (3 g, 10 mmol) in ethanol (5 ml) was refluxed for 3 hours. The hydrazone that crystallized upon cooling was filtered, washed with ethanol, and recrystallized from ethanol to give 3.8 g (78%) of GlyH-101. Melting point (mp)>300° C., ms ($ES^-$): M/Z 492 ($M^-$); $^1$H nmr (DMSO-$d_6$): δ 4.1 (s, 2H, $CH_2$), 6.5-7.5 (m, 9H, aromatic, NH), 8.5 (s, 1H, CH=N), 10.4 (s, 1H, NH—CO), 11.9 (s, 1H, OH), 12.7 (s, 1H, OH). Compounds GlyH-102-109, GlyH-114-127 and AceH401-404 were synthesized similarly by condensing appropriate hydrazides with substituted benzaldehydes.

Synthesis of N-(6-quinolinyl)-[(3,5-dibromo-2,4-dihydroxyphenyl)methylene]glycine hydrazide (GlyH-126) and related quinolinyl-glycine hydrazides To a stirred solution of 6-aminoquinoline (compound IV, FIG. 3B) (0.72 g, 5 mmol) in acetonitrile (20 ml) was added 33% aqueous glyoxylic acid (1.85 g, 20 mmole) solution. A solution of $NaBH_3CN$ (0.64 g, 10.2 mmol) in acetonitrile (20 ml) was then added at 3° C. over 20 minutes and the reaction mixture was warmed to room temperature and stirred for 48 hours. Acetonitrile was evaporated under vacuum, water (20 ml) was added to the residue, the solution was alkalinized to pH 9.5, and unreacted amine was extracted with ether. Concentrated HCl (25 ml) was added to the aqueous solution and the mixture was stirred at 25° C. for 1 hour. Solvent was evaporated under vacuum. The resultant residue of N-(6-quinolinyl)glycine was dissolved in dry ethanol (50 ml) saturated with dry HCl, stirred overnight and then refluxed for 3 hours. Ethanol was evaporated, the ester hydrochloride was suspended in dry ether, and ammonia gas was bubbled. The ammonium chloride was filtered and ether was removed by evaporation to give ethyl N-(6-quinolinyl)glycinate (0.5 g, 87%, mp 122-123° C.). N-(6-quinolinyl)glycine hydrazide (compound VI, FIG. 3B), synthesized by hydrazinolysis of the above ester, was reacted with 3,5-dibromo-2,4-dihydroxybenzaldehyde to give GlyH-126. Similar procedures were used for synthesis of GlyH-127.

Synthesis of Oxamic Hydrazides (OxaH-110-113)

The oxamic hydrazides were synthesized by heating a mixture of 2-napthaleneamine with diethyl oxalate in toluene. The resultant N-substituted oxamic acid ethyl ester was treated with hydrazine hydrate followed by condensation with substituted benzaldehydes to yield compounds OxaH-110-113.

Synthesis of 3,5-dibromo-4-hydroxy-[2-(2-napthalenamine)aceto]benzoic acid hydrazide (GlyH-202) and related GlyH-201 and Oxa-203-204

N-(2-naphthalenyl)glycine hydrazide (compound III, FIG. 3B) (2.15 g, 10 mmole) was reacted with 3,5-dibromo-4-hydroxybenzoyl chloride (3.14 g, 10 mmole) (Gilbert et. al., *Eur. J. Med. Chem.*, 17:581-588, 1982) in pyridine (10 ml) for 5 hours. Pyridine was removed and the residue was diluted with water. The product was recrystallized from ethanol to yield a gray powder 3.8 g (77%), mp>300° C. Compounds GlyH-201 and Oxa-203-204 were synthesized by similar procedure.

Synthesis of N-2-napthalenyl-[(3,5-dibromo-2,4-dihydroxyphenyl)methyl]glycine hydrazide (GlyH-301) and related glycine hydrazides (GlyH-302 OxaH-303-304)

A mixture of GlyH-101 (1.5 g, 3 mmole), hydrazine hydrate (0.15 ml, 3 mmol) and Pd/C catalyst (0.1 g, 10% Pd) in 5 ml of dimethylformamide was refluxed for 6-8 hours (Verma et al., *Arch. Pharm.* 317:890-894, 1984). The reaction mixture was filtered, diluted with cold water, and extracted with diethyl ether. GlyH-301 was crystallized from ether to yield 0.9 g (60%), mp 258-260° C. Compounds GlyH-302 and OxaH-303-304 were prepared similarly.

Synthesis of Analogs

The synthesis of analog of the compounds of the invention are exemplified with but not limited to the following examples. All synthesized compounds were >98% pure (TLC/HPLC) and were confirmed by mass and $^1$H nmr spectrometry. $^1$H NMR spectra were obtained in $CDCl_3$ or DMSO-$d_6$ using a 400 MHz Varian Spectrometer referenced to $CDCl_3$ or DMSO. Mass spectrometry was done using a Waters LCMS system (Alliance HT 2790+ZQ, HPLC: Waters model 2960, Milford, Mass.). Flash chromatography was performed using EM silica gel (230-400 mesh), and thin layer chromatography was done on Merk silica gel 60 F254 plates.

Synthesis of Diethyl-(2-naphthalenylamino)-propanedioate (compound 2, FIG. 9)

A mixture of 2-naphthylamine (compound 1, FIG. 9) (10 mmol), diethyl bromomaloante (10 mmol), and sodium acetate (1.64 g, 20 mmol, dissolved in 4 ml of water) was stirred at 90° C. for 8 hours. The black solid material obtained upon cooling was filtered and recrystallized from hexane to yield 2.5 g of 2 (yield 84%); mp, 189-190° C.; ms (ES$^+$): M/Z 302 (M+1)$^+$; $^1$H nmr (DMSO-$d_6$): δ 1.17 (t, 6H, 7.33 Hz), 4.17 (q, 4H, 7.33), 5.10 (d, 1H, 8.79 Hz), 6.54 (d, 1H, 8.79 Hz), 6.75 (d, 1H, 2.20 Hz), 7.13 (t, 1H, 7.32 Hz), 7.19 (dd, 1H, 2.19, 8.79 Hz), 7.28 (t, 1H, 8.06 Hz), 7.51 (d, 1H, 8.42 Hz), 7.61 (t, 2H, 8.79 Hz).

Synthesis of (2-naphthalenylamino)-propanedioic acid dihydrazide (compound 3, FIG. 9)

A solution of compound 2 (FIG. 9) (10 mmol) in ethanol (10 ml) was refluxed with hydrazine hydrate (12 mmol) for 10 hours. Solvent and excess reagent were distilled under vacuum. The product was recrystallized from ethanol to give 2.5 g of compound 3 (92%); mp 268-270° C.; ms (ES$^+$): M/Z 274 (M+1)$^+$; $^1$H nmr (DMSO-$d_6$): δ 4.29 (d, 4H, 4.03), 4.56 (d, 1H, 8.79 Hz), 6.03 (d, 1H, 8.79 Hz), 6.62 (d, 1H, 1.46 Hz), 7.09 (m, 2H), 7.28 (t, 1H, 8.05 Hz), 7.50 (d, 1H, 8.06 Hz), 7.61 (m, 2H), 9.22 (s, 2H).

Synthesis of 2-naphthalenylamino-bis[(3,5-dibromo-2,4-dihydroxyphenyl)methylene]propanedioic acid dihydrazide (MalH-1)

A mixture of compound 3 (FIG. 9) (10 mmol) and 3,5-dibromo-2,4-dihydroxybenzaldehyde (20 mmol) in ethanol (5 ml) was refluxed for 3 hours. The hydrazone that crystallized upon cooling was filtered, washed with ethanol, and purified by column chromatography (silica gel EtOAc:hexane 2:3) to give 3.2 g of compound 4 (58%) as an off-white solid; mp 246-248° C.; ms (ES$^+$): M/Z 830 (M+1)$^+$; $^1$H nmr (DMSO-$d_6$): δ 4.91, 5.48 (d, 1H, 7.69, 9.15 Hz), 6.62 (d, 1H, 7.32 Hz), 6.73, 6.84 (s, 1H), 7.13-7.32 (m, 3H), 7.57 (d, 1H, 8.06 Hz), 7.61-7.70 (m, 3H), 7.80, 7.90 (s, 1H), 8.15, 8.37 (s, 2H), 10.10-10.40 (broad s, 2H), 11.72, 11.90 (s, 2H), 12.22, 12.53 (s, 2H).

Synthesis of 2-naphthalenylamino-[(3,5-dibromo-2,4-dihydroxyphenyl)methylene][(2,4-disodium-disulfophenyl)methylene]propanedioic acid dihydrazide (MalH-2)

A mixture of dihydrazide 4 (FIG. 9) (5 mmol) and 2,4-disodium-disulfobenzaldehyde (5 mmol) in DMF (5 ml) was refluxed for 4 hours. The reaction mixture, upon cooling, was added dropwise to a stirred solution of EtOAc:EtOH (1:1), filtered, washed with ethanol, and further purified by column chromatography (silica gel EtOAc:hexane 2:3) to give 2.3 g of compound MalH-2 (58%) as an off-white solid; mp>300° C.; ms (ES$^+$): M/Z 800 (M+1)$^+$; $^1$H nmr (DMSO-$d_6$): δ 4.95, 5.44 (d, 1H, 7.63, 9.16 Hz), 6.64 (d, 1H, 7.31 Hz), 6.70, 6.81 (s, 1H), 7.12-7.44 (m, 4H), 7.59 (d, 1H, 8.00 Hz), 7.64-7.76 (m, 4H), 7.80, 7.90 (s, 1H), 8.25, 8.37 (s, 2H), 10.36 (broad s, 1H), 11.62, 11.82 (s, 1H), 12.11, 12.43 (s, 2H).

2-naphthalenylamino-[(3,5-dibromo-2,4-dihydroxyphenyl)methylene][3-(4-sodium-sulfophenyl)-thioureido]propanedioic acid dihydrazide (MalH-3) and 2-naphthalenylamino-[(3,5-dibromo-2,4-dihydroxyphenyl)methylene][3-[4-(3-(PEG)$_n$-thioureido)phenyl)-thioureido]propanedioic acid dihydrazide (MalH-(PEG)$_n$) were synthesized following similar reaction conditions used for MalH-2 except that 4-sodium-sulfophenylisothiocyanate and compound 6 (FIG. 10) were used respectively, in place of 2,4-disodium-disulfobenzaldehyde.

MalH-3: mp>300° C.; ms (ES$^-$): M/Z 765 (M−1)$^+$; $^1$H nmr (DMSO-d$_6$): δ 4.90, 5.31 (d, 1H, 7.61, 9.12 Hz), 6.54 (d, 1H, 7.31 Hz), 6.70, 6.81 (s, 1H), 7.12-7.44 (m, 4H), 7.59 (d, 1H, 8.00 Hz), 7.64-7.76 (m, 4H), 7.90 (d, 2H), 8.25, 8.37 (s, 1H), 9.88 (s, 1H) 10.05 (s, 1H, CSNH), 10.36 (s, 1H, OH), 11.11, 11.43 (s, 2H, CONH), 11.62, 11.82 (s, 1H, OH).

MalH-(PEG)$_1$: mp>300° C.; ms (ES$^+$): M/Z 849 (M+1)$^+$; $^1$H nmr (DMSO-d$_6$): δ 3.70-4.37 (m, 8H), 4.81, 5.01 (d, 1H, 7.51, 9.13 Hz), 5.27 (s, 1H), 6.60 (d, 1H, 7.31 Hz), 6.75 (s, 1H), 7.19-7.38 (m, 4H), 7.59 (d, 2H, 8.00 Hz), 7.64-7.76 (m, 3H), 7.90 (d, 2H, 8.00 Hz), 8.21, 8.30 (s, 1H), 9.76 (s, 2H) 9.83 (s, 1H), 10.01 (s, 1H), 10.36 (s, 1H), 11.20, 11.51 (s, 2H), 11.54, 11.62 (s, 1H).

Synthesis of 2-[3-(4-isothiocyanato-phenyl)-thioureido]ethyl-(PEG)$_1$ (compound 6a, FIG. 10)

To a solution of 1,4-phenylene diisothiocyanate (1 mmol, 2 mL DMF) was added 2-aminoethoxyethanol (0.3 mmol, 2 mL DMF) over 30 minutes. After stirring for additional 30 minutes, the DMF was distilled off and product was purified by column chromatography on silica gel using as solvent n-hexane:AcOEt (1:1). Fractions were evaporated to give 58 mg of compound 2 in (65%); ms (ES$^+$): M/Z 298 (M+1)$^+$; $^1$H nmr (DMSO-d$_6$): δ 2.84 (t, 2H, 6.46 Hz), 2.95 (t, 2H, 6.31 Hz), 3.12 (t, 2H, 6.38 Hz), 3.58 (q, 2H, 5.98 Hz), 5.63 (s, 1H), 7.15 (d, 2H, 8.62 Hz), 7.44 (d, 2H, 8.62 Hz), 7.97 (s, 2H, NH). Similarly, compound 6b was synthesized using appropriate amino-PEG; yield, 58%; ms (ES): M/Z 736 (+/−44, 88, 132, 176) (M+1); $^1$H nmr (DMSO-d$_6$): δ 3.24 (s, 3H), 3.31-3.82 (m), 7.21 (d, 2H, 8.60 Hz), 7.47 (d, 2H, 8.60 Hz), 7.92 (s, 2H).

Synthesis of 2-(2-naphthalenylamino)-4-hydroxy-butyric acid hydrazide (compound 7, FIG. 11)

This compound was synthesized following similar reaction conditions used for compounds 2 and 3.89%; mp 258-260° C.; ms (ES$^+$): M/Z 260 (M+1)$^+$; $^1$H nmr (DMSO-d$_6$): δ 1.79 (m, 2H) 3.46 (q, 2H) 3.98 (s, 1H), 4.17 (d, 2H) 4.52 (t, 1H), 5.94-5.96 (s, 1H), 6.68 (s, 1H), 6.98 (dd, 1H), 7.05 (t, 1H), 7.24 (t, 1H), 7.46 (d, 1H), 7.52-7.60 (m, 2H) 9.17 (s, 1H).

Synthesis of [2-(2-naphthalenylamino)-4-hydroxy]butyric acid-2-[(1,1-dimethylethoxy)carbonyl]hydrazide (compound 8, FIG. 11)

To a solution of hydrazide 7 (10 mM) in THF (10 ml) was added (BOC)$_2$O (20 mM) and heated under reflux for 5 hours. The solvent was removed, and the residue was purified by column chromatography on silica gel. Elution with dichloromethane gave 3.1 g of compound 8 (86%) as a white solid; mp 235-237° C.; ms (ES$^+$): M/Z 360 (M+1)$^+$; $^1$H nmr (DMSO-d$_6$): δ 1.33 (s, 9H), 1.92 (m, 2H), 3.52 (q, 2H), 4.01 (q, 1H), 4.52 (t, 1H), 6.00 (d, 1H), 6.70 (s, 1H), 6.97 (dd, 1H), 7.06 (t, 1H), 7.25 (t, 1H), 7.45 (d, 1H), 7.52-7.59 (m, 2H), 8.73 (s, 1H), 9.77 (s, 1H).

Synthesis of [2-(2-naphthalenylamino)-4-(p-tosyl)]butyric acid-2-[(1,1-dimethylethoxy)carbonyl]hydrazide (compound 9, FIG. 11)

To a solution of hydrazide 7 (1 mmol) in pyridine (5 ml) was added p-TsCl (1 mmol) in three portions 30 min apart (−15° C.). The reaction mixture was stirred for 8 hours at −15° C., allowed to warm to room temperature, diluted with 1N HCl, and extracted three times with EtOAc. The combined organic extract was washed with brine, dried with Na$_2$SO$_4$ and evaporated to dryness to give 374 mg of compound 9 (73%) as a pale yellow oil, used without further purification for next step; ms (ES$^+$): M/Z 514 (M+1)$^+$.

Synthesis of [2-(2-naphthalenylamino)-4-(PEG-amino)]butyric acid-2-[(1,1-dimethylethoxy)carbonyl]hydrazide (compound 10, FIG. 11)

A solution of 2-aminoethoxyethanol (1 mM) and compound 9 (1 mM) in DMF (2 ml) was stirred at 80° C. for 24 hours. The DMF was evaporated in vacuo, and the residue was dissolved in minimum quantity of EtOAc and added to a stirred solution of Et$_2$O. The white powder-like precipitate was filtered and washed with Et$_2$O to give 170 mg of compound 9 (38%) as a yellow sticky mass; ms (ES$^+$): M/Z 447 (M+1)$^+$; $^1$H nmr (DMSO-d$_6$): δ 1.35 (s, 9H), 1.71 (m, 2H) 3.40-3.51 (m, 4H), 3.57 (t, 2H), 3.68-3.79 (m, 5H, CH2), 3.93 (s, 1H), 4.52 (t, 1H), 6.04, 6.16 (s, 1H), 6.67 (s, 1H), 6.93 (dd, 1H), 7.03 (t, 1H), 7.32 (t, 1H), 7.45 (d, 1H), 7.50-7.62 (m, 2H), 9.27 (s, 1H), 9.89 (s, 1H).

Synthesis of [2-(2-naphthalenylamino)-4-(PEG-amino)]butyric acid hydrazide (compound 11, FIG. 11)

Hydrazide 10 (1 mM) was dissolved in a minimal amount of trifluoroacetic acid:CH$_2$Cl$_2$ (1:1) and stirred at room temperature for 30 minutes. The reaction mixture was diluted with saturated aqueous NaHCO$_3$ and extracted with CH$_2$Cl$_2$. The combined organic layer was washed successively with water and brine, dried (Na$_2$SO$_4$), and concentrated in vacuo to yield 253 mg of compound 11 (73%) as yellow semisolid; ms (ES$^+$): M/Z 347 (M+1)$^+$; $^1$H nmr (DMSO-d$_6$): $^1$H nmr (DMSO-d$_6$): $^1$H nmr (DMSO-d$_6$): δ 1.71 (m, 2H) 3.40-3.51 (m, 4H), 3.57 (t, 2H), 3.68-3.79 (m, 5H, CH2), 3.93 (s, 1H), 4.26 (d, 2H) 4.52 (t, 1H), 6.02, 6.21 (s, 1H), 6.71 (s, 1H), 6.85 (dd, 1H), 7.10 (t, 1H), 7.34 (t, 1H), 7.51 (d, 1H), 7.53-7.76 (m, 2H), 9.27 (s, 1H).

Synthesis of [2-(2-naphthalenylamino)-4-(PEG-amino)]butyric acid-2-[(3,5-dibromo-2,4-dihydroxyphenyl)methylene]hydrazide (compound 12, FIG. 11)

A mixture of compound 11 (1 mmol) and 3,5-dibromo-2, 4-dihydroxybenzaldehyde (1 mmol) in ethanol (2 ml) was refluxed for 3 hours. The reaction mixture was concentrated and added to a stirred solution of Et$_2$O, and the precipitated hydrazone was filtered and washed with Et$_2$O to yield 362 mg of compound 12 (58%); ms (ES$^+$): M/Z 625 (M+1)$^+$; $^1$H nmr (DMSO-d$_6$): $^1$H nmr (DMSO-d$_6$): δ 1.75 (m, 2H) 3.43-3.48 (m, 4H), 3.59 (t, 2H), 3.72-3.81 (m, 5H, CH2), 3.97 (s, 1H), 4.59 (t, 1H), 6.12, 6.26 (s, 1H), 6.75 (s, 1H), 6.85-6.96 (m, 2H), 7.15-7.51 (t, 3H), 7.53-7.76 (m, 2H), 8.87 (s, 1H), 9.27 (s, 1H), 10.68 (s, 1H), 11.92 (s, 1H).

Example 1

Discovery of Novel Classes of CFTR Inhibitors

A collection of 100,000 small, drug-like compounds was screened to identify new CFTR inhibitors. As diagrammed in FIG. 1A, compounds were screened at 25 µM in a cell-based assay of iodide influx after CFTR activation by an agonist mixture containing forskolin, IBMX and apigenin. Initial rates of iodide influx were computed from the kinetics of fluorescence decrease following chloride replacement by iodide. Four compounds (FIG. 1B) reducing iodide influx by greater than 50% were identified, which were not related structurally to known CFTR activators or inhibitors. Twelve compounds reduced iodide influx by 25-50%, most of which were related structurally to the compounds in FIG. 1B or to the thiazolidinones.

Figure 1C:
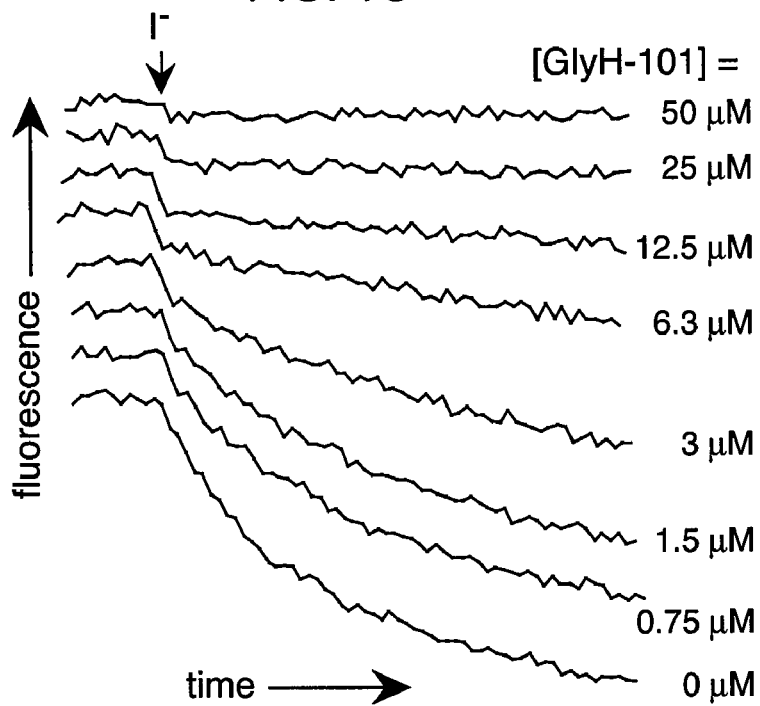
Figure 1D:
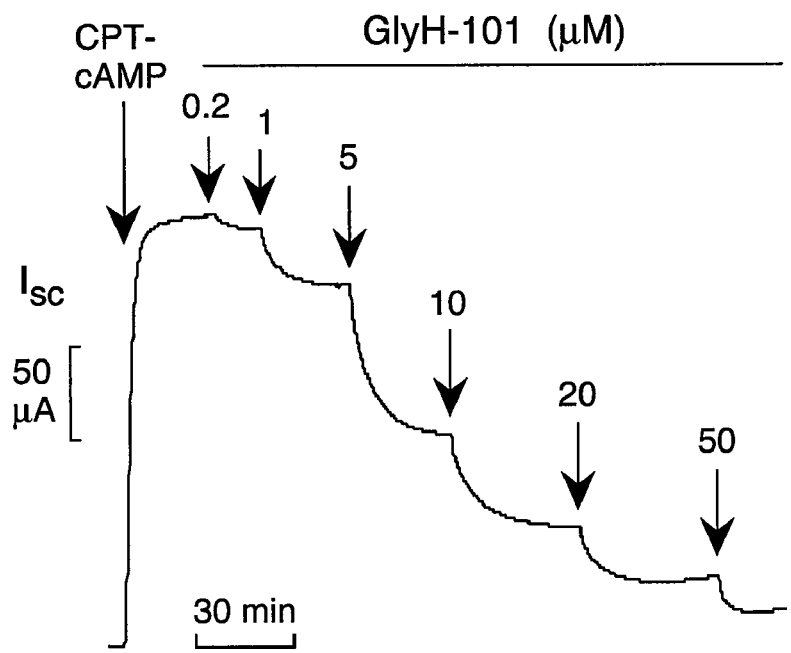

To select inhibitor(s) for further evaluation, dose-response measurements were done for the compounds in FIG. 1B, and CFTR inhibition was confirmed electrophysiologically by short-circuit current analysis. $K_i$ was ~7, 5, 5 and 5 µM for compounds a-d, respectively. FIG. 1C shows representative fluorescence and FIG. 1D shows a representation of short-circuit current data for compound d. 100-250 commercially available analogs of each compound class were screened to determine whether active structural analogs exist, an important prerequisite for follow-up compound optimization by synthesis of targeted analogs. Whereas few or no active analogs of compounds a, b and c were found, initial screening of 285 analogs of compound d (substituted glycine hydrazides, GlyH) revealed 34 analogs that inhibited CFTR-mediated iodide influx by >25% at 25 µM.

Figure 2A:
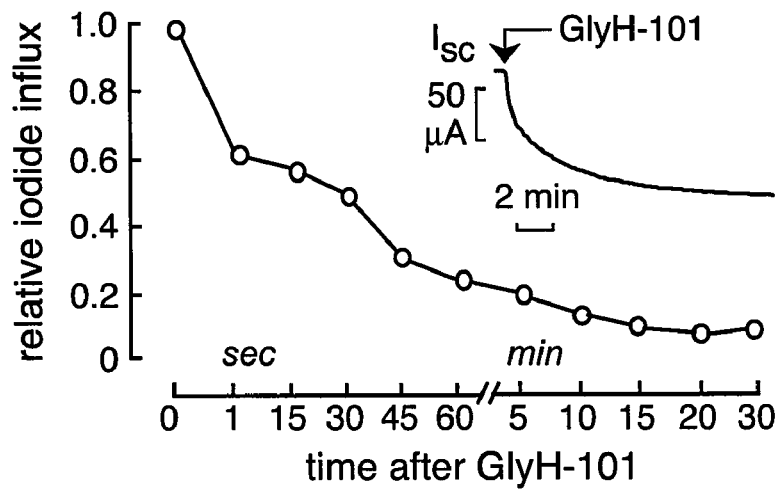
FIG. 2A is a graph representing the time course of inhibition showing CFTR-mediated I⁻ transport rates at different times after addition of 10 μM GlyH-101.
Figure 2B:
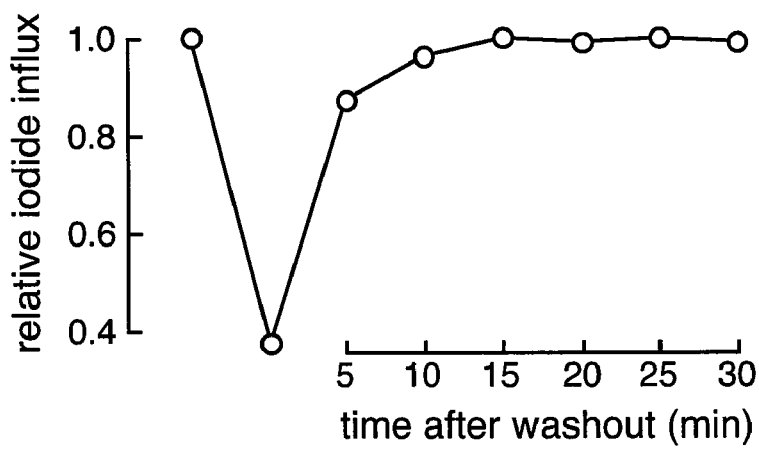
FIG. 2B is a graph representing the time course of inhibition reversal showing I⁻ transport rates at different times after washout of GlyH-101.
Figure 2C:
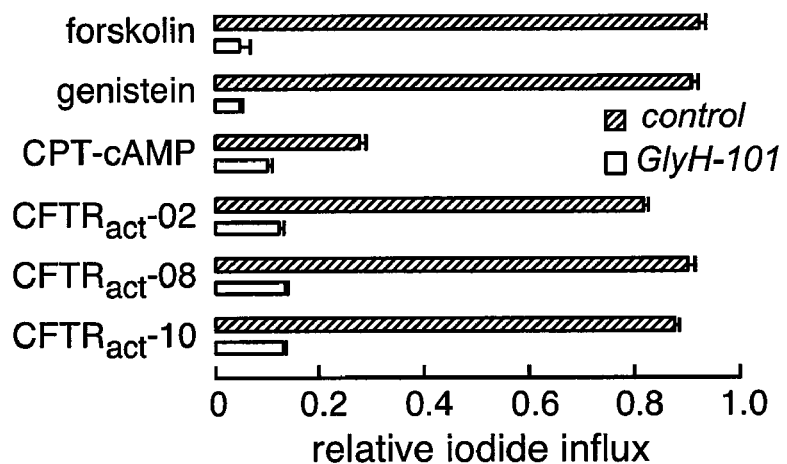
FIG. 2C is a graph representing iodide influx by GlyH-101 (50 μM) after CFTR stimulation by indicated agonists (50 μM). Filled bars show agonist, and open bars show agonist with GlyH-101.

The structure-activity analysis and characterization of inhibition mechanism, as well as the time course of action and reversibility of action of synthesized GlyH analogs was determined. In addition, the effectiveness of the analogs for different CFTR activating mechanisms was also analyzed. FIG. 2A shows prompt inhibition of iodide influx in the fluorescence and short-circuit current assays upon GlyH-101 addition. Interestingly 50% of the inhibition occurred within the ~1 second addition/mixing time, with further inhibition over ~1 minute. FIG. 2B indicates complete reversal of inhibition after GlyH-101 washout with >75% reversal over 5 minutes. FIG. 2C shows effective CFTR inhibition by GlyH-101 after activation by different types of agonists, including potent direct activators of CFTR that do not elevate cytosolic cAMP or inhibit phosphatase activity (CFTR$_{act}$-01, 08, and 10; Ma et al., *J. Clin. Invest.* 110:1651-1658, 2002).

Example 2

Chemistry and Structure-Activity Relationships of Glycine Hydrazides

The GlyH-101 structure was modified systematically to establish structure-activity relationships and to identify analogs with improved CFTR inhibitory activity. FIG. 3A shows the various classes of structural analogues that were synthesized and tested for CFTR inhibition. Structural modifications were performed on both ends of the glycine hydrazide backbone (FIG. 3A, left, top and middle). Replacing the glycine methylene group by a carbonyl group and replacing nitrogen by oxygen generated oxamic acid hydrazides (OxaH, right, top) and acetic acid hydrazides (AceH, right, middle), respectively. The hydrazone group modification produced two important series of compounds (middle, bottom and right, bottom). Also shown are compounds containing an additional methyl group at the hydrazone bond (top, middle), and containing a 6-qunolinyl group replacing the naphthalenyl group (left, bottom).

FIG. 3B shows the reaction schemes developed for synthesis of the different classes of glycine hydrazide analogs. Synthesis of GlyH-101 involves reaction of 2-naphthalemine with ethyl iodoacetate followed by reactions with hydrazine hydrate and 2,4-dihydroxy-3,5-dibromobenzaldehyde. A similar procedure was used for most of the remaining glycine hydrazide derivatives (listed in Table 1). The heteroaromatic analogues containing a 6-qunolinium group required different synthetic route in which 6-aminoquinoline was condensed with glyoxalic acid, and reduced using sodium cyanoborohydride (yielding N-6-quinolineglycine, Ramamurthy et al., 1989), which was further esterified and reacted with hydrazine hydrate and benzaldehyde. The oxamic acid hydrazides were synthesized starting from aromatic amines and diethyl oxalate.

Modifications were made initially on the N-aryl ($R_1$) and benzaldehyde ($R_2$) positions (see Tables 1-4 for R- and X-group definitions and CFTR inhibition). Good CFTR inhibition was found when $R_2$ contained 3,5-dibromo and at least one hydroxyl substituent at the 4-position (GlyH-102, 105, 114); addition of a second hydroxyl group increased inhibition (GlyH-101, 104, 115-116). Inhibition was reduced when $R_2$ contained 4-bromophenyl or 4-carboxyphenyl substituents (GlyH-120-121). In addition, the 4-hydroxyl group in GlyH-101 was important for inhibition since its 4-methoxy analogue GlyH-103 had little activity. Similar structure-activity results were found for GlyH-115 and GlyH-122.

$R_1$ group modifications were carried out, maintaining $R_2$ as 2,4-dihydroxy-3,5-dibromophenyl and 3,5-dibromo-4-hydroxyphenyl. Analogues with $R_1$ as 2-naphthalenyl were much better inhibitors than $R_1$ as 4-chlorophenyl or 4-methylphenyl. Replacement of the 2-napthalenyl of GlyH-101 by 1-napthalenyl (GlyH-104) decreased inhibition activity tenfold, supporting the requirement of the 2-naphthalenyl substituent. GlyH-124-125, containing a 2-anthacenyl group, were less active. Replacement of 2-naphthalenyl group in GlyH-101 and GlyH-102 by more polar heteroaromatic rings such as 6-qunolinyl gave compound with little activity (GlyH-126-127), as did the 2-naphthoxy analogues AceH-401 and AceH-402.

X was next modified (replacing methylene), keeping 2-naphthalenyl as $R_1$ and dibromo-dihydroxyphenyl as $R_2$. Introduction of a carbonyl group in GlyH-101 and GlyH-102 at X, giving OxaH-110 and OxaH-111, gave two-three fold greater inhibitory potency. FIG. 3C shows short-circuit current analysis of CFTR inhibition for the most active analog OxaH-110, with an apparent $K_i$~2 µM. Replacement of $CH_2$ by $CHCH_3$ (GlyH-106-107) also improved CFTR inhibition. In another structural variation, addition of a methyl group at $R_3$ to GlyH-102, yielding GlyH-109, gave improved CFTR inhibition. Modification of the N=C group in GlyH-101 and GlyH-102 to NH—$CH_2$ in GlyH-301 and GlyH-302, or to NH—CO in GlyH-201 and GlyH-202, reduced CFTR inhibitory potency.

TABLE 1

Structure-activity relationships of Group 1 hydrazide-containing compounds
Group I $$R_1-\overset{H}{N}-X-\overset{O}{\overset{\|}{C}}-\overset{H}{N}-N=\overset{R_2}{\underset{R_3}{C}}$$ (I)

| Compound | $R_1$ | X | $R_2$ | $R_3$ | $K_i$ (μM) | % inhibition at 50 μM |
|---|---|---|---|---|---|---|
| GlyH-101 | 2-naphthalenyl | CH$_2$ | 3,5-di-Br-2,4-di-OH—Ph | H | 5 | 95 |
| GlyH-102 | 2-naphthalenyl | CH$_2$ | 3,5-di-Br-4-OH—Ph | H | 5 | 98 |
| GlyH-103 | 2-naphthalenyl | CH$_2$ | 3,5-di-Br-2-OH-4-OMe—Ph | H | 20 | 56 |
| GlyH-104 | 1-naphthalenyl | CH$_2$ | 3,5-di-Br-2,4-di-OH—Ph | H | 12 | 86 |
| GlyH-105 | 1-naphthalenyl | CH$_2$ | 3,5-di-Br-4-OH—Ph | H | 15 | 87 |
| GlyH-106 | 2-naphthalenyl | CHCH$_3$ | 3,5-di-Br-2,4-di-OH—Ph | H | 6 | 91 |
| GlyH-107 | 2-naphthalenyl | CHCH$_3$ | 3,5-di-Br-4-OH—Ph | H | 10 | 80 |
| GlyH-108 | 2-naphthalenyl | CH$_2$ | 3,5-di-Br-2,4-di-OH—Ph | CH$_3$ | 10 | 81 |
| GlyH-109 | 2-naphthalenyl | CH$_2$ | 3,5-di-Br-4-OH—Ph | CH$_3$ | 2.5 | 100 |
| OxaH-110 | 2-naphthalenyl | CO | 3,5-di-Br-2,4-di-OH—Ph | H | 2 | 86 |
| OxaH-111 | 2-naphthalenyl | CO | 3,5-di-Br-4-OH—Ph | H | 2.5 | 52 |
| OxaH-112 | 2-naphthalenyl | CO | 3,5-di-Br-2,4-di-OH Ph | CH$_3$ | 3 | 95 |
| OxaH-113 | 2-naphthalenyl | CO | 3,5-di-Br-4-OH—Ph | CH$_3$ | 3 | 90 |
| GlyH-114 | 4-Cl—Ph | CH$_2$ | 3,5-di-Br-4-OH—Ph | H | 5 | 95 |
| GlyH-115 | 4-Cl—Ph | CH$_2$ | 3,5-di-Br-2,4-di-OH Ph | H | 5 | 91 |
| GlyH-116 | 4-Me—Ph | CH$_2$ | 3,5-di-Br-2,4-di-OH Ph | H | 10 | 79 |
| GlyH-117 | 2-Me—Ph | CH$_2$ | 3,5-di-Br-2,4-di-OH Ph | H | | |
| GlyH-118 | 1-naphthalenyl | CH$_2$ | 3-Br-4-OH—Ph | H | | |
| GlyH-119 | 2-naphthalenyl | CH$_2$ | 2,4-di-OH—Ph | H | | |
| GlyH-120 | 2-naphthalenyl | CH$_2$ | 4-Br—Ph | H | | |
| GlyH-121 | 2-naphthalenyl | CH$_2$ | 4-carboxy-Ph | H | | |
| GlyH-122 | 4-Cl—Ph | CH$_2$ | 3,5-di-Br-2-OH-4-OMe—Ph | H | | |
| GlyH-123 | 4-Cl—Ph | CH$_2$ | 2,4-di-OH—Ph | H | | |
| GlyH-124 | 2-anthracenyl | CH$_2$ | 3,5-di-Br-2,4-di-OH Ph | H | | |
| GlyH-125 | 2-anthracenyl | CH$_2$ | 3,5-di-Br-4-OH—Ph | H | | |
| GlyH-126 | 6-quinolinyl | CH$_2$ | 3,5-di-Br-2,4-di-OH Ph | H | | |
| GlyH-127 | 6-quinolinyl | CH$_2$ | 3,5-di-Br-4-OH—Ph | H | | |

Glycine hydrazides (GlyH, X = CH$_2$)
Oxamic acid hydrazides (OxaH, X = CO)

TABLE 2

Structure-activity relationships of Group 2 hydrazide-containing compounds
Group II $$R_1-\overset{H}{N}-X-\overset{O}{\overset{\|}{C}}-\overset{H}{N}-\overset{H}{N}-\overset{O}{\overset{\|}{C}}-R_2$$ (II)

| Compound | $R_1$ | X | $R_2$ | $K_i$ (μM) | % Inhibition at 50 μM |
|---|---|---|---|---|---|
| GlyH-201 | 2-naphthalenyl | CH$_2$ | 3,5-di-Br-2,4-di-OH Ph | 20 | 65 |
| GlyH-202 | 2-naphthalenyl | CH$_2$ | 3,5-di-Br-4-OH—Ph | 22 | 57 |
| OxaH-203 | 2-naphthalenyl | CO | 3,5-di-Br-2,4-di-OH Ph | >50 | |
| OxaH-204 | 2-naphthalenyl | CO | 3,5-di-Br-4-OH—Ph | >50 | |

$R_1$ = Ph, Monosubstituted-Ph: Aklyl. halo, alkoxy.
Disubstituded-Ph: Dihalo, hydroxy + alkoxy.
Trisubstituted-Ph: Trihalo, dihalo + alkyl
$R_2$ = Ph, Monosubstituted-Ph: alkyl, halo, alkoxy, aryloxy, aryl, nitro. hydroxy, dialkylamino,
Disubstituted-Ph: dihalo, dihydroxy, dialkyl, halo + alkyl, hydroxy + alkoxy, dialkoxy
Trisubstituted-Ph: alkyl/alkoxy + halo + hydroxy

TABLE 3

Structure-activity relationships of Group 3 hydrazide-containing compounds
Group III $$R_1 \underset{H}{N} X \underset{}{\overset{O}{\underset{N}{\|}}} \underset{H}{N} R_2 \quad (III)$$

| Compound | $R_1$ | X | $R_2$ | $K_i$ (µM) | % Inhibition at 50 µM |
|---|---|---|---|---|---|
| GlyH-301 | 2-naphthalenyl | $CH_2$ | 3,5-di-Br-2,4-di-OH Ph | ~50 | 50 |
| GlyH-302 | 2-naphthalenyl | $CH_2$ | 3,5-di-Br-4-OH—Ph | ~50 | 55 |
| OxaH-303 | 2-naphthalenyl | CO | 3,5-di-Br-2,4-di-OH Ph | 10 | 70 |
| OxaH-304 | 2-naphthalenyl | CO | 3,5-di-Br-4-OH—Ph | 12 | 78 |

TABLE 4

Structure-activity relationships of Group 4
hydrazide-containing compounds
Group IV $$R_1 \overset{O}{\underset{}{\|}} \underset{H}{N} N = R_2 \quad (IV)$$

| Compound | $R_1$ | $R_2$ | $K_i$ (µM) | % Inhibition at 50 µM |
|---|---|---|---|---|
| AceH-401 | 2-naphthoxy | 3,5-di-Br-2,4-di-OH Ph | 21 | 84 |
| AceH-402 | 2-naphthoxy | 3,5-di-Br-4-OH—Ph | 17 | 86 |
| AceH-403 | 4-Me—Ph | 3,5-di-Br-2,4-di-OH Ph | 10 | 54 |
| AceH-404 | 4-Me—Ph | 3,5-di-Br-4-OH—Ph | 15 | 63 |

Acetic acid hydrazides (AceH)

(Tables 1-4: $K_i$ indicates the concentration giving 50% inhibition of CFTR Cl⁻ conductance by short-circuit current analysis on CFTR-expressing FRT cells.)

Example 3

Patch-Clamp Analysis of CFTR Inhibition Mechanism

The mechanism of CFTR block by GlyH-101 was studied using the whole-cell configuration of the patch-clamp technique. After maximal activation of CFTR in stably transfected FRT cells by 5 µM forskolin, current-voltage relationships were measured at GlyH-101 concentrations from 0 to 50 µM. Representative original current recordings are shown in FIG. 4A. In the absence of inhibitor (left panel), membrane current increased linearly with voltage and did not show relaxation phenomena, as expected for pure CFTR Cl⁻ currents. Extracellular perfusion with 10 µM GlyH-101 produced an immediate reduction in current that was strongly dependent on membrane potential (FIG. 4A, right panel). At more positive membrane potentials outward positive currents (Cl⁻ movement into the cell) were reduced compared to inward currents. FIG. 4B shows current-voltage relationships for GlyH-101 concentrations of 0 (control), 10 and 30 µM, and after washout of 30 µM GlyH-101 (recovery). Data for the thiazolidinone 3-[(3-trifluoromethyl)phenyl]-5-[(4-carboxyphenyl)methylene]-2-thioxo-4-thiazolidinone (referred to herein as $CFTR_{inh}$-172) (5 µM) is shown for comparison. The current-voltage relationship was linear in the absence of inhibitor, after GlyH-101 washout, and after inhibition by $CFTR_{inh}$-172, whereas GlyH-101 inhibition at submaximal concentrations produced inward rectification. FIG. 4C summarizes percentage CFTR current block as a function of GlyH-101 concentration at different membrane voltages. GlyH-101 inhibitory potency was reduced at more negative voltages, with apparent $K_i$ of 1.4, 3.8, 5.0, and 5.6 µM for voltages of +60, +20, −20 and −60 mV, respectively (Hill coefficients, $n_H$=0.5, 0.7, 1.3, 1.8).

Cell-attached patch-clamp experiments were carried out to investigate the mechanism of GlyH-101 block of CFTR Cl⁻ current at the single-channel level. FIG. 4D shows a GlyH-101 concentration-dependent reduction in CFTR channel activity without a change in single channel conductance. Mean channel open time was remarkably reduced with the appearance of brief closures during the open bursts whose frequency increased with GlyH-101 concentration. In the absence of the inhibitor, mean channel open time was 264±11 ms (SE, n=10). Mean channel open times at +60 mV at 0.4, 1, and 5 µM GlyH-101 were reduced to 181±29, 38±5, and 13±2 ms, respectively (n=5; p<0.01 for all concentrations vs. control).

The kinetic and electrophysiological data indicate that hydrazide-containing compounds block CFTR Cl⁻ conductance by occluding the CFTR anion pore at or near the external membrane surface. Unlike all other CFTR inhibitors, including the thiazolidinone $CFTR_{inh}$-172, CFTR block by the hydrazide-containing GlyH-101 produced inwardly rectifying CFTR Cl⁻ currents. Compared to $CFTR_{inh}$-172, GlyH-101 is 50-fold more water soluble and rapidly acting/reversible when added to or removed from the extracellular solution, consistent with its action at the external-facing surface of CFTR. Structure-activity analysis of a series of targeted hydrazide-containing analogs defined the structural determinants for CFTR inhibition and provided analogs with greater CFTR inhibitory potency, the best being OxaH-110 with Ki~2 µM. Although the most potent thiazolidinone $CFTR_{inh}$-172 has Ki of 0.2-0.3 µM in permeabilized cell preparations, its Ki is 2-5 µM in most intact epithelial cells because of the interior negative membrane potential which reduces its concentration in cytoplasm. Thus, the hydrazide-containing compounds are as or more potent than the thiazolidinones, and like the thiazolidinones they block CFTR in nasal and intestinal epithelia in vivo.

Patch-clamp studies indicated that CFTR inhibition by GlyH-101 is sensitive to membrane potential. At sub-maximal concentrations of GlyH-101 there was marked inward rectification in the CFTR current-voltage relationship indicating that Cl⁻ flux from the extracellular to the intracellular side of the membrane is more strongly blocked than that in the opposite direction. The apparent Ki increased approximately four-fold as applied potential was varied from +60 to −60 mV. Since GlyH-101 is negatively charged at pH 6-8, the simplest interpretation of these data is that GlyH-101 inhibition involves direct interaction with the channel pore at the extracellular side of the membrane. Accordingly, negative membrane potentials reduce the inhibitory efficacy of the negatively charged GlyH-101 by electrostatic repulsion, which drives the compound outside of the pore. In contrast, the open channel blocker glibenclamide, which is thought to act from the intracellular side of the CFTR pore (Sheppard & Robinson, 1997 *J. Physiol.*, 503:333-346), produces outward rectification of CFTR current-voltage relationship (Zhou et al., 2002, *J. Gen. Physiol.*, 120:647-662).

Analysis of GlyH-101 dose-response data also revealed an increase in apparent Hill coefficient at more negative membrane potentials, demonstrating the possibility of more than one inhibitor binding site within the pore and/or cooperative interaction between inhibitor molecules, as reported previously for other ion channels (Pottosin et al., 1999, *Biophys. J.*, 77:1973-1979; Brock et al., 2001, *J. Gen. Physiol.* 118:113-134). In support of the hypothesis that GlyH-101 is an open channel blocker, cell-attached patch-clamp experiments revealed fast closures within bursts of channel openings. The frequency of fast closures increased with GlyH-101 concentration, producing a reduction in mean channel open time as found for glibenclamide (Sheppard & Robinson, 1997*J. Physiol.*, 503:333-346). The appearance of closure events on the millisecond time scale classifies GlyH-101 as an "intermediate"-type channel blocker, similar to glibenclamide; in contrast, "fast" blockers reduce apparent single channel conductance, and "slow" blockers that cause closures of many seconds duration. In whole-cell patch-clamp and short-circuit current experiments, CFTR Cl⁻ conductance was fully inhibited at high concentrations (≧30 µM) of GlyH-101. Together these results demonstrate that the GlyH-101 inhibition mechanism involves direct CFTR pore occlusion at a site at or near the extracellular-facing pore surface.

Example 4

Physical Properties of Glycine Hydrazides

Interpretation of the voltage-dependent inhibition mechanism requires knowledge of the GlyH-101 ionic species that interacts with CFTR. Short-circuit studies indicated that the $K_i$ for GlyH-101 inhibition of CFTR Cl⁻ current was independent of pH in the range 6-8 (not shown), where the compound is highly water soluble (0.8-1.3 mM in water, 22° C.). The possible titrable groups on GlyH-101 in the pH range 3-10 include the secondary glycinyl amine and the resorcinolic hydroxyls. Spectrophotometric titration of GlyH-101 indicated at least two protonation/deprotonations at pH between 4 and 9 (FIG. 5A, top panel). To assign pKa values, GlyH-101 analogs that lacked one or more titrable groups were synthesized. Removal of the secondary amine (AceH-403) had little effect on the titration, with only a minor left-shift of the ascending portion of the curve, suggesting a pKa of ~5.5 for titration of the first phenolic hydroxyl. Removal of one ortho hydroxyl (GlyH-102) eliminated the descending portion of the curve, confirming the pKa of ~5.5 for the first para hydroxyl and ~8.5 for the second ortho hydroxyl. Removal of the aromatic ring containing the resorcinolic hydroxyls (ethyl N-(2-napthalenyl) glycinate, FIG. 5A, bottom panel) indicated a pKa ~4.7 for the residual secondary amine. From these data the deduced equilibria among the ionic forms of GlyH-101 is shown in FIG. 5B. GlyH-101 exists primarily as a singly charged anion at pH between 6 and 8.

Example 5

CFTR Inhibition in Mice In Vivo

Inhibition of CFTR-dependent airway epithelial Cl⁻ current in vivo was demonstrated by nasal potential difference (PD) measurements in mice. Nasal PDs were measured continuously in response to serial solution exchanges in which amiloride was added (to block ENaC Na⁺ channels) followed by Cl⁻ replacement by gluconate (to induce Cl⁻ dependent hyperpolarization), forskolin addition (to activate CFTR) and GlyH-101 addition (to inhibit CFTR). The representative PD recording in FIG. 6A (left panel) shows hyperpolarizations (more negative PDs) following low Cl⁻ and forskolin solutions, representing CFTR-independent and dependent Cl⁻ currents, respectively. Topical application of GlyH-101 in the perfusate rapidly reversed the forskolin-induced hyperpolarization. Averaged results from a series of measurements are summarized in FIG. 6A (right panel). Paired analysis of PD changes (ΔPD, FIG. 6B) indicated ~4 mV hyperpolarization after forskolin with depolarization of similar magnitude after GlyH-101; for comparison data are shown for CFTR$_{inh}$-172 from a previous study. In a separate series of experiments, nasal PDs were measured as in A except that all solutions contained DIDS or GlyH-101. FIG. 6C shows partial inhibition by DIDS of the (CFTR-independent) hyperpolarization produced by low Cl⁻ (left panel), and substantial inhibition by GlyH-101 of the forskolin-induced hyperpolarization (right panel). Together these results indicate rapid inhibition of upper airway CFTR Cl⁻ conductance by topical GlyH-101.

The efficacy of GlyH-101 in inhibiting cAMP/cholera toxin-induced intestinal fluid secretion was also evaluated. Short-circuit current experiments were done in different cell types and in intact mouse ileum under non-permeabilized conditions and in the absence of a Cl⁻ gradient. In each case CFTR was activated by CPT-cAMP after ENaC inhibition by amiloride. FIG. 7A shows similar $K_i$~5 µM for inhibition of cAMP-stimulated short-circuit current by GlyH-101 in T84 cells (top panel), primary human bronchial cell cultures (middle panel), and intact mouse ileum (bottom panel). Inhibition was ~100% at higher GlyH-101 concentrations. Cholera toxin-induced intestinal fluid secretion was measured in an in vivo closed-loop model in which loops for each mouse were injected with saline (control), cholera toxin (1 µg), or cholera toxin (1 µg)+GlyH-101 (0.25 µg). GlyH-101 was added to the lumen (rather than systemically) based on initial studies showing poor intestinal absorption and little effect of systemically administered compound. Compared to the saline control, the cholera toxin-induced increase in fluid secretion over 4 hours, quantified from loop weight-to-length ratio, was 80% reduced by GlyH-101.

Example 6

Synthesis of Highly Water Soluble CFTR Pore-Blocking Compounds

The strategy for design of highly water-soluble CFTR inhibitor compounds with minimal intestinal absorption was to modify the structure of GlyH-101 by addition of polar, bulky groups as shown in FIG. 8. From analysis of structure-activity relationship of glycine hydrazides compounds it was found that the minor modifications at the glycyl methyl position did not affect CFTR inhibition activity. Efficient synthesis of highly water soluble CFTR inhibitors were devised by utilizing a diethylbromomalonate intermediate (FIGS. 9-11). Reaction of 2-naphthalenamine with diethylbromomalonate followed by subsequent reaction with hydrazine generated a versatile malonic acid dihydrazide intermediate (FIG. 9). Condensation of this dihydrazide with 3,5-dibromo-2,4-dihydroxybenzaldehyde produced a key intermediate compound 4 which on further condensation with same aldehyde produced the compound MalH-1. Similarly, 2,4-disodium-disulfobenzaldehyde and 4-sodium-sulfophenylisothiocyanate were condensed with compound 4 to generate the compounds MalH-2 and MalH-3, respectively.

MalH-1 is structurally similar to GlyH-101 except for an additional benzaldehyde moiety that makes it doubly charged, bulkier and more hydrophilic. MalH-1 is water soluble to >5 mM. MalH-2 carries two disulfonic acid groups, and MalH-3 contains one sulfonic acid moiety with hydrophilic thiourea linker. Both compounds are freely soluble (>50% wt/volume, 20° C.) in water and saline.

Intermediate compound 4 was also used to generate MalH-(PEG)$_n$ and MalH-(PEG)$_n$B by condensation with various phenylisothiocyantes 6a and 6b carrying PEG (FIG. 10). The intermediate compounds 6a and 6b were synthesized by reaction of 1,4-phenylenediisothiocyante 5a and bis[(4-isothiocyanato)phenyl]methane 6b with appropriate amino-PEGs. The PEG moiety increased water solubility to 10 mM. Another approach for synthesis of PEG-ylated compounds involved incorporation of hydroxyethyl moiety onto glycyl methyl and further manipulating hydroxyl group to link PEG chain (FIG. 11). Reaction of bromobuterolactone with 2-naphthalenamine and subsequent reaction with hydrazine produced hydrazide 7. Using standard protection-deprotection Boc chemistry, this hydrazide was PEG-ylated by utilizing its hydroxyl group. The PEG-ylated hydrazide 11 was condensed with aromatic aldehyde to produce GlyH-(PEG)$_n$, which have similar was solubility as MalH-(PEG)$_n$.

Example 7

CFTR Inhibition with Highly Water Soluble CFTR Pore-Blocking Compounds

CFTR inhibition by MalH compounds was assayed by short-circuit current analysis using FRT cells expressing human wildtype CFTR. Apical membrane chloride current was measured after permeabilization of the cell basolateral membrane in the presence of a transepithelial chloride gradient. As shown in FIG. 12, CFTR was activated by the cell permeant cAMP agonist CPT-cAMP and then increasing MalH compound concentrations were added. The results show that inhibition was rapid and nearly complete at high MalH concentrations. In addition, the results also show that inhibitory potencies (K$_I$) were in the range 2-8 μM.

Short-circuit current analysis in CFTR-expressing epithelial cell monolayers showed prompt inhibition of chloride current in response to compound addition to the luminal solution. Importantly, near 100% block of chloride current was achieved at high inhibition concentrations. Also, the inhibitors were chemically stable in the presence of intestinal contents, and no toxicity was seen when the inhibitors were present at high concentration in cell cultures or when administered systemically to mice. The effective CFTR block of these water soluble impermeant compounds when added externally provides direct evidence that the site of the block is at the external-facing surface of CFTR.

Example 8

Intestinal Absorption and Antidiarrheal Efficacy Studies with Highly Water Soluble CFTR Pore-Blocking Compounds Intestinal absorption was measured in mice in vivo from the disappearance of MalH compounds from the lumens of closed mid-jejunal loops over 2 hours. In these experiments mannitol was included in the MalH-containing solutions to prevent fluid absorption. Absorption rates were referenced against a large FITC-dextran, which was assumed to undergo no absorption over the 2 hour study. The summarized data in FIG. 13, panel A, shows under 5% absorption of the MalH compounds in 2 hours, whereas the >90% of the thiazolidinone CFTR$_{inh}$-172 was absorbed over this time.

Antidiarrheal efficacy was assayed in closed mid-jejunal loops in mice. Loops were injected with saline or solutions of cholera toxin containing different concentrations of MalH compounds. Intestinal fluid secretion was determined at 6 hours by measurements of loop length and weight. The data summary in FIG. 13, panel B, shows a loop weight-to-length ratio (corresponding to 100% inhibition) of 0.09 in saline-injected loops, and 0.28 (corresponding to 0% inhibition) in cholera toxin-injected loops. The results show that each of the MalH compounds inhibited loop secretion in a dose-dependent manner with essentially complete inhibition at the higher concentrations.

The results show that the glycine hydrazide-based CFTR inhibitors undergo little intestinal absorption and are effective in preventing cholera toxin-induced fluid secretion in a rodent model of cholera toxin-induced fluid secretion. The advantages of antidiarrheal therapy using a non-absorbable compound are that high concentrations can be achieved in the gut with minimal concerns about toxicity and off-target effects related to cellular uptake and systems absorption.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for inhibiting cystic fibrosis transmembrane conductance regulator (CFTR) ion transport in a cell, the method comprising contacting the cell with a compound, wherein (a) the compound has the following formula (Ia):

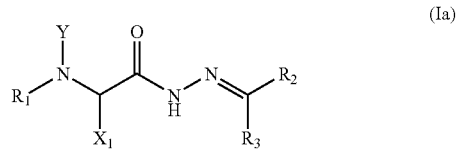

or a pharmaceutically acceptable salt or stereoisomer thereof, wherein X$_1$ is hydrogen or a substituted or unsubstituted, saturated linear or branched alkyl;

Y is hydrogen or substituted or unsubstituted, saturated linear or branched alkyl;

R₁ is unsubstituted phenyl,
substituted phenyl wherein phenyl is substituted with one or more of hydroxy, alkyl, and halogen,
substituted or unsubstituted anthracenyl, or
substituted or unsubstituted naphthalenyl;
R² is unsubstituted phenyl,
substituted phenyl, wherein phenyl is substituted with bromo or carboxy,
di(hydroxy)phenyl,
mono(halo)-mono(hydroxy)phenyl,
mono(halo)-di(hydroxy)phenyl,
mono(halo)-tri(hydroxy)phenyl,
di(halo)-mono(hydroxy)phenyl,
di(halo)-di(hydroxy)phenyl,
di(halo)-tri(hydroxy)phenyl,
mono(halo)-mono(hydroxy)-mono(alkoxy)phenyl,
mono(halo)-di(hydroxy)-mono(alkoxy)phenyl,
mono(halo)-mono(hydroxy)-di(alkoxy)phenyl,
mono(halo)-di(hydroxy)-di(alkoxy)phenyl,
di(halo)-mono(hydroxy)-mono(alkoxy)phenyl,
di(halo)-di(hydroxy)-mono(alkoxy)phenyl,
di(halo)-mono(hydroxy)-di(alkoxy)phenyl; and
R₃ is hydrogen or substituted or unsubstituted alkyl; or
(b) the compound has the following formula (Ie):

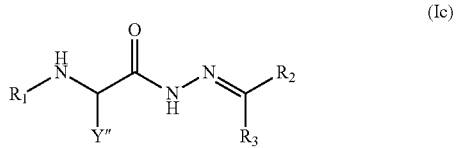

(Ic)

or a pharmaceutically acceptable salt or stereoisomer thereof,
wherein Y″ is a substituted or unsubstituted, saturated linear or branched alkyl; or an amide or ether linker attached to a polar molecule, wherein the polar molecule is selected from a substituted or unsubstituted phenyl group, a polyoxyalkyl polyether, a polyethyleneimine, a disaccharide, a trisaccharide, a polyalkylimine, and a small amino dextran;
R₁ is unsubstituted or substituted phenyl, substituted or unsubstituted quinolinyl, substituted or unsubstituted anthracenyl, or substituted or unsubstituted naphthalenyl;
R² is unsubstituted or substituted phenyl; and
R₃ is hydrogen or substituted or unsubstituted alkyl, thereby inhibiting CFTR ion transport in the cell.

2. The method of claim 1 wherein the cell is in a subject who has aberrantly increased intestinal secretion.

3. The method of claim 2 wherein the aberrantly increased intestinal secretion is secretory diarrhea.

4. The method of claim 1 wherein the cell is in a subject who has polycystic kidney disease.

5. The method of claim 1, wherein the compound has the formula of (Ia), and wherein $X_1$ is an alkyl selected from methyl or ethyl, or $X_1$ is substituted alkyl wherein the substituent is selected from a sulfo group, a carboxy group, a carboxamide group, a polyoxyalkyl polyether, a disaccharide, a substituted or unsubstituted phenyl group, or a polyethylene imine (PEI).

6. The method of claim 1, wherein the compound has the formula of (Ia), and wherein $X_1$ is $C_1$-$C_8$ alkyl.

7. The method of claim 1, wherein the compound has the formula of (Ia), and wherein $X_1$ is hydrogen, methyl, or ethyl.

8. The method of claim 1, wherein the compound has the formula of (Ia), and wherein $R_1$ is substituted or unsubstituted anthracenyl, or substituted or unsubstituted napthalenyl.

9. The method of claim 1, wherein the compound has the formula of (Ia), and wherein $R_1$ is substituted 2-naphthalenyl, unsubstituted 2-naphthalenyl, substituted 1-naphthalenyl, or unsubstituted 1-naphthalenyl.

10. The method of claim 1, wherein the compound has the formula of (Ia), and wherein $R_2$ is chosen from 3,5-dibromo-2,4-dihydroxyphenyl; 3,5-dibromo-4-hydroxyphenyl; 2,4-dihydroxyphenyl; 4-bromophenyl; 4-carboxyphenyl; and 3,5-dibromo-2-hydroxy-4-methoxyphenyl.

11. The method of claim 1, wherein the compound has the formula of (Ia), and wherein $R_3$ is hydrogen, methyl, or ethyl.

12. The method of claim 1, wherein the compound has the formula of (Ia), and wherein Y is substituted alkyl, and wherein the substituent is selected from a sulfo group, a carboxy group, a substituted or unsubstituted carboxamide group, a polyoxyalkylether group, a disaccharide, a polyamine, and a polyethyleneimine (PEI).

13. The method of claim 1, wherein the compound has the formula of (Ia), and wherein Y is $C_1$-$C_8$ alkyl.

14. The method of claim 1, wherein the compound has the formula of (Ia), and wherein Y is hydrogen; $X_1$ is hydrogen, methyl or ethyl; $R_1$ is mono-(halo)phenyl or unsubstituted napthalenyl; $R_2$ is di-(halo)-mono(hydroxy)phenyl or di-(halo)-di(hydroxy)phenyl; and $R_3$ is hydrogen or methyl.

15. The method of claim 1, wherein the compound has the formula (Ia), and has a structure selected from the following formulae:

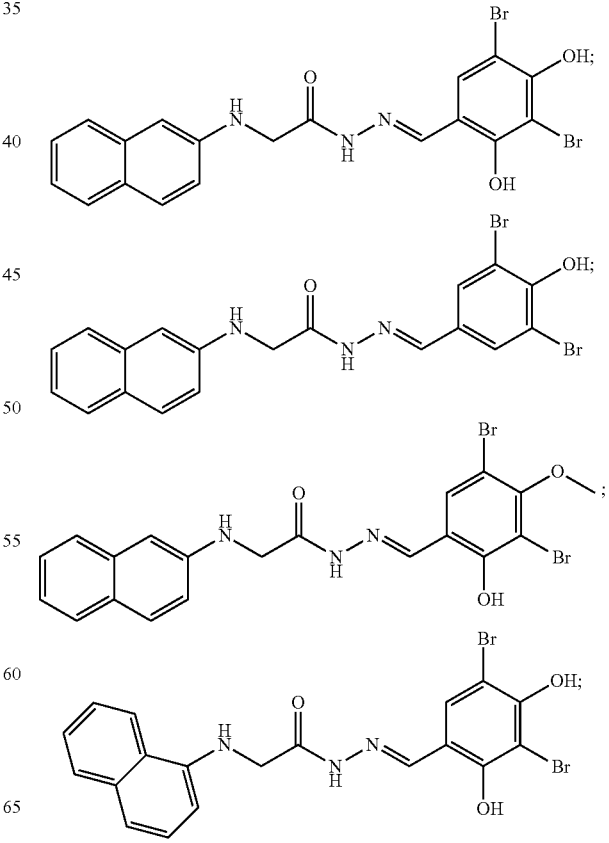

-continued
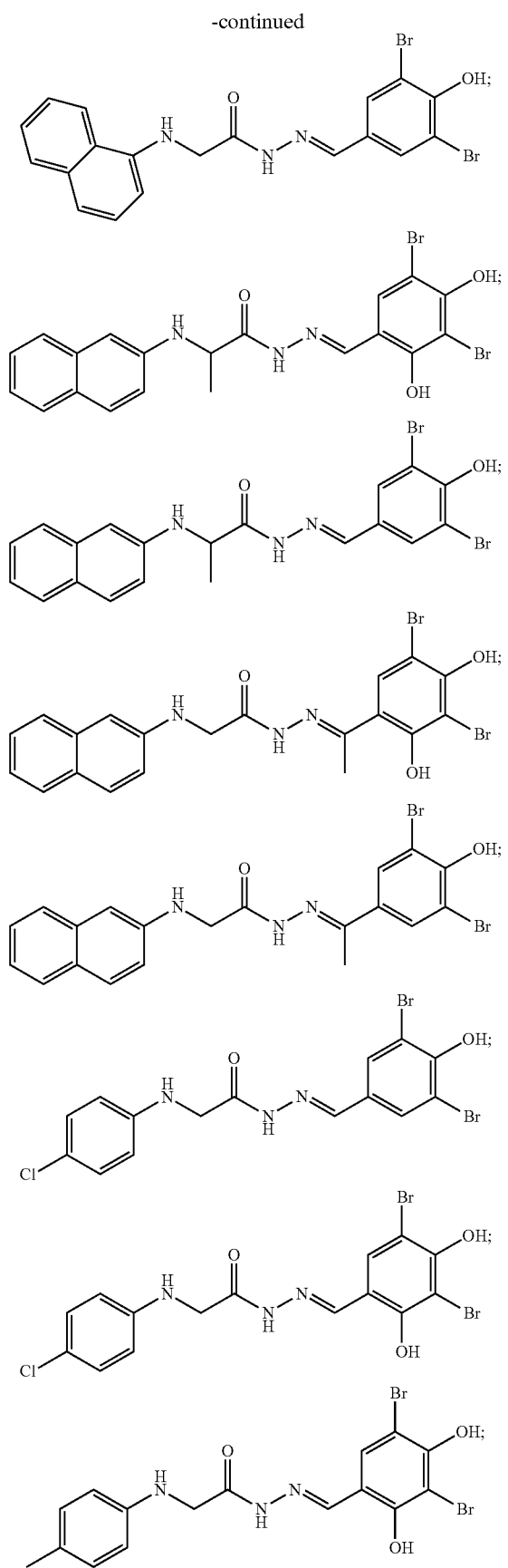
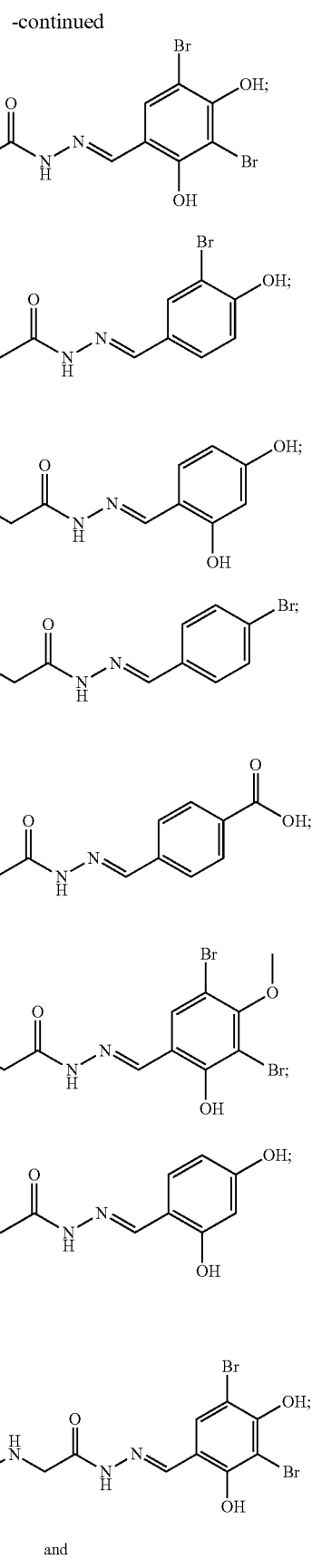
and

-continued

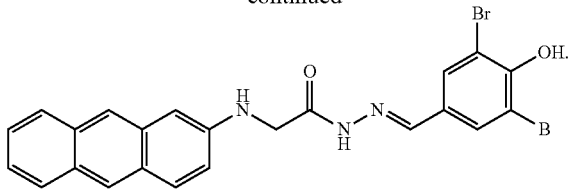

16. The method according to claim 1, wherein the compound of formula (Ia) has the following structure:

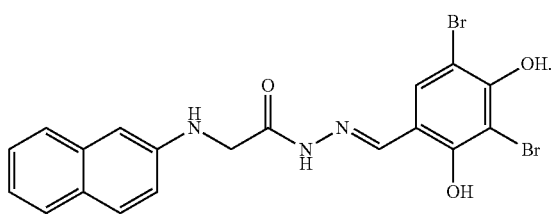

17. The method of claim 1, wherein the compound of formula (Ia) is a compound of formula (Ib):

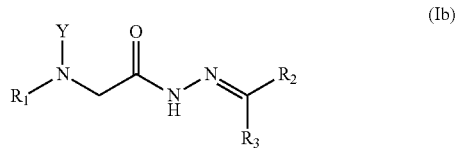

(Ib)

or a pharmaceutically acceptable salt or stereoisomer thereof,
wherein Y is hydrogen or a substituted or unsubstituted, saturated linear or branched alkyl;
$R_1$ is
  unsubstituted phenyl,
  substituted phenyl wherein phenyl is substituted with one or more of hydroxy, alkyl and halogen,
  substituted or unsubstituted anthracenyl, or
  substituted or unsubstituted naphthalenyl;
$R^2$ is unsubstituted phenyl,
  substituted phenyl, wherein phenyl is substituted with bromo or carboxy,
  di(hydroxy)phenyl,
  mono(halo)-mono(hydroxy)phenyl,
  mono(halo)-di(hydroxy)phenyl,
  mono(halo)-tri(hydroxy)phenyl,
  di(halo)-mono(hydroxy)phenyl,
  di(halo)-di(hydroxy)phenyl,
  di(halo)-tri(hydroxy)phenyl,
  mono(halo)-mono(hydroxy)-mono(alkoxy)phenyl,
  mono(halo)-di(hydroxy)-mono(alkoxy)phenyl,
  mono(halo)-mono(hydroxy)-di(alkoxy)phenyl,
  mono(halo)-di(hydroxy)-di(alkoxy)phenyl,
  di(halo)-mono(hydroxy)-mono(alkoxy)phenyl,
  di(halo)-di(hydroxy)-mono(alkoxy)phenyl,
  di(halo)-mono(hydroxy)-di(alkoxy)phenyl; and
$R_3$ is hydrogen or substituted or unsubstituted alkyl.

18. The method of claim 17, wherein $R_1$ is substituted or unsubstituted 1-naphthalenyl, substituted or unsubstituted 2-naphthalenyl, 2-chlorophenyl, 4-chlorophenyl, 4-methylphenyl, 2-methylphenyl, or 2-anthracenyl.

19. The method of claim 17, wherein $R_1$ is mono-(halo)phenyl; mono-(alkyl)phenyl; mono-(halo)napthalenyl; di-(halo)napthalenyl; mono-(hydroxy)napthalenyl; di-(hydroxy)napthalenyl; mono-(alkoxy)napthalenyl; di-(alkoxy)naphthalenyl; tri-(alkoxy)naphthalenyl; mono-(alkyl)naphthalenyl; di-(alkyl)napthalenyl; mono-(hydroxyl)-mono(sulfo)napthalenyl; mono-(hydroxy)-di(sulfo)napthalenyl; mono-(alkyl)-mono-(alkoxy)-napthalenyl; or mono-(alkyl)-di-(alkoxy)-napthalenyl.

20. The method of claim 17, wherein $R_2$ is 3,5-dibromo-2,4-dihydroxyphenyl; 3,5-dibromo-2,4,6-trihydroxyphenyl; 3,5-dibromo-4-hydroxyphenyl; 3,5-dibromo-2-dihydroxy-4-methoxyphenyl; 3-bromo-4-hydroxyphenyl; 2,4-dihydroxyphenyl; 4-bromophenyl; or 4-carboxyphenyl.

21. The method of claim 17, wherein $R_3$ is hydrogen or methyl.

22. The method of claim 17, wherein Y is a substituted alkyl, and wherein the substituent is selected from a sulfo group, a carboxy group, a substituted or unsubstituted carboxamide group, a polyoxyalkylether group, a disaccharide, a polyamine, and a polyethyleneimine (PEI).

23. The method of claim 17, wherein Y is alkyl.

24. The method of claim 17, wherein Y is hydrogen; $R_1$ is mono-(halo)phenyl or naphthalenyl; $R_2$ is di-(halo)-mono-(hydroxy)phenyl or di-(halo)-di-(hydroxy)phenyl; and $R_3$ is hydrogen or methyl.

25. The method of claim 17, wherein the compound for formula (Ib) has a structure selected from the following formulae:

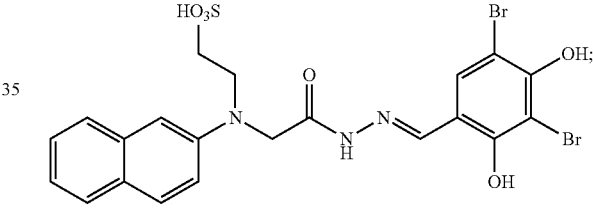

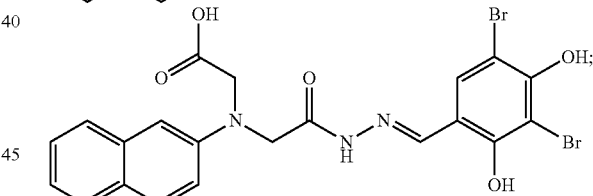

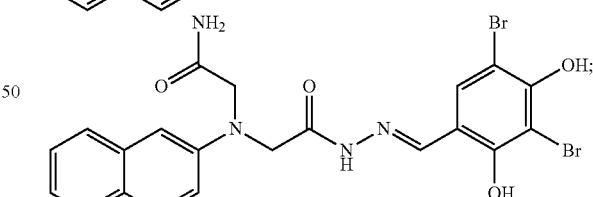

and

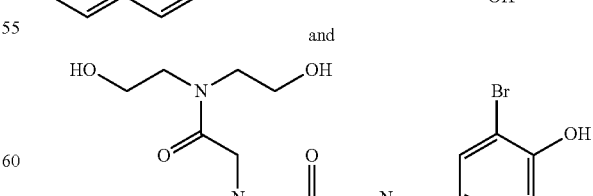

or a pharmaceutically acceptable salt thereof.

26. The method of claim 1, wherein the compound has the formula (Ie), and wherein $R_1$ is substituted or unsubstituted 1-naphthalenyl; substituted or unsubstituted 2-naphthalenyl; mono-(halo)phenyl; mono-(alkyl)phenyl; 2-chlorophenyl; 4-chlorophenyl; 4-methylphenyl; 2-methylphenyl; or 2-anthracenyl.

27. The method of claim 1, wherein the compound has the formula (Ie), and wherein $R_1$ is mono-(halo)naphthalenyl; di-(halo)naphthalenyl; mono-(hydroxy)napthalenyl; di-(hydroxy)napthalenyl; mono-(alkoxy)napthalenyl; di-(alkoxy)napthalenyl; tri-(alkoxy)napthalenyl; mono-(alkyl)napthalenyl; di-(alkyl)napthalenyl; mono-(hydroxy)-mono(sulfo)napthalenyl; mono-(hydroxy)-di(sulfo)napthalenyl; mono-(alkyl)-mono-(alkoxy)-naphthalenyl; or mono-(alkyl)-di-(alkoxy)-naphthalenyl.

28. The method of claim 1, wherein the compound has the formula (Ie), and wherein $R_1$ is phenyl substituted with one or more of hydroxy, alkyl, and halogen.

29. The method of claim 1, wherein the compound has the formula (Ie), and wherein $R_2$ is 3,5-dibromo-2,4-dihydroxyphenyl; 3,5-dibromo-2,4,6-trihydroxyphenyl; 3,5-dibromo-4-hydroxyphenyl; 3,5-dibromo-2-dihydroxy-4-methoxyphenyl; 3-bromo-4-hydroxyphenyl; 2,4-dihydroxyphenyl; 4-bromophenyl; or 4-carboxyphenyl.

30. The method of claim 1, wherein the compound has the formula (Ie), and wherein $R_2$ is phenyl substituted with bromo or carboxy,
  di(hydroxy)phenyl,
  mono(halo)-mono(hydroxy)phenyl,
  mono(halo)-di(hydroxy)phenyl,
  mono(halo)-tri(hydroxy)phenyl,
  di(halo)-mono(hydroxy)phenyl,
  di(halo)-di(hydroxy)phenyl,
  di(halo)-tri(hydroxy)phenyl,
  mono(halo)-mono(hydroxy)-mono(alkoxy)phenyl,
  mono(halo)-di(hydroxy)-mono(alkoxy)phenyl,
  mono(halo)-mono(hydroxy)-di(alkoxy)phenyl,
  mono(halo)-di(hydroxy)-di(alkoxy)phenyl,
  di(halo)-mono(hydroxy)-mono(alkoxy)phenyl,
  di(halo)-di(hydroxy)-mono(alkoxy)phenyl, or
  di(halo)-mono(hydroxy)-di(alkoxy)phenyl.

31. The method of claim 1, wherein the compound has the formula (Ie), and wherein $R_3$ is hydrogen or methyl.

32. The method of claim 1, wherein the compound has the formula (Ie), and wherein Y" is substituted alkyl, and wherein Y" is substituted with a sulfo group, a carboxy group, a substituted or unsubstituted carboxamide group, a polyoxyalkylether group, a disaccharide, a polyamine, a substituted or unsubstituted phenyl group, a polyethyleneimine (PEI), or a dendrimer from 0-10 generation.

33. The method of claim 1, wherein the compound has the formula (Ie), and wherein Y" is an amide or ether linker attached to a polar molecule, wherein the polar molecule is a polyoxyalkyl polyether selected from polyethylene glycol, polypropylene glycol, and polyhydroxyethyl glycerol.

34. The method of claim 1, wherein the compound has the formula (Ie), and wherein Y" is an amide or ether linker attached to a polar molecule, wherein the polar molecule is a substituted phenyl group selected from 2,4-dihydroxy-3,5-dibromophenyl; 2,4-disodium-disulfophenyl; and 3-monosodium-monosulfophenyl.

35. The method of claim 1, wherein the compound has the formula (Ie), and wherein the compound of formula (Ie) has a structure selected from the following formulae:

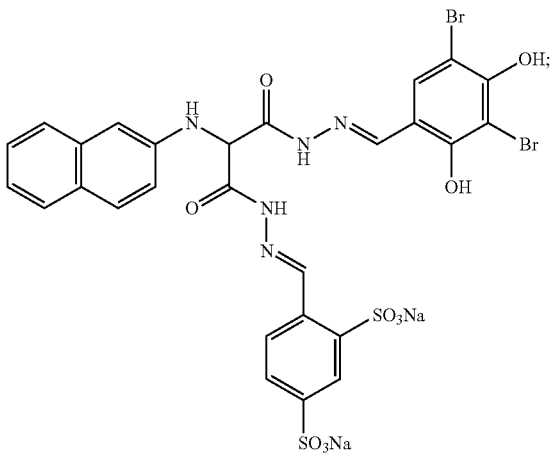

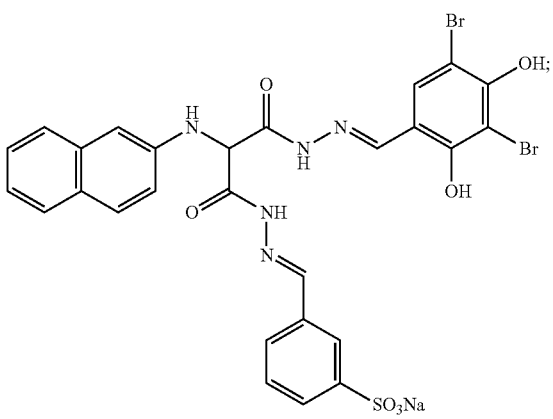

and

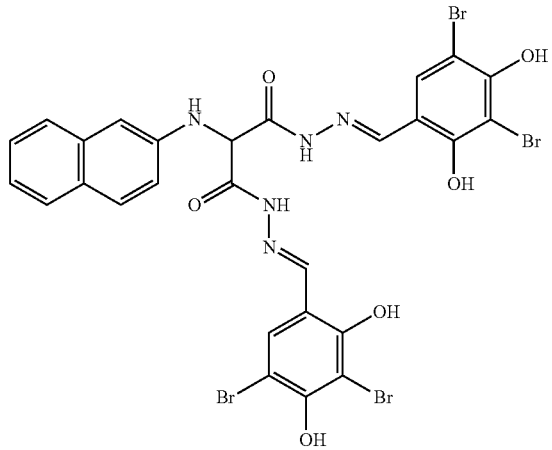

or a pharmaceutically acceptable salt thereof.

36. The method of claim 1, wherein the compound has the formula (Ie), and wherein the compound of formula (Ie) has a structure of the following formula:

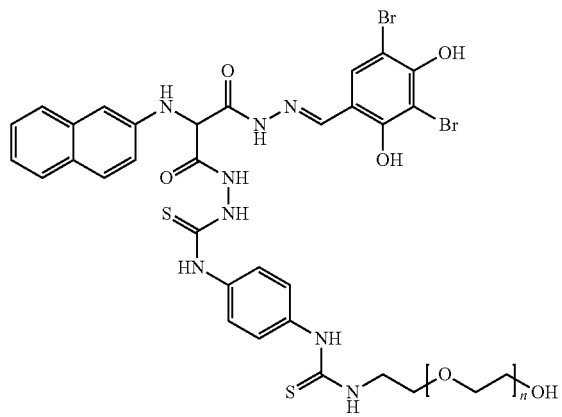

wherein n is 0-100.

37. The method of claim 1, wherein the compound has the formula (Ie), and wherein the compound of formula (Ie) has a structure of the following formula:

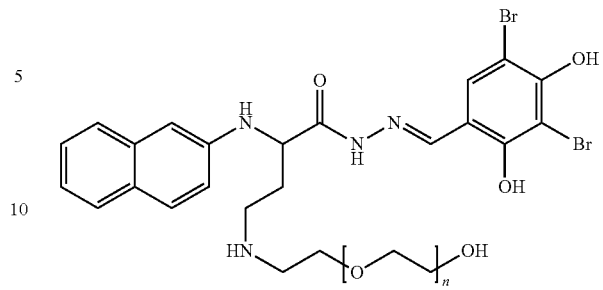

wherein n is 0-100.

38. The method of claim 1, wherein the compound has the formula (Ie), and wherein the compound is 2-naphthalenylamino-[(3,5-dibromo-2,4-dihydroxyphenyl)methylene][3-[4-(3-(PEG)$_n$-thioureido)diphenyl)-thioureido]propanedioic acid dihydrazide (MalH-(PEG)$_n$B).

39. The method of claim 1, wherein the method comprises contacting the cell in an in vitro assay.

\* \* \* \* \*

UNITED STATES PATENT AND TRADEMARK OFFICE
CERTIFICATE OF CORRECTION

| | | |
|---|---|---|
| PATENT NO. | : 7,888,332 B2 | Page 1 of 1 |
| APPLICATION NO. | : 12/175982 | |
| DATED | : February 15, 2011 | |
| INVENTOR(S) | : Alan S. Verkman et al. | |

It is certified that error appears in the above-identified patent and that said Letters Patent is hereby corrected as shown below:

In the Specification

<u>Column 1, Line 19:</u>
Delete "EY13574".

Signed and Sealed this
Third Day of December, 2024

*Katherine Kelly Vidal*

Katherine Kelly Vidal
*Director of the United States Patent and Trademark Office*